United States Patent
Bachlava et al.

(10) Patent No.: US 12,295,309 B2
(45) Date of Patent: *May 13, 2025

(54) MELON WITH RED FLESH LINKED TO EARLINESS

(71) Applicant: Seminis Vegetable Seeds, Inc., St. Louis, MO (US)

(72) Inventors: Eleni Bachlava, Fairfield, CA (US); Andrea K. Knox, St. Louis, MO (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,599

(22) Filed: Apr. 26, 2023

(65) Prior Publication Data

US 2023/0247956 A1    Aug. 10, 2023

Related U.S. Application Data

(63) Continuation of application No. 16/640,024, filed as application No. PCT/US2018/047258 on Aug. 21, 2018, now Pat. No. 11,678,624.

(60) Provisional application No. 62/548,954, filed on Aug. 22, 2017.

(51) Int. Cl.
| | |
|---|---|
| *A01H 6/34* | (2018.01) |
| *A01H 1/04* | (2006.01) |
| *A01H 5/08* | (2018.01) |

(52) U.S. Cl.
CPC ............. *A01H 6/344* (2018.05); *A01H 1/04* (2013.01); *A01H 1/045* (2021.01); *A01H 5/08* (2013.01)

(58) Field of Classification Search
CPC ...................................................... A01H 6/344
See application file for complete search history.

(56) References Cited

U.S. PATENT DOCUMENTS

| | | |
|---|---|---|
| 5,492,547 A | 2/1996 | Johnson |
| 11,678,624 B2 | 6/2023 | Bachlava et al. |
| 2006/0179510 A1* | 8/2006 | Copes .................... A01H 6/344 800/278 |

FOREIGN PATENT DOCUMENTS

WO    WO 2013/166195 A2    11/2013

OTHER PUBLICATIONS

Burrow, M. et al (1998). "Molecular Tools for the Study of Complex Traits," Chapter 2 in Molecular Dissection of Complex Traits, Paterson, A. H. ed., CRC Press: NY, New York pp. 13-29.

Cuevas, H. E. et al. (Aug. 2009). "A Consensus Linkage Map Identifies Genomic Regions Controlling Fruit Maturity and Beta-Carotene-Associated Flesh Color in Melon (*Cucumis melo* L.)," Theoretical and Applied Genetics 119.4:741-756.

Cuevas, H. E., et al. (Nov. 2008). "Mapping of Genetic Loci that Regulate Quantity of Beta-Carotene in Fruit of US Western Shipping Melon (*Cucumis melo* L.)," Theoretical and Applied Genetics 117(8):1345-1359.

Diaz, A. et al. (Jul. 28, 2011). "A Consensus Linkage Map for Molecular Markers and Quantitative Trait Loci Associated with Economically Important Traits in Melon (*Cucumis melo* L.)," BMC Plant Biol. 11:111, 14 pages.

GenBank Accession No. LN713260.1, last updated Mar. 5, 2015, located at https://www.ncbi.nlm.nih.gov/nuccore/N713260.1/, last visited on Jan. 5, 2023, one page.

Harel-Beja, R. et al. (Aug. 2010). "A Genetic Map of Melon Highly Enriched with Fruit Quality QTLs and EST Markers, Including Sugar and Carotenoid Metabolism Genes," Theoretical and Applied Genetics 121(3):511-533.

International Search Report and Written Opinion, dated Nov. 15, 2018, for PCT Application No. PCT/US2018/047258, filed Aug. 21, 2018, 6 pages.

Michelmore, R. W. et al. (Nov. 1, 1991). "Identification of Markers Linked to Disease-Resistance Genes by Bulked Segregant Analysis: A Rapid Method to Detect Markers in Specific Genomic Regions by Using Segregating Populations," Proc. Natl. Acad. Sci. (U.S.A.) 88(21):9828-9832.

Monforte, A. J. et al. (Feb. 2004). "Identification of Quantitative Trait Loci Involved in Fruit Quality Traits in Melon (*Cucumis Melo* L.)," Theoretical and Applied Genetics 108(4):750-758.

Oliver, M. et al. (Oct. 2001). "Construction of a Reference Linkage Map for Melon," Genome 44(5):836-845.

Openshaw, S. J. et al. (Aug. 5, 1994). "Marker-Assisted Selection in Backcross Breeding," Analysis of Molecular Marker Data 41-43.

Ragot, M. et al. (1995). "Marker-Assisted Backcrossing: Practical Example," INRA 72:45-56.

Reiter, R. S. et al. (Feb. 15, 1992). "Global and Local Genome Mapping in *Arabidopsis thaliana* by Using Recombinant Inbred Lines and Random Amplified Polymorphic DNAs," Proc. Natl. Acad. Sci. (U.S.A.) 89:1477-1481.

Tanksley, S. D. et al. (1988). "Molecular mapping plant chromosomes," Chromosome structure and function: Impact of new concepts Gustafson, J. P. ed., Plenum Press: New York, NY pp. 157-173.

Tzuri, G. et al. (Apr. 2015). "A 'Golden' SNP in CmOr Governs the Fruit Flesh Color of Melon (Cucumis Melo)," The Plant Journal 82.2:267-279.

Walton, M. (1993). "Molecular Markers: Which Ones to Use?" Seed World 22-29.

X-Rite Pantone. (2016). "A Guide to Understanding Color," 40 pages.

* cited by examiner

*Primary Examiner* — David H Kruse

(74) *Attorney, Agent, or Firm* — Morrison & Foerster LLP

(57) ABSTRACT

The present disclosure provides *Cucumis melo* inbred line CHA-ZA15-001AN. The present disclosure also provides methods to select, produce, and grow these plants, parts of such plants, and products made from those parts. The disclosure also includes progeny of the provided plants including hybrid and inbred lines.

12 Claims, 11 Drawing Sheets

Specification includes a Sequence Listing.

| | | | | | | | | | | | |
|---|---|---|---|---|---|---|---|---|---|---|---|
| TT | CC | CC | GG | AA | CC | TT | AA | GG | TT | AA | AA |
| 33.07 | 42.91 | 45.74 | 49.08 | 50.16 | 51.18 | 52.57 | 53.46 | 54.52 | 59.84 | 60.41 | 63.55 |
| NU0218743 | NU0219671 | NU0219672 | NU0219774 | NU0220446 | NCMEL0085792G5 | NU0219136 | NU0243542 | NU0243281 | NU0244254 | NU0244041 | NU0218915 |

ZA_CHA-192-ONTARIO-AN*4/BEST.0001>0067>0037>0065.@A-0011.

P_M_FLSH_4.1

P_M_FLSH

| ENTRY | NU0219672 45.74 | NU0220305 49.05 | NCMEL00857 9265 51.18 | NU0219136 52.57 | NCMEL00857 9809 53.01 | NU0243542 53.46 | NU0243281 54.52 | NU0220613 55.83 | NU0244507 55.97 | NU0244041 60.41 | HUE LS MEAN | MS GROUP |
|---|---|---|---|---|---|---|---|---|---|---|---|---|
| 10 | CC | GG | CC | TT | CC | AA | GG | AA | AA | AA | 0.3506 | G |
| 6 | TT | CC | CC | TT | CC | AA | AA | GG | GG | TT | 0.3628 | G |
| 7 | TT | CC | CC | TT | CC | AA | GG | AA | AA | AA | 0.3842 | F |
| 5 | CC | CC | TT | CC | TT | GG | AA | GG | GG | TT | 0.5061 | E |
| 9 | CC | GG | TT | CC | TT | GG | AA | GG | GG | TT | 0.5143 | DE |
| 8 | CC | GG | TT | CC | TT | AA | GG | AA | AA | AA | 0.5255 | CD |
| 3 | CC | GG | TT | CC | CC | GG | AA | GG | GG | AA | 0.5308 | BC |
| 1 | CC | GG | TT | TT | TT | AA | GG | AA | AA | AA | 0.5315 | BC |
| 4 | CC | GG | TT | CC | CC | GG | AA | AA | AA | AA | 0.5417 | AB |
| 2 | CC | GG | TT | CC | TT | GG | GG | AA | AA | AA | 0.5498 | A |

RED FLESH DONOR   ORANGE FLESH RP

| DAYS POST ANTHESIS | | | | | | GENOTYPE | | | | |
|---|---|---|---|---|---|---|---|---|---|---|
| 21 | 24/25 | 28 | 31/32 | 35/36 | 39 | 42.91 | 44.23 | 49.05 | 54.52 | |
| 5.150 | 4.933 | 6.100 | 11.367 | 12.700 | 13.000 | AC | AA | GG | AA | |
| 5.831 | 5.446 | 7.841 | 13.299 | 14.969 | 15.272 | AC | AG | GG | AA | |
| 4.519 | 5.417 | 7.550 | 11.301 | 10.905 | 15.265 | AA | AA | CG | AG | |
| 4.727 | 4.946 | 8.296 | 8.594 | 12.240 | 13.575 | AA | AA | GG | AA | |
| 4.880 | 7.238 | 10.338 | 12.777 | 14.129 | 14.625 | CC | GG | CC | GG | |
| 5.106 | 6.554 | 10.547 | 12.434 | 15.257 | 15.773 | AC | AG | CG | AA | |
|  | 5.779 | 6.594 | 7.424 | 9.657 | 11.983 | AA | AA | GG | AA | CHA-192-0053-MO |
| 5.893 | 8.706 | 13.549 | 15.551 | 16.033 | 17.000 | CC | GG | CC | GG | EARLINESS EVENT |
| 4.841 | 5.162 | 7.965 | 13.242 | 14.901 | 16.497 | AA | GG | CC | GG | CHA-192-ONTARIO-AN |
| 4.676 | 5.944 | 9.000 | 11.733 | 11.120 | 15.233 | AA | AG | CG | AG | |

FIG. 8

| OBSERVED COLOR | LS MEAN HUE | 42.907 | 44.235 | 49.050 | 54.517 |
|---|---|---|---|---|---|
| RED | 0.498 | AC | AA | GG | AA |
| RED | 0.502 | AC | AG | GG | AA |
| ORANGE | 0.342 | AA | AA | AG | AG |
| RED | 0.493 | AA | AA | GG | AA |
| ORANGE | 0.325 | CC | GG | CC | GG |
| SEG | 0.389 | AC | AG | CG | AA |
| RED | 0.478 | AA | AA | GG | AA |
| ORANGE | 0.331 | CC | GG | CC | GG |
| ORANGE | 0.360 | AA | GG | CC | GG |
| ORANGE | 0.330 | AA | AG | CG | AG |

FIG. 9

SEQUENCE LISTING

```
Sequence total quantity: 20
SEQ ID NO: 1             moltype = DNA  length = 121
FEATURE                  Location/Qualifiers
misc_difference          8
                         note = a, c, g, or t
misc_difference          97
                         note = a, c, g, or t
source                   1..121
                         mol_type = unassigned DNA
                         organism = Cucumis melo
SEQUENCE: 1
gaactaantt ttcaacaatc atatggtcaa taaaatgtat gttccgttta tatgttgatt   60
taatggtttt tgtacacagg ccattccatt ctaaacntcc tcagttagat agaaataaag  120
g                                                                  121

SEQ ID NO: 2             moltype = DNA  length = 410
FEATURE                  Location/Qualifiers
source                   1..410
                         mol_type = unassigned DNA
                         organism = Cucumis melo
SEQUENCE: 2
tgtcatgaat tgcgtgattt gctttaaatt atcccccaa gttttcagag gaagagagag   60
aagataaaca aaaaacctgc tcagattttg cttctcaaat tatgttcggt tgtcgcggtt  120
```

```
ttatagaata attttctttt ctaatttgta tgttcaggcg gagatttcgt tgtgtcgagt    180
ttacaaaaga gccggagtcg aaaatcaccc ttcactccct cgctctctcc cgtcaagagc    240
ttcgtcttcg cgaatgacaa cctcgtcgac gcctaagagt aatcttcttc cgggtggtgg    300
ctcggttaat gtcgtccaaa cttcatcctc atccacggat aaatttccga cgagtttcga    360
gtcgcaattc caccatcacc aacttcaaat tggctctgga gtcgaagcta                410

SEQ ID NO: 3             moltype = DNA   length = 121
FEATURE                  Location/Qualifiers
misc_difference          118
                         note = a, c, g, or t
source                   1..121
                         mol_type = unassigned DNA
                         organism = Cucumis melo
SEQUENCE: 3
cacccatgct gatgcactac gcctggcact agaaatgagt ccatacgaga gagaaaatcc     60
gtccaagact gcaggaagag ggacaacccc aggtcagaag aggaaggctg agttgcancc    120
t                                                                   121

SEQ ID NO: 4             moltype = DNA   length = 301
FEATURE                  Location/Qualifiers
misc_difference          261
                         note = a, c, g, or t
misc_difference          295
                         note = a, c, g, or t
misc_difference          299
                         note = a, c, g, or t
misc_difference          301
                         note = a, c, g, or t
source                   1..301
                         mol_type = unassigned DNA
                         organism = Cucumis melo
SEQUENCE: 4
gctgcctttt gtttggtcaa gtaatttgtt gtttgttctc gtttcatttt ttaaaatttt     60
gttttgggtt ttgtaggagc ttatggttta tgcgtcgtta aatgtgcttc ttcaaatggg    120
aaggggccta attcgttgga taatggagtt taaaaagtgg agaggttact tgaagagaaa    180
cggcgagcag aattgtctgc gcggatcgct tctggcgaat ttaccgtcga aaaaactggg    240
tatacaatta tttgtgtttt nttttttattt tctttatttc tttttttcta agttntggnt    300
n                                                                   301

SEQ ID NO: 5             moltype = DNA   length = 17
FEATURE                  Location/Qualifiers
source                   1..17
                         mol_type = unassigned DNA
                         organism = Cucumis melo
SEQUENCE: 5
aaaaccattg aatcaac                                                    17

SEQ ID NO: 6             moltype = DNA   length = 18
FEATURE                  Location/Qualifiers
source                   1..18
                         mol_type = unassigned DNA
                         organism = Cucumis melo
SEQUENCE: 6
aaaaccatt aaatcaac                                                    18

SEQ ID NO: 7             moltype = DNA   length = 32
FEATURE                  Location/Qualifiers
source                   1..32
                         mol_type = unassigned DNA
                         organism = Cucumis melo
SEQUENCE: 7
caatcatatg gtcaataaaa tgtatgttcc gt                                   32

SEQ ID NO: 8             moltype = DNA   length = 25
FEATURE                  Location/Qualifiers
source                   1..25
                         mol_type = unassigned DNA
                         organism = Cucumis melo
SEQUENCE: 8
gtttagaatg gaatggcctg tgtac                                           25

SEQ ID NO: 9             moltype = DNA   length = 19
FEATURE                  Location/Qualifiers
source                   1..19
                         mol_type = unassigned DNA
                         organism = Cucumis melo
SEQUENCE: 9
ccaaacttca tcctcatcc                                                  19
```

-continued

```
SEQ ID NO: 10            moltype = DNA   length = 18
FEATURE                  Location/Qualifiers
source                   1..18
                         mol_type = unassigned DNA
                         organism = Cucumis melo
SEQUENCE: 10
caaacttcat cgtcatcc                                                    18

SEQ ID NO: 11            moltype = DNA   length = 20
FEATURE                  Location/Qualifiers
source                   1..20
                         mol_type = unassigned DNA
                         organism = Cucumis melo
SEQUENCE: 11
ggtggtggct cggttaatgt                                                  20

SEQ ID NO: 12            moltype = DNA   length = 21
FEATURE                  Location/Qualifiers
source                   1..21
                         mol_type = unassigned DNA
                         organism = Cucumis melo
SEQUENCE: 12
ggtggaattg cgactcgaaa c                                                21

SEQ ID NO: 13            moltype = DNA   length = 17
FEATURE                  Location/Qualifiers
source                   1..17
                         mol_type = unassigned DNA
                         organism = Cucumis melo
SEQUENCE: 13
cagtcttgga tggattt                                                     17

SEQ ID NO: 14            moltype = DNA   length = 16
FEATURE                  Location/Qualifiers
source                   1..16
                         mol_type = unassigned DNA
                         organism = Cucumis melo
SEQUENCE: 14
agtcttggac ggattt                                                      16

SEQ ID NO: 15            moltype = DNA   length = 24
FEATURE                  Location/Qualifiers
source                   1..24
                         mol_type = unassigned DNA
                         organism = Cucumis melo
SEQUENCE: 15
ggcactagaa atgagtccat acga                                             24

SEQ ID NO: 16            moltype = DNA   length = 22
FEATURE                  Location/Qualifiers
source                   1..22
                         mol_type = unassigned DNA
                         organism = Cucumis melo
SEQUENCE: 16
gcaactcagc cttcctcttc tg                                               22

SEQ ID NO: 17            moltype = DNA   length = 18
FEATURE                  Location/Qualifiers
source                   1..18
                         mol_type = unassigned DNA
                         organism = Cucumis melo
SEQUENCE: 17
ctccactttt ttaactcc                                                    18

SEQ ID NO: 18            moltype = DNA   length = 16
FEATURE                  Location/Qualifiers
source                   1..16
                         mol_type = unassigned DNA
                         organism = Cucumis melo
SEQUENCE: 18
ccacttttta aactcc                                                      16

SEQ ID NO: 19            moltype = DNA   length = 25
FEATURE                  Location/Qualifiers
source                   1..25
                         mol_type = unassigned DNA
                         organism = Cucumis melo
SEQUENCE: 19
gcgtcgttaa atgtgcttct tcaaa                                            25
```

```
SEQ ID NO: 20          moltype = DNA   length = 23
FEATURE                Location/Qualifiers
source                 1..23
                       mol_type = unassigned DNA
                       organism = Cucumis melo
SEQUENCE: 20
cgccgtttct cttcaagtaa cct                                          23
```

MELON WITH RED FLESH LINKED TO EARLINESS

CROSS-REFERENCE TO RELATED APPLICATION

This application is a Continuation of U.S. application Ser. No. 16/640,024, filed Aug. 21, 2018, which is a U.S. National Stage Application of International Application No. PCT/US2018/047258, filed Aug. 21, 2018, which claims priority to U.S. Provisional Application No. 62/548,954, filed Aug. 22, 2017, all of which are incorporated herein by reference, in their entireties.

REFERENCE TO AN ELECTRONIC SEQUENCE LISTING

The contents of the electronic sequence listing (777052058001SEQLIST.xml; Size: 22,129 bytes; and Date of Creation: Apr. 24, 2023) is herein incorporated by reference in its entirety.

FIELD OF THE INVENTION

The present disclosure relates to the field of plant breeding and, more specifically, to methods and compositions for growing melon plants that produce fruit comprising a red flesh phenotype linked with an earliness phenotype.

BACKGROUND OF THE INVENTION

Melon fruits are highly appreciated worldwide and are often eaten as a fresh product. Melons are members of the gourd family (Cucurbitaceae), a class of trailing annual vines that also includes squash, pumpkin, and cucumber. They have large broad leaves, stems covered in light prickles, and small yellow flowers. The fruit themselves are soft fleshed with a central cavern containing seeds, surrounded by a thick protective rind.

Taxonomically, melons are broadly divided into two groups: watermelons (species *Citrullus lanatus*) and musk melons (species *Cucumis melo* L.). *C. melo* includes a wide variety of cultivars producing fruits of different shape, external appearance, and flesh color. These cultivars can be classified into additional horticultural varieties, or groups, further comprising different melon market classes. Three such groups are *Cantalupensis, Reticulatus,* and *Inodorus* and include, for example, market classes such as Canary, Cantaloupe (including Western Shipper, North American, and Charentais types), Casaba, Hami, Honeydew, Navajo Yellow, Piel de Sapo, Santa Claus, Sugar melon, Ambrosia, Bailan, Galia, Ogen, Persian, and Sharlyn.

One important goal of melon breeding is to combine various desirable traits in a single variety or hybrid. While breeding efforts to date have provided a number of useful melon lines and varieties with beneficial traits, there remains a need in the art for new lines and varieties with further improved traits and methods for their production. In many cases, such efforts have been hampered by difficulties in identifying and using alleles segregating with beneficial traits.

SUMMARY OF THE INVENTION

This disclosure provides for, and includes, a *Cucumis melo* plant, or plant part that produces fruit with a red flesh trait linked to an earliness trait on *Cucumis melo* Linkage Group 6 of the ICuGI Public Consensus Genetic Map.

This disclosure also provides for, and includes, a *Cucumis melo* seed capable of growing a *Cucumis melo* plant that produces fruit with a red flesh trait linked to an earliness trait on *Cucumis melo* Linkage Group 6 of the ICuGI Public Consensus Genetic Map.

This disclosure further provides a method to detect a *Cucumis melo* plant with a red flesh locus linked to an earliness locus on *Cucumis melo* Linkage Group 6 of the ICuGI Public Consensus Genetic Map comprising obtaining at least one *Cucumis melo* seed derived from a cross where at least one parent comprises a red flesh trait linked to an earliness trait, assaying the obtained seed, or a plant grown from that seed, for at least one red flesh allele linked to at least one allele of an earliness locus on *Cucumis melo* Linkage Group 6 of the ICuGI Public Consensus Genetic Map, and detecting a *Cucumis melo* seed, or a *Cucumis melo* plant grown from that seed, with a homozygous red flesh allele linked to at least one allele of an earliness locus on *Cucumis melo* Linkage Group 6 of the ICuGI Public Consensus Genetic Map.

This disclosure further provides a method of producing *Cucumis melo* plants comprising the steps of planting a *Cucumis melo* seed and growing the seed into a *Cucumis melo* plant that can produce a fruit having red flesh with a hue angle less than 65° and a red flesh trait linked to an earliness trait on *Cucumis melo* Linkage Group 6 of the ICuGI Public Consensus Genetic Map.

BRIEF DESCRIPTION OF THE SEQUENCE LISTING

SEQ ID NO:1 is the sequence of marker NCMEL008579265.
SEQ ID NO:2 is the sequence of marker NU0220305.
SEQ ID NO:3 is the sequence of marker NU0243432.
SEQ ID NO:4 is the sequence of marker NCMEL009758372.
SEQ ID NO:5 is the sequence of TAQMAN probe 1 for NCMEL008579265.
SEQ ID NO:6 is the sequence of TAQMAN probe 2 for NCMEL008579265.
SEQ ID NO:7 is the sequence of primer 1 used to amplify a region containing the polymorphism in NCMEL008579265.
SEQ ID NO:8 is the sequence of primer 2 used to amplify a region containing the polymorphism in NCMEL008579265.
SEQ ID NO:9 is the sequence of TAQMAN probe 1 for NU0220305.
SEQ ID NO:10 is the sequence of TAQMAN probe 2 for NU0220305.
SEQ ID NO:11 is the sequence of primer 1 used to amplify a region containing the polymorphism in NU0220305.
SEQ ID NO:12 is the sequence of primer 2 used to amplify a region containing the polymorphism in NU0220305.
SEQ ID NO:13 is the sequence of TAQMAN probe 1 for NU0243432.
SEQ ID NO:14 is the sequence of TAQMAN probe 2 for NU0243432.
SEQ ID NO:15 is the sequence of primer 1 used to amplify a region containing the polymorphism in NU0243432.

SEQ ID NO:16 is the sequence of primer 2 used to amplify a region containing the polymorphism in NU0243432.

SEQ ID NO:17 is the sequence of TAQMAN probe 1 for NCMEL009758372.

SEQ ID NO:18 is the sequence of TAQMAN probe 2 for NCMEL009758372.

SEQ ID NO:19 is the sequence of primer 1 used to amplify a region containing the polymorphism in NCMEL009758372.

SEQ ID NO:20 is the sequence of primer 2 used to amplify a region containing the polymorphism in NCMEL009758372.

BRIEF DESCRIPTION OF THE DRAWINGS

FIG. 3 (right) is a graph showing the Least Square Mean (LSM) of Brix for each entry at 4 time points. Genetic map locations are given in cM according to the Monsanto Consensus Genetic Map.

FIG. 4 is a diagram of the "earliness event" donor line. The "BEST" introgression includes the chromosomal interval from markers NU0219671 to NU0219672. The remaining markers comprise alleles from the recurrent parent CHA-192-ONTARIO-AN. Genetic map locations are given in cM according to the Monsanto Consensus Genetic Map.

FIG. 5 is a graph and diagram for the genetic mapping of the red flesh phenotype.

FIG. 6 is a diagram of fine mapping results for the red flesh phenotype on Linkage Group 4 of the Monsanto Consensus Genetic Map. Flesh color is quantitatively scored using the hue angle. Genotypes of ten $F_6$ recombinant plants are shown. Red flesh (hue angle less than or equal to 63°) correlates with red donor (CHA-192-0058-MO) alleles while orange flesh (hue angle greater than 63°) correlates with alleles of the orange flesh recurrent parent (CHA-38-MAKER-AN). Genetic map locations are given in cM according to the Monsanto Consensus Genetic Map.

FIG. 7 is a diagram and graph showing increases in degrees Brix over time in $F_2$ recombinants of the coupling cross described in Example 4, compared to controls. The LSM of Brix accumulation is determined and set to zero at 21 Days Post Anthesis (DPA). Subsequent entries represent the increase in degrees Brix over the previous time entry.

FIG. 8 is a diagram showing total Brix accumulation in $F_2$ recombinants of the coupling cross described in Example 4 and controls. The LSM for Brix accumulation is shown for each entry at each time point on the left; the genetic haplotype for each line is shown to the right. Genetic map locations are given in cM according to the Monsanto Consensus Genetic Map.

FIG. 9 is a diagram correlating flesh color with haplotypes across the earliness and red flesh intervals in $F_2$ recombinants of the coupling cross. The visually observed flesh color is indicated. Flesh color is quantitatively scored using the hue LSM. The entry labeled "seg" is segregating for both orange and red flesh color.

DETAILED DESCRIPTION OF THE INVENTION

Figure 1:
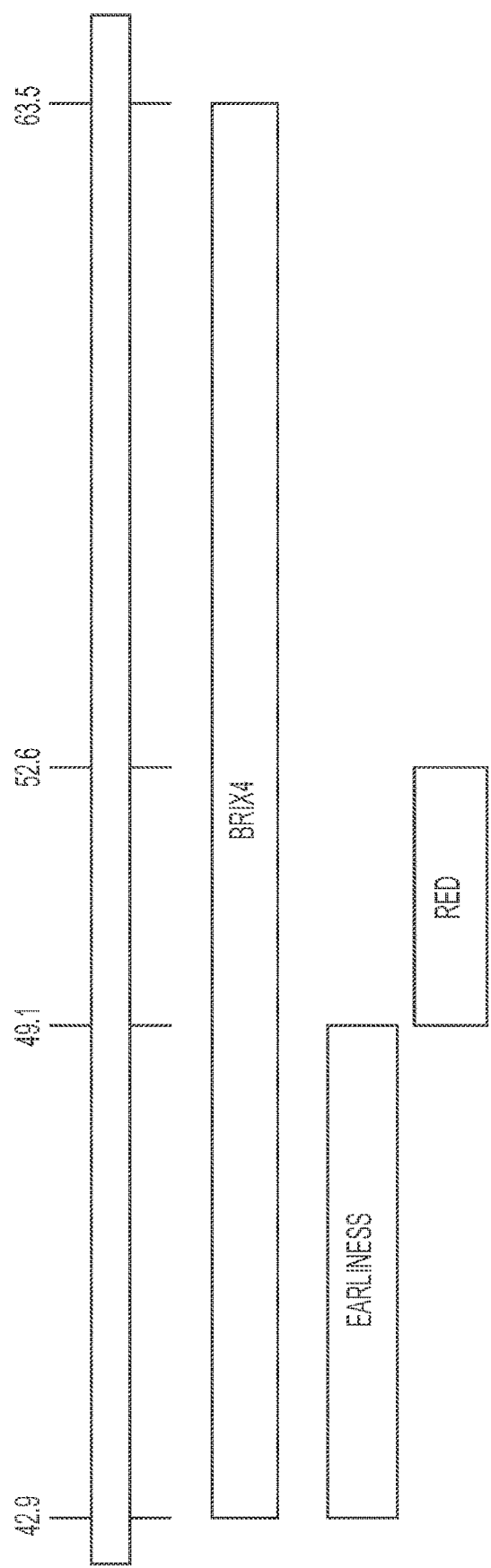
FIG. 1 is a diagram of *Cucumis melo* Linkage Group 4 of the Monsanto Consensus Genetic Map with genetic map locations given according to the Monsanto Consensus Genetic Map. Map positions of the BRIX4 QTL, the interval containing the earliness locus, and the interval containing the red flesh locus are shown.

This application provides for, and includes, a *Cucumis melo* plant, or part thereof, wherein a fruit obtained from the *Cucumis melo* plant comprises a red flesh trait linked to an earliness trait on *Cucumis melo* Linkage Group 4 of the Monsanto Consensus Genetic Map.

In an aspect, the *Cucumis melo* plant comprising red flesh and earliness provided in this application are members of the gourd family (Cucurbitaceae). In a further aspect, the *Cucumis melo* plant comprising red flesh and earliness provided in this application is a subspecies selected from the group consisting of *Cucumis melo, Cucumis melo agrestis, Cucumis melo cantalupo, Cucumis melo conomon, Cucumis melo inodorus, Cucumis melo texanus, Cucumis melo dudaim, Cucumis melo flexuosus*, and *Cucumis melo momordica*. In a further aspect, the *Cucumis melo* plant comprising red flesh and earliness provided in this application is a hybrid. In a further aspect, the *Cucumis melo* plant comprising red flesh and earliness provided in this application is an inbred.

As used herein, the terms "variety", "elite variety", and "cultivar" means a group of similar plants that by their genetic pedigrees and performance are not found in nature and can be distinguished from other varieties within the same species.

In an aspect, the *Cucumis melo* plant comprising red flesh and earliness provided in this application can be classified as a horticultural variety selected from the group consisting of *Cantalupensis, Inodorus*, and *Reticulatus*. In a further aspect, the *Cucumis melo* plant of the horticultural variety *Cantalupensis* comprises a market class selected from the group consisting of Earl's Type, House, Galia, Charentais, and Ogen. In a further aspect, the *Cucumis melo* plant of the horticultural variety *Inodorus* comprises a market class selected from the group consisting of Amarillo, Honeydew, Piel de Sapo, Rochet, Negro, Crenshaw, and Tendral. In a further aspect, the *Cucumis melo* plant of the horticultural variety *Reticulatus* is a plant of the Hami melon market class.

In an aspect, the *Cucumis melo* plant comprising red flesh and earliness provided in this application may be part of a plurality of plants. In some aspects, the *Cucumis melo* plant or plurality of plants of the present disclosure may be grown in a field. In other aspects, the *Cucumis melo* plant or plurality of plants of the present disclosure may be grown in a greenhouse.

Also provided for and included in the present disclosure are parts of the *Cucumis melo* plant comprising red flesh and earliness. In further aspects, the plant part of the present disclosure is a seed, fruit, leaf, cotyledon, hypocotyl, meristem, embryo, endosperm, root, shoot, stem, pod, flower, inflorescence, stalk, pedicel, style, stigma, receptacle, petal, sepal, pollen, anther, filament, ovary, ovule, pericarp, phloem, vascular tissue, or a scion. In a further aspect, the application provides plant parts that are epidermal cells, stomata cells, leaves, root hairs, storage roots, or tubers. In an aspect, the plant part is a tissue culture of cells. In a further aspect, the plant part is a plant cell in tissue culture. In a further aspect, the plant or part thereof is grown from a cell in tissue culture.

A tissue culture of regenerable cells of the *Cucumis melo* plant comprising red flesh and earliness is provided in this application. In one aspect, the tissue culture comprises cells or protoplasts from a plant part selected from the group consisting of an embryo, a meristem, a cotyledon, a pollen grain, a leaf, an anther, a root, a root tip, a pistil, a flower, a fruit, a seed, and a stalk.

In an aspect, this application provides for and includes *Cucumis melo* plant cells, tissues, and organs from the *Cucumis melo* plant comprising red flesh and earliness that are not reproductive cells and do not function during the natural reproduction of the plant. In another aspect, this application also provides for and includes *Cucumis melo* plant cells, tissues, and organs that are reproductive material and function during the natural reproduction of the plant. In another aspect, this application provides for and includes *Cucumis melo* plant cells, tissues, and organs that cannot maintain themselves via photosynthesis. In another aspect, this application also provides for and includes somatic *Cucumis melo* plant cells. Somatic cells, in contrast to germline cells, do not function during plant reproduction.

The *Cucumis melo* cells, tissues, and organs may be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, or vascular tissue. In a further aspect, this application provides epidermal cells, stomata cells, leaf or root hairs, storage roots, or tubers. In another aspect, this application provides a protoplast from the *Cucumis melo* plant comprising red flesh and earliness. In another aspect, this application provides a plant grown in tissue culture from calli that is created from any of the cell types recited herein.

It is known and understood in the art that *Cucumis melo* plants naturally reproduce via seeds, not via asexual reproduction or vegetative propagation. In one aspect, this application provides *Cucumis melo* endosperm. In another aspect, this application provides *Cucumis melo* endosperm cells. In a further aspect, this application provides a triploid plant that cannot reproduce sexually or produce seeds. In another aspect, this application provides a male or female sterile *Cucumis melo* plant, which cannot reproduce without human intervention.

In a further aspect, this application provides processed products made from the disclosed *Cucumis melo* plants. Such products include, but are not limited to, cut melon, meal, juice, oil, plant extract, starch, or fermentation or digestion products.

In an aspect, a *Cucumis melo* seed is provided. In a further aspect, a *Cucumis melo* seed is provided that is capable of growing a *Cucumis melo* plant that can produce a fruit of the present disclosure. In a further aspect, a *Cucumis melo* seed is provided that is capable of growing a *Cucumis melo* plant that can produce a fruit comprising a red flesh trait linked to an earliness trait on *Cucumis melo* Linkage Group 4 of the Monsanto Consensus Genetic Map as described in this application.

In an aspect, a *Cucumis melo* fruit, or melon, is provided. A melon fruit is an abscising organ that is soft fleshed with a central cavern containing seeds, surrounded by a thick protective rind. *Cucumis melo* includes a wide variety of cultivars producing fruits of different shape, external appearance, and flesh color. Melon fruit become sweet as they ripen, or mature, and sweetness can be objectively measured.

As used herein, the term "maturity" means maturity of fruit development. Melon maturity is correlated with the time of maximum acquisition of desirable traits such as fruit size, shape, texture, flesh color, and Brix accumulation. Melon maturity is also correlated with the time of optimal fruit harvest.

Earliness is an important agronomic trait, as it allows growers to bring the harvest to market sooner and reduces the risks of crop loss. For example, many growing areas have an off-season with weather conditions that are detrimental to agriculture, such as cold, rain, or reduced sunlight. By growing an early maturing hybrid, a farmer could reduce the risk that his crop will not have been harvested prior to the onset of these conditions. Additionally, in regions where back-to-back crop cycles are possible, an early harvest will allow a second planting to fit more readily within ideal growing conditions. Also, the first fruits to market in a growing season can often fetch a premium price not available when the market is saturated. Further, disease pressures often build up throughout a growing season and an early harvest will avoid the more severe disease pressures that occur late in the season or allow harvest from a field before disease symptoms fully develop and affect marketable yield from a crop.

As used herein, "Days Post Anthesis" or "DPA" refers to a measurement of time after the flowering of a plant. Start of anthesis refers to the time at which a flower bud opens and can be pollinated. For example, measurement of days post anthesis begins with flagging a flower at anthesis and setting that day as day zero. Days after anthesis are referred to as 1 day post anthesis, 2 days post anthesis, 3 days post anthesis, and so on.

As used herein, the term "earliness" or an "earliness trait" means a phenotype wherein maturity of fruit development as determined by Brix accumulation occurs earlier when compared to a *Cucumis melo* plant without "earliness" or an "earliness trait". For example, a melon displaying "earliness" or an "earliness trait" will reach mature Brix levels earlier when compared to an isogenic *Cucumis melo* melon plant without "earliness" or an "earliness trait".

As used herein, the term "Brix" ("degree Brix" or "° Bx") is used here to quantify the mass ratio of dissolved solids, such as sucrose, to water in a liquid and is given in units of degrees (°). More specifically, a measurement of the Brix level of a melon fruit may be made according to methods well known in the art, for instance by use of a saccharimeter or refractometer (e.g. Refracto 30PX, Mettler-Toledo, Columbus, OH). For instance, a measurement of 10° Bx corresponds to about 7-8 grams of dissolved solids including sucrose per 100 grams of liquid. In certain aspects the Brix level of such melon fruit may be, for instance, at least 9, 9.5, or 10° Bx.

As used herein, the term "soluble solids" means the percent of solid material dissolved in aqueous solution found in the edible portion of the fruit. As used herein, soluble solids are measured quantitatively with a refractometer as degrees Brix. Brix is formally defined as weight percent sucrose: if the only soluble solid present in an aqueous solution is sucrose, an actual percentage sucrose will then be measured. However, if other soluble solids are present, as is almost always the case, the reading is not equal to the percentage sucrose, but approximates the overall percentage of soluble solids in the sample. In short, although Brix is technically defined as weight percent sucrose, those of skill in the art recognize that weight percent soluble solids, as obtained with a refractometer, approximate weight percent sucrose and accurately indicate sweetness. Therefore, the higher the percentage soluble solids, as indicated by degree Brix, the higher the perceived sweetness of the fruit.

As used herein, "peak Brix accumulation" refers to a phenotype wherein a melon fruit reaches 95% of its maximum Brix accumulation. The time to "peak Brix accumulation" from days post anthesis is measured when assaying the earliness phenotype.

In an aspect, the *Cucumis melo* plant that produces fruit that comprises a red flesh trait linked to an earliness trait on *Cucumis melo* Linkage Group 4 of the Monsanto Consensus Genetic Map reaches peak Brix accumulation earlier than a fruit obtained from an isogenic plant lacking an earliness trait. In a further aspect, the *Cucumis melo* plant produces fruit that reach peak Brix accumulation at least three days earlier than a fruit obtained from an isogenic plant lacking an earliness trait. In a further aspect, the *Cucumis melo* plant produces fruit that reach peak Brix accumulation at least four days earlier than a fruit obtained from an isogenic plant lacking an earliness trait. In a further aspect, the *Cucumis melo* plant produces fruit that reach peak Brix accumulation at least five days earlier than a fruit obtained from an isogenic plant lacking an earliness trait. In a further aspect, the *Cucumis melo* plant produces fruit that reach peak Brix accumulation at least six days earlier than a fruit obtained from an isogenic plant lacking an earliness trait. In a further aspect, the *Cucumis melo* plant produces fruit that reach peak Brix accumulation at least three days earlier, at least four days earlier, at least five days, or at least six days earlier than a fruit obtained from an isogenic plant lacking an earliness trait. In an aspect, the *Cucumis melo* plant produces fruit that reach peak Brix accumulation between three and six days earlier than a fruit obtained from an isogenic plant lacking an earliness trait. In a further aspect, the *Cucumis melo* plant produces fruit that reach peak Brix accumulation between three and five days earlier than a fruit obtained from an isogenic plant lacking an earliness trait. In a further aspect, the *Cucumis melo* plant produces fruit that reach peak Brix accumulation between three and four days earlier than a fruit obtained from an isogenic plant lacking an earliness trait. In a further aspect, the *Cucumis melo* plant produces fruit that reach peak Brix accumulation between four and five days earlier than a fruit obtained from an isogenic plant lacking an earliness trait. In a further aspect, the *Cucumis melo* plant produces fruit that reach peak Brix accumulation between five and six days earlier than a fruit obtained from an isogenic plant lacking an earliness trait.

Flesh color is another hallmark of fruit quality which generally develops late in the maturation process. Red flesh color in melon is a desirable trait in the European Charentais and Italian markets. Furthermore, the presence of the red flesh locus in typically orange flesh varieties (e.g. Harper-type melons) can enhance the color to make it appear more vivid. Deep orange flesh color has been shown in consumer testing to be associated with greater perceived degrees of ripeness and therefore increased consumer preference.

As used herein, "hue angle" or "hue angle measurement" is a measure of fruit color. As used herein, a melon fruit with a flesh hue angle of between 64 and 73° is defined as orange and a melon fruit with a flesh hue angle of between 55 and 63° is defined as red. Hue angle is a calculation derived from the L*a*b color scale and is calculated using a and b with the formula [atan 2(a,b)]. This number is then converted to degrees as the initial formula output result is in radians. The measurements of L*a*b can be slightly different depending on the calculation method of the colorimeter instrument used. In an aspect, observed color of the fruit is quantified colorimetrically using a Konica Minolta colorimeter (e.g. Konica-Minolta® CR-410 Chroma Meter), which gives the L*a*b color scale values as an output reading.

In an aspect, the *Cucumis melo* plant that produces fruit that comprises a red flesh trait linked to an earliness trait on *Cucumis melo* Linkage Group 4 of the Monsanto Consensus Genetic Map is provided. In an aspect, the *Cucumis melo* plant produces fruit that comprises red flesh having a hue angle of less than 63° as determined by using a Konica Minolta colorimeter according to manufacturer's instructions (e.g. Konica-Minolta® CR-410 Chroma Meter). In a further aspect, the *Cucumis melo* plant produces fruit that comprises a hue angle of less than 62°. In a further aspect, the *Cucumis melo* plant produces fruit that comprises a hue angle of less than 61°. In a further aspect, the *Cucumis melo* plant produces fruit that comprises a hue angle of less than 60°. In a further aspect, the *Cucumis melo* plant produces fruit that comprises a hue angle of less than 59°. In a further aspect, the *Cucumis melo* plant produces fruit that comprises a hue angle of less than 58°. In a further aspect, the *Cucumis melo* plant produces fruit that comprises a hue angle of less than 57°. In a further aspect, the *Cucumis melo* plant produces fruit that comprises a hue angle of less than 56°. In a further aspect, the *Cucumis melo* plant produces fruit that comprises a hue angle of less than 63°, less than 62°. In a further aspect, the *Cucumis melo* plant produces fruit that comprises a hue angle of less than 63°, less than 62°, less than 61°, less than 60°, less than 59°, less than 58°, less than 57°, or less than 56°. In an aspect, the *Cucumis melo* plant produces fruit that comprises a hue angle of between 55° and 63°. In a further aspect, the *Cucumis melo* plant produces fruit that comprises a hue angle of between 56° and 62°. In a further aspect, the *Cucumis melo* plant produces fruit that comprises a hue angle of between 57° and 61°. In a further aspect, the *Cucumis melo* plant produces fruit that comprises a hue angle of between 58° and 60°. In a further aspect, the *Cucumis melo* plant produces fruit that comprises a hue angle of between 59° and 60°. In a further aspect, the *Cucumis melo* plant produces fruit that comprises a hue angle of between 55° and 63°, between 56° and 62°, between 57° and 61°, between 58° and 60°, and between 59° and 60°.

In further aspects, the *Cucumis melo* plant with both earliness and red flesh reaches peak Brix accumulation at least 3 days earlier than a *Cucumis melo* plant without an earliness trait. In further aspects, the *Cucumis melo* plant with both earliness and red flesh reaches peak Brix accumulation at least 4 days earlier than a *Cucumis melo* plant without an earliness trait. In further aspects, the *Cucumis melo* plant with both earliness and red flesh reaches peak Brix accumulation at least 5 days earlier than a *Cucumis melo* plant without an earliness trait. In further aspects, the *Cucumis melo* plant with both earliness and red flesh reaches peak Brix accumulation at least 6 days earlier than a *Cucumis melo* plant without an earliness trait.

In an aspect, the *Cucumis melo* plant that produces fruit that comprises a red flesh trait linked to an earliness trait on *Cucumis melo* Linkage Group 4 of the Monsanto Consensus Genetic Map comprises at least 40 parts per million of total carotenes at maturity. In a further aspect, the *Cucumis melo* plant produces fruit that comprises at least 41 parts per million of total carotenes at maturity. In a further aspect, the *Cucumis melo* plant produces fruit that comprises at least 42 parts per million of total carotenes at maturity. In a further aspect, the *Cucumis melo* plant produces fruit that comprises at least 43 parts per million of total carotenes at maturity. In a further aspect, the *Cucumis melo* plant produces fruit that comprises at least 44 parts per million of total carotenes at maturity. In a further aspect, the *Cucumis melo* plant produces fruit that comprises at least 45 parts per million of total carotenes at maturity. In a further aspect, the *Cucumis melo* plant produces fruit that comprises at least 46 parts per million of total carotenes at maturity. In a further aspect, the *Cucumis melo* plant produces fruit that comprises at least 47 parts per million of total carotenes at maturity. In a further aspect, the *Cucumis melo* plant produces fruit that comprises at least 48 parts per million of total carotenes at maturity. In a further aspect, the *Cucumis melo* plant produces fruit that comprises at least 49 parts per million of total carotenes at maturity. In a further aspect, the *Cucumis melo* plant produces fruit that comprises at least 50 parts per million of total carotenes at maturity. In a further aspect, the *Cucumis melo* plant produces fruit that comprises at least 51 parts per million of total carotenes at maturity. In a further aspect, the *Cucumis melo* plant produces fruit that comprises at least 52 parts per million of total carotenes at maturity. In a further aspect, the *Cucumis melo* plant produces fruit that comprises at least 53 parts per million of total carotenes at maturity. In a further aspect, the *Cucumis melo* plant produces fruit that comprises at least 54 parts per million of total carotenes at maturity. In a further aspect, the *Cucumis melo* plant produces fruit that comprises at least 55 parts per million of total carotenes at maturity. In a further aspect, the *Cucumis melo* plant produces fruit that comprises at least 56 parts per million of total carotenes at maturity. In a further aspect, the *Cucumis melo* plant produces fruit that comprises at least 57 parts per million of total carotenes at maturity. In a further aspect, the *Cucumis melo* plant produces fruit that comprises at least 58 parts per million of total carotenes at maturity. In a further aspect, the *Cucumis melo* plant produces fruit that comprises at least 59 parts per million of total carotenes at maturity. In a further aspect, the *Cucumis melo* plant produces fruit that comprises at least 60 parts per million of total carotenes at maturity. In a further aspect, the *Cucumis melo* plant produces fruit that comprises at least 70 parts per million of total carotenes at maturity. In a further aspect, the *Cucumis melo* plant produces fruit that comprises at least 80 parts per million of total carotenes at maturity. In a further aspect, the *Cucumis melo* plant produces fruit that comprises at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 70, or at least 80 parts per million of total carotenes at maturity. In further aspects, the *Cucumis melo* plant with both earliness and red flesh reaches peak Brix accumulation at least 3 days earlier than a *Cucumis melo* plant without an earliness trait. In further aspects, the *Cucumis melo* plant with both earliness and red flesh reaches peak Brix accumulation at least 4 days earlier than a *Cucumis melo* plant without an earliness trait. In further aspects, the *Cucumis melo* plant with both earliness and red flesh reaches peak Brix accumulation at least 5 days earlier than a *Cucumis melo* plant without an earliness trait. In further aspects, the *Cucumis melo* plant with both earliness and red flesh reaches peak Brix accumulation at least 6 days earlier than a *Cucumis melo* plant without an earliness trait.

In an aspect, the *Cucumis melo* plant that produces fruit that comprises a red flesh trait linked to an earliness trait on *Cucumis melo* Linkage Group 4 of the Monsanto Consensus Genetic Map comprises between 40 and 80 parts per million of total carotenes at maturity. In a further aspect, the *Cucumis melo* plant produces fruit that comprises between 42 and 78 parts per million of total carotenes at maturity. In a further aspect, the *Cucumis melo* plant produces fruit that comprises between 44 and 76 parts per million of total carotenes at maturity. In a further aspect, the *Cucumis melo* plant produces fruit that comprises between 48 and 74 parts per million of total carotenes at maturity. In a further aspect, the *Cucumis melo* plant produces fruit that comprises between 50 and 70 parts per million of total carotenes at maturity. In a further aspect, the *Cucumis melo* plant produces fruit that comprises between 52 and 68 parts per million of total carotenes at maturity. In a further aspect, the *Cucumis melo* plant produces fruit that comprises between 54 and 66 parts per million of total carotenes at maturity. In a further aspect, the *Cucumis melo* plant produces fruit that comprises between 56 and 64 parts per million of total carotenes at maturity. In a further aspect, the *Cucumis melo* plant produces fruit that comprises between 58 and 62 parts per million of total carotenes at maturity. In a further aspect, the *Cucumis melo* plant produces fruit that comprises between 40 and 50 parts per million of total carotenes at maturity. In a further aspect, the *Cucumis melo* plant produces fruit that comprises between 40 and 60 parts per million of total carotenes at maturity. In a further aspect, the *Cucumis melo* plant produces fruit that comprises between 40 and 70 parts per million of total carotenes at maturity. In a further aspect, the *Cucumis melo* plant produces fruit that comprises between 40 and 80, between 42 and 78, between 44 and 76, between 46 and 74, between 48 and 72, between 50 and 70, between 52 and 68, between 54 and 66, between 56 and 64, between 58 and 62, between 40 and 50, between 40 and 60, or between 40 and 70, parts per million of total carotenes at maturity. In further aspects, the *Cucumis melo* plant with both earliness and red flesh reaches peak Brix accumulation at least 3 days earlier than a *Cucumis melo* plant without an earliness trait. In further aspects, the *Cucumis melo* plant with both earliness and red flesh reaches peak Brix accumulation at least 4 days earlier than a *Cucumis melo* plant without an earliness trait. In further aspects, the *Cucumis melo* plant with both earliness and red flesh reaches peak Brix accumulation at least 5 days earlier than a *Cucumis melo* plant without an earliness trait. In further aspects, the *Cucumis melo* plant with both earliness and red flesh reaches peak Brix accumulation at least 6 days earlier than a *Cucumis melo* plant without an earliness trait.

As used herein, the term "isogenic" means having the same or a closely similar genotype. Two plants are considered isogenic if their genomes are at least 98% similar in structure and composition. In an aspect, two plants are considered isogenic if their genomes are identical except at a locus or loci of interest. In a further aspect, two plants are considered isogenic if their genomes are identical except at an earliness locus. In a further aspect, two plants are considered isogenic if their genomes are identical except at a red flesh locus. In a further aspect, two plants are considered isogenic if their genomes are identical except at a genomic interval containing an earliness locus linked to a red flesh locus.

In an aspect, the *Cucumis melo* plant that produces fruit that comprises a red flesh trait linked to an earliness trait on *Cucumis melo* Linkage Group 4 of the Monsanto Consensus Genetic Map comprises an amount of total carotenes greater than a mature fruit obtained from an isogenic plant lacking a red flesh phenotype. In a further aspect, the *Cucumis melo* plant produces fruit that comprises an amount of total carotenes greater than a mature fruit obtained from an isogenic plant lacking a homozygous red flesh allele on *Cucumis melo* Linkage Group 4 of the Monsanto Consensus Genetic Map. In a further aspect, the *Cucumis melo* plant produces fruit that comprises greater than 15 parts per million more total carotenes than that of a mature melon fruit from an isogenic plant lacking a red flesh phenotype. In a further aspect, the *Cucumis melo* plant produces fruit that comprises greater than 20 parts per million more total carotenes than that of a mature melon fruit from an isogenic plant lacking a red flesh phenotype. In a further aspect, the *Cucumis melo* plant produces fruit that comprises greater than 25 parts per million more total carotenes than that of a mature melon fruit from an isogenic plant lacking a red flesh phenotype. In a further aspect, the *Cucumis melo* plant produces fruit that comprises greater than 15 parts per million, greater than 20 parts per million, or greater than 25 parts per million more total carotenes than that of a mature melon fruit from an isogenic plant lacking a red flesh phenotype. In an aspect, the *Cucumis melo* plant produces fruit that comprises between 15 and 25 part per million more total carotenes than that of a mature melon fruit from an isogenic plant lacking a red flesh phenotype. In a further aspect, the *Cucumis melo* plant produces fruit that comprises between 15 and 20 part per million more total carotenes than that of a mature melon fruit from an isogenic plant lacking a red flesh phenotype. In further aspects, the *Cucumis melo* plant with both earliness and red flesh reaches peak Brix accumulation at least 3 days earlier than a *Cucumis melo* plant without an earliness trait. In further aspects, the *Cucumis melo* plant with both earliness and red flesh reaches peak Brix accumulation at least 4 days earlier than a *Cucumis melo* plant without an earliness trait. In further aspects, the *Cucumis melo* plant with both earliness and red flesh reaches peak Brix accumulation at least 5 days earlier than a *Cucumis melo* plant without an earliness trait. In further aspects, the *Cucumis melo* plant with both earliness and red flesh reaches peak Brix accumulation at least 6 days earlier than a *Cucumis melo* plant without an earliness trait. In a further aspect, the *Cucumis melo* plant with both earliness and red flesh produces fruit that comprises a hue angle of between 55° and 63°, between 56° and 62°, between 57° and 61°, between 58° and 60°, and between 59° and 60°.

In an aspect, the *Cucumis melo* plant that produces fruit that comprises a red flesh trait linked to an earliness trait on *Cucumis melo* Linkage Group 4 of the Monsanto Consensus Genetic Map comprises greater than 20% more total carotenes than that of a mature melon fruit from an isogenic plant lacking a red flesh phenotype. In a further aspect, the *Cucumis melo* plant produces fruit that comprises greater than 25% more total carotenes than that of a mature melon fruit from an isogenic plant lacking a red flesh phenotype. In a further aspect, the *Cucumis melo* plant produces fruit that comprises greater than 30% more total carotenes than that of a mature melon fruit from an isogenic plant lacking a red flesh phenotype. In a further aspect, the *Cucumis melo* plant produces fruit that comprises greater than 35% more total carotenes than that of a mature melon fruit from an isogenic plant lacking a red flesh phenotype. In a further aspect, the *Cucumis melo* plant produces fruit that comprises greater than 40% more total carotenes than that of a mature melon fruit from an isogenic plant lacking a red flesh phenotype. In a further aspect, the *Cucumis melo* plant produces fruit that comprises greater than 20% more, greater than 25% more, greater than 30% more, greater than 35% more, or greater than 40% more total carotenes than that of a mature melon fruit from an isogenic plant lacking a red flesh phenotype. In an aspect, the *Cucumis melo* plant produces fruit that comprises between 20% and 40% more total carotenes than that of a mature melon fruit from an isogenic plant lacking a red flesh phenotype. In a further aspect, the *Cucumis melo* plant produces fruit that comprises between 25% and 35% more total carotenes than that of a mature melon fruit from an isogenic plant lacking a red flesh phenotype. In a further aspect, the *Cucumis melo* plant produces fruit that comprises between 25% and 30% more total carotenes than that of a mature melon fruit from an isogenic plant lacking a red flesh phenotype. In a further aspect, the *Cucumis melo* plant produces fruit that comprises between 30% and 35% more total carotenes than that of a mature melon fruit from an isogenic plant lacking a red flesh phenotype. In a further aspect, the *Cucumis melo* plant produces fruit that comprises between 20% and 40% more, between 25% and 35% more, between 25% and 30% more, or between 30% and 35% more total carotenes than that of a mature melon fruit from an isogenic plant lacking a red flesh phenotype. In further aspects, the *Cucumis melo* plant with both earliness and red flesh reaches peak Brix accumulation at least 3 days earlier than a *Cucumis melo* plant without an earliness trait. In further aspects, the *Cucumis melo* plant with both earliness and red flesh reaches peak Brix accumulation at least 4 days earlier than a *Cucumis melo* plant without an earliness trait. In further aspects, the *Cucumis melo* plant with both earliness and red flesh reaches peak Brix accumulation at least 5 days earlier than a *Cucumis melo* plant without an earliness trait. In further aspects, the *Cucumis melo* plant with both earliness and red flesh reaches peak Brix accumulation at least 6 days earlier than a *Cucumis melo* plant without an earliness trait.

In an aspect, the *Cucumis melo* plant that produces fruit that comprises a red flesh trait linked to an earliness trait on *Cucumis melo* Linkage Group 4 of the Monsanto Consensus Genetic Map produces fruit that reaches maturity earlier than a fruit obtained from an isogenic plant lacking an earliness trait. In a further aspect, the *Cucumis melo* plant produces fruit that reaches maturity earlier than a fruit obtained from an isogenic plant lacking an earliness allele. In an aspect, the *Cucumis melo* plant that produces fruit that comprises a red flesh trait linked to an earliness trait on *Cucumis melo* Linkage Group 4 of the Monsanto Consensus Genetic Map produces mature melon fruit with an average maximum Brix content at least 1° Brix greater than a mature melon fruit of an isogenic plant without an earliness trait.

In an aspect, the *Cucumis melo* plant that produces fruit that comprises a red flesh trait linked to an earliness trait on *Cucumis melo* Linkage Group 4 of the Monsanto Consensus Genetic Map produces melon fruit with an average Brix content of at least 9° Brix at fruit maturity. In an aspect, the *Cucumis melo* plant produces fruit with an average Brix content of at least 10° Brix at fruit maturity. In an aspect, the *Cucumis melo* plant produces fruit with an average Brix content of at least 11° Brix at fruit maturity. In an aspect, the *Cucumis melo* plant produces fruit with an average Brix content of at least 12° Brix at fruit maturity. In an aspect, the *Cucumis melo* plant produces fruit with an average Brix content of at least 13° Brix at fruit maturity. In an aspect, the *Cucumis melo* plant produces fruit with an average Brix content of at least 14° Brix at fruit maturity. In an aspect, the *Cucumis melo* plant produces fruit with an average Brix content of at least 15° Brix at fruit maturity. In a further aspect, the *Cucumis melo* plant produces fruit with an average Brix content between 9° and 10° Brix at fruit maturity. In a further aspect, the *Cucumis melo* plant produces fruit with an average Brix content between 9° and 11°. In a further aspect, the *Cucumis melo* plant produces fruit with an average Brix content between 9° and 12° Brix at fruit maturity. In a further aspect, the *Cucumis melo* plant produces fruit with an average Brix content between 9° and 13° Brix at fruit maturity. In a further aspect, the *Cucumis melo* plant produces fruit with an average Brix content between 9° and 14° Brix at fruit maturity. In a further aspect, the *Cucumis melo* plant produces fruit with an average Brix content between 9° and 15° Brix at fruit maturity. In a further aspect, the *Cucumis melo* plant produces fruit with an average Brix content of at least 9° Brix, at least 10° Brix, at least 11° Brix, at least 12° Brix, at least 13° Brix, at least 14° Brix, or at least 15° Brix at fruit maturity. In a further aspect, the *Cucumis melo* plant with both earliness and red flesh produces fruit that comprises a hue angle of between 55° and 63°, between 56° and 62°, between 57° and 61°, between 58° and 60°, and between 59° and 60°.

As used herein, the terms "coupled", "coupled loci" or "coupling event" refers to a genetic condition in which the alleles of two different loci occur together on one chromosome. In a further aspect, two different loci that are coupled occur within about 20 cM, 19 cM, 18 cM, 17 cM, 16 cM, 15 cM, 14 cM, 13 cM, 12 cM, 11 cM, 10 cM, 9 cM, 8 cM, 7 cM, 6 cM, 5 cM, 4 cM, 3 cM, 2 cM, 1 cM, 0.5 cM, or less than 0.5 cM from each other.

As used herein, "co-segregates" means inherited together during meiosis more often than random assortment would predict. In example, during meiosis in the course of plant breeding, two marker alleles or two phenotypes or a marker allele and a phenotype that are inherited together in the same progeny are said to co-segregate. This typically means that the two marker alleles, two phenotypes, or marker allele and phenotype are linked. For example, two genes coupled on the same chromosome will be inherited together and therefore co-segregate. A marker allele that is linked to a phenotype will tend to co-segregate with that phenotype.

As used herein, "flanking", "flanking markers", or an "interval flanked by" is used to describe the boundaries of a chromosome interval or region by designated genetic markers. As used herein, flanking markers designating the boundaries of a given region are included within that region.

As used herein, the term "chromosome interval" designates a contiguous linear span of genomic DNA that resides on a single chromosome.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. A "gene locus" is a specific chromosome location in the genome of a species where a specific gene can be found. A "trait locus" is a specific chromosome location in the genome of a species where a gene conferring a specific trait can be found. In an aspect of the present disclosure, a trait locus for red flesh or a red flesh locus corresponds to the location in the genome where a gene conferring a red flesh trait can be found and a trait locus for earliness or an earliness locus corresponds to the location in the genome where a gene conferring an earliness trait can be found. In a further aspect, trait locus for red flesh and a trait locus for earliness are linked and located on *Cucumis melo* Linkage Group 6 of the ICuGI Public Consensus Genetic Map.

As used herein, "allele" refers to an alternative nucleic acid sequence at a further locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population.

As used herein, the terms "recombinant" or "recombination event" refers to a plant having a new genetic make-up arising as a result of crossing over between homologous chromosomes during meiosis.

In an aspect, the chromosomal region on Linkage Group 4 of the Monsanto Consensus Genetic Map linked with earliness comprises the earliness locus found in *Cucumis melo* line "BEST", a sample of seed of *Cucumis melo* line "BEST" having been deposited under ATCC Accession Number PTA-12263. The *Cucumis melo* line "BEST" is disclosed in U.S. Pat. No. 9,580,724, which is hereby incorporated by reference in its entirety. In a further aspect, an earliness locus on Linkage Group 4 of the Monsanto Consensus Genetic Map is flanked by the markers NU0243432 (physical map position 28,346,029 basepairs) and NU0220305 (physical map position 24,876,456 basepairs). In certain aspects, a genetic marker linked to and useful in molecular detection of the earliness locus is selected from the group consisting of NU0219671, NU0243432, NU0243324, NU0219095, NU0218257, NU0219354, NU0219672, NU0219274, NU0243607, NU0219118, NU0220372, NU0220305, and NU0220446.

In an aspect, an earliness trait segregating with an earliness locus located on *Cucumis melo* Linkage Group 4 of the Monsanto Consensus Genetic Map is obtainable from lines and varieties provided in this application such as "BEST", CHA-192-ONTARIO-AN/BEST, the "earliness event", and CHA-ZA15-0014AN. Sources of earliness on *Cucumis melo* Linkage Group 4 of the Monsanto Consensus Genetic Map are known in the art such as Q3-2-2-2 described in Cuevas et al. 2009 (A consensus linkage map identifies genomic regions controlling fruit maturity and beta-carotene-associated flesh color in melon (*Cucumis melo* L.). *Theor Appl Genet.* August; 119(4):741-56, 2009, "Cuevas"). The line Q3-2-2-2 is described as having no β-carotene and a white flesh. The earliness QTL in Q3-2-2-2 was mapped to approximately 50.3 cM on Linkage Group 4 of the Monsanto Consensus Genetic Map (It is noted that Linkage Group 4 of the Monsanto Consensus Genetic Map as used here is equivalent to Linkage Group 6 of the ICuCI public map, See Table 2). Additionally, Monforte et al. (Identification of quantitative trait loci involved in fruit quality traits in melon (*Cucumis melo* L.). *Theor Appl Genet*. February; 108:750-758, 2004, "Monforte"), discloses an earliness QTL that is associated with a 50 cM region on Linkage Group 4 of the Monsanto Consensus Genetic Map. Cuevas suggests that breeding an early melon with high β-carotene could be difficult because of the complex genetics involved in producing these traits. Cuevas further suggests that breeding early fruit maturity and high β-carotene traits should involve introgression of the β-carotene QTL on Linkage Group 9 (QTL β-carM/E.9.1). Cuevas specifically notes that the amount of variation from a β-car QTL on Linkage Group 4 of the Monsanto Consensus Genetic Map (β-carM/E.6.1) is low.

In an aspect, the chromosomal region on Linkage Group 4 of the Monsanto Consensus Genetic Map linked with red flesh comprises a red flesh locus found in *Cucumis* melo line CHA-192-0058-MO. In a further aspect, the red flesh locus on Linkage Group 4 of the Monsanto Consensus Genetic Map in flanked by the markers NU0220305 (map position 24,876,456 basepairs) and NCMEL008579265 (map position 22,825,883 basepairs). In certain aspects, the genetic marker linked to and useful in molecular detection of the red flesh locus is selected from the group consisting of NU0220305, NU0220372, NU0219774, NCMEL009758372, NU0219889, NU0244419, NU0244478, NU0220446, NU0219650, NU0244718, NU0218943, NCMEL008579265, NU0219136, NU0243542, NU0219676, and NU0243281.

In a further aspect, the red flesh trait segregating with a red flesh locus located on *Cucumis melo* Linkage Group 4 of the Monsanto Consensus Genetic Map is obtainable from lines and varieties provided in this application such as CHA-192-0058-MO, CHA-192-0034-AN, ITAAZ11-7001MO, and CHA-ZA15-0014AN. A source of red flesh is known in the art as Nunhem's variety 'Magenta' (Nunhem's USA, Inc). Causative genetic elements for the red flesh phenotype in Nunhem's variety 'Magenta' have not been disclosed. Three QTL are disclosed in Harel-Beja et al. that are located on *Cucumis melo* Linkage Group 4 of the Monsanto Consensus Genetic Map (Linkage Group 6 on the ICuGI public map, See Table 2) and associated with orange flesh color, β-carotene, and total carotenoids (A genetic map of melon highly enriched with fruit quality QTLs and EST markers, including sugar and carotenoid metabolism genes. *Theor Appl Genet*. August; 121:511-533, 2010, "Harel-Beja"). The orange flesh color and β-carotene QTLs on Linkage Group 4 of the Monsanto Consensus Genetic Map are also found in Cuevas and Monforte. Harel-Beja maps the QTL associated with orange flesh color, β-carotene, and total carotenoid to approximately 88 to 90 cM on Linkage Group 4 of the Monsanto Consensus Genetic Map. The red flesh QTL disclosed herein maps to approximately 50 cM suggesting at least two flesh color QTL on Linkage Group 4 of the Monsanto Consensus Genetic Map. Cuevas further suggests that breeding early fruit maturity and high β-carotene should use the β-carotene QTL on Linkage Group 9 (QTL β-carM/E.9.1). Cuevas specifically notes that the amount of variation from a β-car QTL on Linkage Group 4 of the Monsanto Consensus Genetic Map (β-carM/E.6.1) is low. An early, red flesh *Cucumis melo* line is not disclosed in the art.

In an aspect, this application provides a *Cucumis melo* plant, or part thereof, wherein a fruit obtained from the *Cucumis melo* plant comprises a red flesh trait linked to an earliness trait on *Cucumis melo* Linkage Group 4 of the Monsanto Consensus Genetic Map. In a further aspect, the *Cucumis melo* plant with a red flesh trait linked to an earliness trait is *Cucumis melo* cultivar CHA-ZA15-0014AN. In a further aspect, a chromosomal region segregating with a red flesh trait linked to an earliness trait comprising a red flesh locus linked to an earliness locus is obtainable from *Cucumis melo* cultivar CHA-ZA15-0014AN. In a further aspect, this application provides the *Cucumis melo* seed capable of producing *Cucumis melo* cultivar CHA-ZA15-0014AN. A sample seed of *Cucumis melo* line CHA-ZA15-0014AN is deposited under ATCC Accession Number PTA-124202. In an aspect, the *Cucumis melo* plant that comprises a red flesh trait linked to an earliness trait on *Cucumis melo* Linkage Group 4 of the Monsanto Consensus Genetic Map comprises the earliness locus found in *Cucumis melo* line "BEST" linked to the red flesh locus found in *Cucumis melo* line CHA-192-0058-MO.

In an aspect, the *Cucumis melo* plant that produces fruit that comprises a red flesh trait linked to an earliness trait on *Cucumis melo* Linkage Group 4 of the Monsanto Consensus Genetic Map provided in this application is obtainable by crossing a first parent *Cucumis melo* plant that comprises at least one red flesh allele linked to at least one earliness allele on *Cucumis melo* Linkage Group 4 of the Monsanto Consensus Genetic Map to a second parent *Cucumis melo* plant without a red flesh allele or an earliness allele on *Cucumis melo* Linkage Group 4 of the Monsanto Consensus Genetic Map, selecting a $F_1$ progeny plant that comprises a G nucleotide at marker NU0243432 linked to a C nucleotide at marker NU0220305 linked to a T nucleotide at marker NCMEL009758372 linked to a T nucleotide at marker NCMEL008579265, selfing the selected $F_1$ progeny plant, and selecting a $F_2$ progeny plant that comprises a homozygous G nucleotide, "GG", at marker NU0243432, a homozygous C nucleotide, "CC", at marker NU0220305, a homozygous T nucleotide, "TT", at marker NCMEL009758372 and a homozygous T nucleotide, "TT", at marker NCMEL008579265. In a further aspect, a $F_1$ progeny plant can be selected that comprises a G nucleotide at marker NU0243432 linked to a T nucleotide at marker NCMEL008579265. In a further aspect, a $F_1$ progeny plant can be selected that comprises a G nucleotide at marker NU0243432 linked to a T nucleotide at marker NCMEL009758372. In a further aspect, a $F_1$ progeny plant can be selected that comprises a C nucleotide at marker NU0220305 linked to a T nucleotide at marker NCMEL008579265. In a further aspect, a $F_1$ progeny plant can be selected that comprises a C nucleotide at marker NU0220305 linked to a T nucleotide at marker NCMEL009758372. In a further aspect, a first parent *Cucumis melo* plant that comprises at least one red flesh allele linked to at least one earliness allele on *Cucumis melo* Linkage Group 4 of the Monsanto Consensus Genetic Map is *Cucumis melo* line CHA-ZA15-0014AN. In a further aspect, a second parent *Cucumis melo* plant without a red flesh allele or an earliness allele on *Cucumis melo* Linkage Group 4 of the Monsanto Consensus Genetic Map can be a wild-type plant selected from the group consisting of *Cucumis melo melo*, *Cucumis melo agrestis*, *Cucumis melo cantalupo*, *Cucumis melo conomon*, *Cucumis melo inodorus*, *Cucumis melo texanus*, *Cucumis melo dudaim*, *Cucumis melo flexuosus*, and *Cucumis melo momordica*. In a further aspect, the selected $F_1$ progeny plant can be crossed to a *Cucumis melo* plant that comprises at least one red flesh allele linked to an earliness allele on *Cucumis melo* Linkage Group 4 of the Monsanto Consensus Genetic Map. In a further aspect, the selected $F_1$ progeny plant can be crossed to the *Cucumis melo* plant CHA-ZA15-0014AN.

In an aspect, the *Cucumis melo* plant that produces fruit that comprises a red flesh trait linked to an earliness trait on *Cucumis melo* Linkage Group 4 of the Monsanto Consensus Genetic Map provided in this application is obtainable by crossing a first parent *Cucumis melo* plant that comprises a homozygous red flesh allele without an earliness allele on *Cucumis melo* Linkage Group 4 of the Monsanto Consensus Genetic Map to a second parent *Cucumis melo* plant with a homozygous earliness allele without a red flesh allele on *Cucumis melo* Linkage Group 4 of the Monsanto Consensus Genetic Map, selecting a recombinant $F_1$ progeny plant that comprises a G nucleotide at marker NU0243432 linked to a C nucleotide at marker NU0220305 linked to a T nucleotide at marker NCMEL009758372 linked to a T nucleotide at marker NCMEL008579265, selfing the selected $F_1$ progeny plant, and selecting a $F_2$ progeny plant that comprises a homozygous G nucleotide, "GG", at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In a further aspect, a recombinant $F_1$ progeny plant can be selected that comprises a G nucleotide at marker NU0243432 linked to a T nucleotide at marker NCMEL008579265. In a further aspect, a $F_1$ progeny plant can be selected that comprises a G nucleotide at marker NU0243432 linked to a T nucleotide at marker NCMEL009758372. In a further aspect, a $F_1$ progeny plant can be selected that comprises a C nucleotide at marker NU0220305 linked to a T nucleotide at marker NCMEL008579265. In a further aspect, a $F_1$ progeny plant can be selected that comprises a C nucleotide at marker NU0220305 linked to a T nucleotide at marker NCMEL009758372. In a further aspect, the first parent *Cucumis melo* plant is *Cucumis melo* line *Cucumis melo* line CHA-192-0058-MO. In a further aspect, the second parent *Cucumis melo* plant is *Cucumis melo* line "BEST", or the *Cucumis melo* line "earliness event".

In an aspect, the *Cucumis melo* plant that produces fruit that comprises a red flesh trait linked to an earliness trait on *Cucumis melo* Linkage Group 4 of the Monsanto Consensus Genetic Map provided in this application is obtainable by crossing two parent *Cucumis melo* plants that both comprise at least one red flesh allele and at least one earliness allele that are unlinked on *Cucumis melo* Linkage Group 4 of the Monsanto Consensus Genetic Map, selecting a recombinant $F_1$ progeny plant that comprises a G nucleotide at marker NU0243432 linked to a C nucleotide at marker NU0220305 linked to a T nucleotide at marker NCMEL009758372 linked to a T nucleotide at marker NCMEL008579265, selfing the selected $F_1$ progeny plant, and selecting a $F_2$ progeny plant that comprises a homozygous G nucleotide, "GG", at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In a further aspect, a recombinant $F_1$ progeny plant can be selected that comprises a G nucleotide at marker NU0243432 linked to a T nucleotide at marker NCMEL008579265. In a further aspect, a $F_1$ progeny plant can be selected that comprises a G nucleotide at marker NU0243432 linked to a T nucleotide at marker NCMEL009758372. In a further aspect, a $F_1$ progeny plant can be selected that comprises a C nucleotide at marker NU0220305 linked to a T nucleotide at marker NCMEL008579265. In a further aspect, a $F_1$ progeny plant can be selected that comprises a C nucleotide at marker NU0220305 linked to a T nucleotide at marker NCMEL009758372.

In an aspect, the present application provides a *Cucumis melo* plant comprising at least an introgressed chromosomal region on Linkage Group 4 of the Monsanto Consensus Genetic Map segregating with red flesh and earliness in melon fruits relative to a plant lacking the region, wherein the region comprises an earliness locus located within flanking markers NU0243432 and NU0220305 and a red flesh locus located within flanking markers NU0220305 and NCMEL008579265. In a further aspect, the *Cucumis melo* plant with both earliness and red flesh co-segregate with a homozygous G nucleotide, "GG", at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In a further aspect, the *Cucumis melo* plant with both earliness and red flesh co-segregate with a homozygous G nucleotide, "GG", at marker NU0243432, a homozygous C nucleotide, "CC", at marker NU0220305, and a homozygous T nucleotide, "TT", at marker NCMEL008579265. In a further aspect, the *Cucumis melo* plant with both earliness and red flesh co-segregate with a homozygous G nucleotide, "GG", at marker NU0243432, a homozygous C nucleotide, "CC", at marker NU0220305, and a homozygous T nucleotide, "TT", at marker NCMEL009758372. In a further aspect, the *Cucumis melo* plant with both earliness and red flesh co-segregate with a homozygous G nucleotide, "GG", at marker NU0243432, a heterozygous C nucleotide at marker NU0220305, a homozygous T nucleotide, "TT", at marker NCMEL009758372, and a homozygous T nucleotide, "TT", at marker NCMEL008579265. In a further aspect, the *Cucumis melo* plant with both earliness and red flesh co-segregate with a homozygous G nucleotide, "GG", at marker NU0243432, a heterozygous C nucleotide at marker NU0220305, and a homozygous T nucleotide, "TT", at marker NCMEL008579265. In a further aspect, the *Cucumis melo* plant with both earliness and red flesh co-segregate with a homozygous G nucleotide, "GG", at marker NU0243432, a heterozygous C nucleotide at marker NU0220305, and a homozygous T nucleotide, "TT", at marker NCMEL009758372. In a further aspect, the *Cucumis melo* plant with both earliness and red flesh co-segregate with a heterozygous G nucleotide at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In a further aspect, the *Cucumis melo* plant with both earliness and red flesh co-segregate with a heterozygous G nucleotide at marker NU0243432, a homozygous C nucleotide, "CC", at marker NU0220305, and a homozygous T nucleotide, "TT", at marker NCMEL008579265. In a further aspect, the *Cucumis melo* plant with both earliness and red flesh co-segregate with a heterozygous G nucleotide at marker NU0243432, a homozygous C nucleotide, "CC", at marker NU0220305, and a homozygous T nucleotide, "TT", at marker NCMEL009758372. In a further aspect, the *Cucumis melo* plant with both earliness and red flesh co-segregate with a heterozygous G nucleotide at marker NU0243432, a heterozygous C nucleotide at marker NU0220305, a homozygous T nucleotide, "TT", at marker NCMEL009758372, and a homozygous T nucleotide, "TT", at marker NCMEL008579265. In a further aspect, the *Cucumis melo* plant with both earliness and red flesh co-segregate with a heterozygous G nucleotide at marker NU0243432, a heterozygous C nucleotide at marker NU0220305, and a homozygous T nucleotide, "TT", at marker NCMEL008579265. In a further aspect, the *Cucumis melo* plant with both earliness and red flesh co-segregate with a heterozygous G nucleotide at marker NU0243432, a heterozygous C nucleotide at marker NU0220305, and a homozygous T nucleotide, "TT", at marker NCMEL009758372. In a further aspect, the *Cucumis melo* plant with both earliness and red flesh co-segregate with a homozygous G nucleotide, "GG", at marker NU0243432, a homozygous T nucleotide, "TT", at marker NCMEL009758372, and a homozygous T nucleotide, "TT", at marker NCMEL008579265. In a further aspect, the *Cucumis melo* plant with both earliness and red flesh co-segregate with a homozygous G nucleotide, "GG", at marker NU0243432 and a homozygous T nucleotide, "TT", at marker NCMEL008579265. In a further aspect, the *Cucumis melo* plant with both earliness and red flesh co-segregate with a homozygous G nucleotide, "GG", at marker NU0243432 and a homozygous T nucleotide, "TT", at marker NCMEL009758372. In a further aspect, the *Cucumis melo* plant with both earliness and red flesh co-segregate with a heterozygous G nucleotide at marker NU0243432, a homozygous T nucleotide, "TT", at marker NCMEL009758372, and a homozygous T nucleotide, "TT", at marker NCMEL008579265. In a further aspect, the *Cucumis melo* plant with both earliness and red flesh co-segregate with a heterozygous G nucleotide at marker NU0243432 and a homozygous T nucleotide, "TT", at marker NCMEL008579265. In a further aspect, the *Cucumis melo* plant with both earliness and red flesh co-segregate with a heterozygous G nucleotide at marker NU0243432 and a homozygous T nucleotide, "TT", at marker NCMEL009758372. In a further aspect, the *Cucumis melo* plant with both earliness and red flesh co-segregate with a homozygous C nucleotide, "CC", at marker NU0220305, a homozygous T nucleotide, "TT", at marker NCMEL009758372, and a homozygous T nucleotide, "TT", at marker NCMEL008579265. In a further aspect, the *Cucumis melo* plant with both earliness and red flesh co-segregate with a homozygous C nucleotide, "CC", at marker NU0220305, and a homozygous T nucleotide, "TT", at marker NCMEL008579265. In a further aspect, the *Cucumis melo* plant with both earliness and red flesh co-segregate with a homozygous C nucleotide, "CC", at marker NU0220305, and a homozygous T nucleotide, "TT", at marker NCMEL009758372. In a further aspect, the *Cucumis melo* plant with both earliness and red flesh co-segregate with a heterozygous C nucleotide at marker NU0220305, a homozygous T nucleotide, "TT", at marker NCMEL009758372, and a homozygous T nucleotide, "TT", at marker NCMEL008579265. In a further aspect, the *Cucumis melo* plant with both earliness and red flesh co-segregate with a heterozygous C nucleotide at marker NU0220305 and a homozygous T nucleotide, "TT", at marker NCMEL008579265. In a further aspect, the *Cucumis melo* plant with both earliness and red flesh co-segregate with a heterozygous C nucleotide at marker NU0220305 and a homozygous T nucleotide, "TT", at marker NCMEL009758372. In a further aspect, the *Cucumis melo* plant with both earliness and red flesh co-segregate with a homozygous G nucleotide, "GG", at marker NU0243432. In a further aspect, the *Cucumis melo* plant with both earliness and red flesh co-segregate with a heterozygous G nucleotide at marker NU0243432. In a further aspect, the *Cucumis melo* plant with both earliness and red flesh co-segregate with a homozygous C nucleotide, "CC", at marker NU0220305. In a further aspect, the *Cucumis melo* plant with both earliness and red flesh co-segregate with a heterozygous C nucleotide, at marker NU0220305. In a further aspect, the *Cucumis melo* plant with both earliness and red flesh co-segregate with a homozygous T nucleotide, "TT", at marker NCMEL009758372. In a further aspect, the *Cucumis melo* plant with both earliness and red flesh co-segregate with a homozygous T nucleotide, "TT", at marker NCMEL008579265. In further aspects, the *Cucumis melo* plant with both earliness and red flesh comprises flesh with a hue angle between 55° and 63°. In further aspects, the *Cucumis melo* plant with both earliness and red flesh reaches peak Brix accumulation at least 3 days earlier than a *Cucumis melo* plant without an earliness trait. In further aspects, the *Cucumis melo* plant with both earliness and red flesh reaches peak Brix accumulation at least 4 days earlier than a *Cucumis melo* plant without an earliness trait. In further aspects, the *Cucumis melo* plant with both earliness and red flesh reaches peak Brix accumulation at least 5 days earlier than a *Cucumis melo* plant without an earliness trait. In further aspects, the *Cucumis melo* plant with both earliness and red flesh reaches peak Brix accumulation at least 6 days earlier than a *Cucumis melo* plant without an earliness trait. In some aspects, genetic assays of the *Cucumis melo* plant comprise PCR, single strand conformational polymorphism analysis, denaturing gradient gel electrophoresis, cleavage fragment length polymorphism analysis, TAQMAN assay, or DNA sequencing.

In an aspect, this application provides a *Cucumis melo* plant that produces fruit that comprises a red flesh trait linked to an earliness trait on *Cucumis melo* Linkage Group 4 of the Monsanto Consensus Genetic Map. In a further aspect, this application provides a *Cucumis melo* plant that comprises a homozygous marker allele on *Cucumis melo* Linkage Group 4 of the Monsanto Consensus Genetic Map linked to a red flesh locus. In further aspects, the red flesh trait co-segregates with a homozygous marker allele at one genetic marker located on *Cucumis melo* Linkage Group 4 of the Monsanto Consensus Genetic Map linked to a red flesh locus. In further aspects, the red flesh trait co-segregates with a homozygous marker allele at more than one genetic marker located on *Cucumis melo* Linkage Group 4 of the Monsanto Consensus Genetic Map linked to a red flesh locus. In further aspects, the red flesh trait co-segregates with a homozygous G nucleotide, "GG", at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In further aspects, the red flesh trait co-segregates with a homozygous G nucleotide, "GG", at marker NU0243432, a homozygous C nucleotide, "CC", at marker NU0220305, and a homozygous T nucleotide, "TT", at marker NCMEL008579265. In a further aspect, the *Cucumis melo* plant with both earliness and red flesh co-segregate with a homozygous G nucleotide, "GG", at marker NU0243432, a homozygous C nucleotide, "CC", at marker NU0220305, and a homozygous T nucleotide, "TT", at marker NCMEL009758372. In further aspects, the red flesh trait co-segregates with a homozygous G nucleotide, "GG", at marker NU0243432, a heterozygous C nucleotide at marker NU0220305, a homozygous T nucleotide, "TT", at marker NCMEL009758372, and a homozygous T nucleotide, "TT", at marker NCMEL008579265. In further aspects, the red flesh trait co-segregates with a homozygous G nucleotide, "GG", at marker NU0243432, a heterozygous C nucleotide at marker NU0220305, and a homozygous T nucleotide, "TT", at marker NCMEL008579265. In further aspects, the red flesh trait co-segregates with a homozygous G nucleotide, "GG", at marker NU0243432, a heterozygous C nucleotide at marker NU0220305, and a homozygous T nucleotide, "TT", at marker NCMEL009758372. In further aspects, the red flesh trait co-segregates with a heterozygous G nucleotide at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In further aspects, the red flesh trait co-segregates with a heterozygous G nucleotide at marker NU0243432, a homozygous C nucleotide, "CC", at marker NU0220305, and a homozygous T nucleotide, "TT", at marker NCMEL008579265. In further aspects, the red flesh trait co-segregates with a heterozygous G nucleotide at marker NU0243432, a homozygous C nucleotide, "CC", at marker NU0220305, and a homozygous T nucleotide, "TT", at marker NCMEL009758372. In further aspects, the red flesh trait co-segregates with a heterozygous G nucleotide at marker NU0243432, a heterozygous C nucleotide at marker NU0220305, a homozygous T nucleotide, "TT", at marker NCMEL009758372, and a homozygous T nucleotide, "TT", at marker NCMEL008579265. In further aspects, the red flesh trait co-segregates with a heterozygous G nucleotide at marker NU0243432, a heterozygous C nucleotide at marker NU0220305, and a homozygous T nucleotide, "TT", at marker NCMEL008579265. In further aspects, the red flesh trait co-segregates with a heterozygous G nucleotide at marker NU0243432, a heterozygous C nucleotide at marker NU0220305, and a homozygous T nucleotide, "TT", at marker NCMEL009758372. In further aspects, the red flesh trait co-segregates with a homozygous G nucleotide, "GG", at marker NU0243432, a homozygous T nucleotide, "TT", at marker NCMEL009758372, and a homozygous T nucleotide, "TT", at marker NCMEL008579265. In further aspects, the red flesh trait co-segregates with a homozygous G nucleotide, "GG", at marker NU0243432 and a homozygous T nucleotide, "TT", at marker NCMEL008579265. In further aspects, the red flesh trait co-segregates with a homozygous G nucleotide, "GG", at marker NU0243432 and a homozygous T nucleotide, "TT", at marker NCMEL009758372. In further aspects, the red flesh trait co-segregates with a heterozygous G nucleotide at marker NU0243432, a homozygous T nucleotide, "TT", at marker NCMEL009758372, and a homozygous T nucleotide, "TT", at marker NCMEL008579265. In further aspects, the red flesh trait co-segregates with a heterozygous G nucleotide at marker NU0243432 and a homozygous T nucleotide, "TT", at marker NCMEL008579265. In further aspects, the red flesh trait co-segregates with a heterozygous G nucleotide at marker NU0243432 and a homozygous T nucleotide, "TT", at marker NCMEL009758372. In further aspects, the red flesh trait co-segregates with a homozygous C nucleotide, "CC", at marker NU0220305, a homozygous T nucleotide, "TT", at marker NCMEL009758372, and a homozygous T nucleotide, "TT", at marker NCMEL008579265. In further aspects, the red flesh trait co-segregates with a homozygous C nucleotide, "CC", at marker NU0220305, and a homozygous T nucleotide, "TT", at marker NCMEL008579265. In further aspects, the red flesh trait co-segregates with a homozygous C nucleotide, "CC", at marker NU0220305, and a homozygous T nucleotide, "TT", at marker NCMEL009758372. In further aspects, the red flesh trait co-segregates with a heterozygous C nucleotide at marker NU0220305, a homozygous T nucleotide, "TT", at marker NCMEL009758372, and a homozygous T nucleotide, "TT", at marker NCMEL008579265. In further aspects, the red flesh trait co-segregates with a heterozygous C nucleotide at marker NU0220305 and a homozygous T nucleotide, "TT", at marker NCMEL008579265. In further aspects, the red flesh trait co-segregates with a heterozygous C nucleotide at marker NU0220305 and a homozygous T nucleotide, "TT", at marker NCMEL009758372. In further aspects, the red flesh trait co-segregates with a homozygous G nucleotide, "GG", at marker NU0243432. In a further aspect, the Cucumis melo plant with both earliness and red flesh co-segregate with a heterozygous G nucleotide at marker NU0243432. In further aspects, the red flesh trait co-segregates with a homozygous C nucleotide, "CC", at marker NU0220305. In further aspects, the red flesh trait co-segregates with a heterozygous C nucleotide, at marker NU0220305. In further aspects, the red flesh trait co-segregates with a homozygous T nucleotide, "TT", at marker NCMEL009758372. In further aspects, the Cucumis melo plant with both earliness and red flesh comprises flesh with a hue angle between 55° and 63°. In further aspects, the Cucumis melo plant with both earliness and red flesh reaches peak Brix accumulation at least 3 days earlier than a Cucumis melo plant without an earliness trait. In further aspects, the Cucumis melo plant with both earliness and red flesh reaches peak Brix accumulation at least 4 days earlier than a Cucumis melo plant without an earliness trait. In further aspects, the Cucumis melo plant with both earliness and red flesh reaches peak Brix accumulation at least 5 days earlier than a Cucumis melo plant without an earliness trait. In further aspects, the Cucumis melo plant with both earliness and red flesh reaches peak Brix accumulation at least 6 days earlier than a Cucumis melo plant without an earliness trait. In further aspects, the red flesh trait co-segregates with a homozygous T nucleotide, "TT", at marker NCMEL008579265. In some aspects, genetic assays of the Cucumis melo plant comprise PCR, single strand conformational polymorphism analysis, denaturing gradient gel electrophoresis, cleavage fragment length polymorphism analysis, TAQMAN assay, or DNA sequencing.

In an aspect, this application provides a Cucumis melo plant that produces fruit that comprises a red flesh trait linked to an earliness trait on Cucumis melo Linkage Group 4 of the Monsanto Consensus Genetic Map. In a further aspect, the red flesh trait co-segregates with at least one earliness-associated allele at one genetic marker located on Cucumis melo Linkage Group 4 of the Monsanto Consensus Genetic Map. In further aspects, the red flesh trait co-segregates with a heterozygous earliness-associated allele at one genetic marker located on Cucumis melo Linkage Group 4 of the Monsanto Consensus Genetic Map. In further aspects, the red flesh trait co-segregates with a homozygous earliness-associated allele at one genetic marker located on Cucumis melo Linkage Group 4 of the Monsanto Consensus Genetic Map. In further aspects, the red flesh trait co-segregates with a heterozygous earliness-associated allele at more than one genetic marker located on Cucumis melo Linkage Group 4 of the Monsanto Consensus Genetic Map. In further aspects, the red flesh trait co-segregates with a homozygous earliness-associated allele at more than one genetic marker located on Cucumis melo Linkage Group 4 of the Monsanto Consensus Genetic Map. In further aspects, the red flesh trait co-segregates with "GG" at marker NU0243432. In further aspects, the red flesh trait co-segregates with "CC" at marker NU0220305. In further aspects, the red flesh trait co-segregates with a G nucleotide at flanking marker NU0243432. In further aspects, the red flesh trait co-segregates with a C nucleotide at flanking marker NU0220305. In some aspects, genetic assays of the Cucumis melo plant comprise PCR, single strand conformational polymorphism analysis, denaturing gradient gel electrophoresis, cleavage fragment length polymorphism analysis, TAQMAN assay, or DNA sequencing.

In an aspect, this application provides a *Cucumis melo* plant that produces fruit that comprises a red flesh trait linked to an earliness trait on *Cucumis melo* Linkage Group 4 of the Monsanto Consensus Genetic Map. In further aspects, the earliness trait co-segregates with at least one earliness allele at one genetic marker located on *Cucumis melo* Linkage Group 4 of the Monsanto Consensus Genetic Map. In further aspects, the earliness trait co-segregates with a heterozygous earliness allele at one genetic marker located on *Cucumis melo* Linkage Group 4 of the Monsanto Consensus Genetic Map. In further aspects, the earliness trait co-segregates with a homozygous earliness allele at one genetic marker located on *Cucumis melo* Linkage Group 4 of the Monsanto Consensus Genetic Map. In further aspects, the earliness trait co-segregates with a heterozygous earliness allele at more than one genetic marker located on *Cucumis melo* Linkage Group 4 of the Monsanto Consensus Genetic Map. In further aspects, the earliness trait co-segregates with a homozygous earliness allele at more than one genetic marker located on *Cucumis melo* Linkage Group 4 of the Monsanto Consensus Genetic Map. In a further aspect, the earliness trait co-segregates with a homozygous G nucleotide, "GG", at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In a further aspect, the earliness trait co-segregates with a homozygous G nucleotide, "GG", at marker NU0243432, a homozygous C nucleotide, "CC", at marker NU0220305, and a homozygous T nucleotide, "TT", at marker NCMEL008579265. In a further aspect, the *Cucumis melo* plant with both earliness and red flesh co-segregate with a homozygous G nucleotide, "GG", at marker NU0243432, a homozygous C nucleotide, "CC", at marker NU0220305, and a homozygous T nucleotide, "TT", at marker NCMEL009758372. In further aspects, the earliness trait co-segregates with a homozygous G nucleotide, "GG", at marker NU0243432, a heterozygous C nucleotide at marker NU0220305, a homozygous T nucleotide, "TT", at marker NCMEL009758372, and a homozygous T nucleotide, "TT", at marker NCMEL008579265. In further aspects, the earliness trait co-segregates with a homozygous G nucleotide, "GG", at marker NU0243432, a heterozygous C nucleotide at marker NU0220305, and a homozygous T nucleotide, "TT", at marker NCMEL008579265. In further aspects, the earliness trait co-segregates with a homozygous G nucleotide, "GG", at marker NU0243432, a heterozygous C nucleotide at marker NU0220305, and a homozygous T nucleotide, "TT", at marker NCMEL009758372. In further aspects, the earliness trait co-segregates with a heterozygous G nucleotide at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In further aspects, the earliness trait co-segregates with a heterozygous G nucleotide at marker NU0243432, a homozygous C nucleotide, "CC", at marker NU0220305, and a homozygous T nucleotide, "TT", at marker NCMEL008579265. In further aspects, the earliness trait co-segregates with a heterozygous G nucleotide at marker NU0243432, a homozygous C nucleotide, "CC", at marker NU0220305, and a homozygous T nucleotide, "TT", at marker NCMEL009758372. In further aspects, the earliness trait co-segregates with a heterozygous G nucleotide at marker NU0243432, a heterozygous C nucleotide at marker NU0220305, a homozygous T nucleotide, "TT", at marker NCMEL009758372, and a homozygous T nucleotide, "TT", at marker NCMEL008579265. In further aspects, the earliness trait co-segregates with a heterozygous G nucleotide at marker NU0243432, a heterozygous C nucleotide at marker NU0220305, and a homozygous T nucleotide, "TT", at marker NCMEL008579265. In further aspects, the earliness trait co-segregates with a heterozygous G nucleotide at marker NU0243432, a heterozygous C nucleotide at marker NU0220305, and a homozygous T nucleotide, "TT", at marker NCMEL009758372. In further aspects, the earliness trait co-segregates with a homozygous G nucleotide, "GG", at marker NU0243432, a homozygous T nucleotide, "TT", at marker NCMEL009758372, and a homozygous T nucleotide, "TT", at marker NCMEL008579265. In further aspects, the earliness trait co-segregates with a homozygous G nucleotide, "GG", at marker NU0243432 and a homozygous T nucleotide, "TT", at marker NCMEL008579265. In further aspects, the earliness trait co-segregates with a homozygous G nucleotide, "GG", at marker NU0243432 and a homozygous T nucleotide, "TT", at marker NCMEL009758372. In further aspects, the earliness trait co-segregates with a heterozygous G nucleotide at marker NU0243432, a homozygous T nucleotide, "TT", at marker NCMEL009758372, and a homozygous T nucleotide, "TT", at marker NCMEL008579265. In further aspects, the earliness trait co-segregates with a heterozygous G nucleotide at marker NU0243432 and a homozygous T nucleotide, "TT", at marker NCMEL008579265. In further aspects, the earliness trait co-segregates with a heterozygous G nucleotide at marker NU0243432 and a homozygous T nucleotide, "TT", at marker NCMEL009758372. In further aspects, the earliness trait co-segregates with a homozygous C nucleotide, "CC", at marker NU0220305, a homozygous T nucleotide, "TT", at marker NCMEL009758372, and a homozygous T nucleotide, "TT", at marker NCMEL008579265. In further aspects, the earliness trait co-segregates with a homozygous C nucleotide, "CC", at marker NU0220305 and a homozygous T nucleotide, "TT", at marker NCMEL008579265. In further aspects, the earliness trait co-segregates with a homozygous C nucleotide, "CC", at marker NU0220305 and a homozygous T nucleotide, "TT", at marker NCMEL009758372. In further aspects, the earliness trait co-segregates with a heterozygous C nucleotide at marker NU0220305, a homozygous T nucleotide, "TT", at marker NCMEL009758372, and a homozygous T nucleotide, "TT", at marker NCMEL008579265. In further aspects, the earliness trait co-segregates with a heterozygous C nucleotide at marker NU0220305 and a homozygous T nucleotide, "TT", at marker NCMEL008579265. In further aspects, the earliness trait co-segregates with a heterozygous C nucleotide at marker NU0220305 and a homozygous T nucleotide, "TT", at marker NCMEL009758372. In further aspects, the earliness trait co-segregates with a homozygous G nucleotide, "GG", at marker NU0243432. In a further aspect, the *Cucumis melo* plant with both earliness and earliness co-segregate with a heterozygous G nucleotide at marker NU0243432. In further aspects, the earliness trait co-segregates with a homozygous C nucleotide, "CC", at marker NU0220305. In further aspects, the earliness trait co-segregates with a heterozygous C nucleotide, at marker NU0220305. In further aspects, the earliness trait co-segregates with a homozygous T nucleotide, "TT", at marker NCMEL009758372. In further aspects, the earliness trait co-segregates with a homozygous T nucleotide, "TT", at marker NCMEL008579265. In further aspects, the *Cucumis*

*melo* plant with both earliness and red flesh comprises flesh with a hue angle between 55° and 63°. In further aspects, the *Cucumis melo* plant with both earliness and red flesh reaches peak Brix accumulation at least 3 days earlier than a *Cucumis melo* plant without an earliness trait. In further aspects, the *Cucumis melo* plant with both earliness and red flesh reaches peak Brix accumulation at least 4 days earlier than a *Cucumis melo* plant without an earliness trait. In further aspects, the *Cucumis melo* plant with both earliness and red flesh reaches peak Brix accumulation at least 5 days earlier than a *Cucumis melo* plant without an earliness trait. In further aspects, the *Cucumis melo* plant with both earliness and red flesh reaches peak Brix accumulation at least 6 days earlier than a *Cucumis melo* plant without an earliness trait. In some aspects, genetic assays of the *Cucumis melo* plant comprise PCR, single strand conformational polymorphism analysis, denaturing gradient gel electrophoresis, cleavage fragment length polymorphism analysis, TAQMAN assay, or DNA sequencing.

In an aspect, an earliness phenotype co-segregates with a homozygous red flesh allele at one genetic marker located on *Cucumis melo* Linkage Group 4 of the Monsanto Consensus Genetic Map. In further aspects, the earliness phenotype co-segregates with a homozygous red flesh allele at more than one genetic marker located on *Cucumis melo* Linkage Group 4 of the Monsanto Consensus Genetic Map. In further aspects, the earliness phenotype co-segregates with a homozygous T nucleotide, "TT", at marker NCMEL008579265. In further aspects, the earliness phenotype co-segregates with a heterozygous red flesh allele at more than one genetic marker located on *Cucumis melo* Linkage Group 4 of the Monsanto Consensus Genetic Map. In further aspects, the earliness phenotype co-segregates with a heterozygous T nucleotide at marker NCMEL008579265. In further aspects, the earliness phenotype co-segregates with a homozygous T nucleotide at marker NCMEL009758372. In further aspects, the earliness phenotype co-segregates with a heterozygous T nucleotide at marker NCMEL009758372. In some aspects, genetic assays of the *Cucumis melo* plant comprise PCR, single strand conformational polymorphism analysis, denaturing gradient gel electrophoresis, cleavage fragment length polymorphism analysis, TAQMAN assay, or DNA sequencing.

In an aspect, the application provides markers genetically linked to the described red flesh and earliness loci which are located on *Cucumis melo* Linkage Group 4 of the Monsanto Consensus Genetic Map. In certain aspects, the markers are within 10 cM, 5 cM, 3 cM, 1 cM, or less, of a locus on *Cucumis melo* Linkage Group 4 of the Monsanto Consensus Genetic Map that allows for a red flesh phenotype, an earliness phenotype, or a red flesh phenotype linked to an earliness phenotype. In certain aspects, markers linked to and useful in molecular detection of red flesh phenotype linked to an earliness phenotype can be selected from the group consisting of NU0243432, NU0220305, NCMEL009758372, and NCMEL008579265. The presence of a given marker may be identified by use of well-known techniques, such as genetic assays as disclosed herein. In some aspects, genetic assays of the *Cucumis melo* plant comprise PCR, single strand conformational polymorphism analysis, denaturing gradient gel electrophoresis, cleavage fragment length polymorphism analysis, TAQMAN assay, or DNA sequencing. Genetic map position, physical map position, and sequence information are given for selected genetic markers linked to these loci on *Cucumis melo* Linkage Group 4 of the Monsanto Consensus Genetic Map in Table 1 (SEQ ID NOs:1-4).

TABLE 1

Map position for selected genetic markers according to the ICuGI Public Consensus Genetic Map.

| Marker | Physical map position (bp) | SEQ ID NO |
|---|---|---|
| NU0243432 | 28,346,029 | 3 |
| NU0220305 | 24,876,456 | 2 |
| NCMEL009758372 | 23,377,571 | 4 |
| NCMEL008579265 | 22,825,883 | 1 |

In an aspect, the present disclosure provides for a container of *Cucumis melo* seeds capable of producing a *Cucumis melo* plant comprising a red flesh trait linked to an earliness trait on *Cucumis melo* Linkage Group 4 of the Monsanto Consensus Genetic Map. The present disclosure provides a container of CHA-ZA15-0014AN seeds, a sample seed of *Cucumis melo* line CHA-ZA15-0014AN having been deposited under ATCC Accession Number PTA-124202. The present disclosure also provides a container of CHA-ZA15-0014AN progeny seeds and a container of seeds that produce fruit comprising a red flesh phenotype linked to an earliness phenotype derived from CHA-ZA15-0014AN. CHA-ZA15-0014AN seeds of the present disclosure produce melon plants that produce fruit comprising a red flesh phenotype linked to an earliness phenotype. The container of CHA-ZA15-0014AN seeds of the present disclosure may contain any number, weight or volume of seeds. For example, a container of *Cucumis melo* seeds capable of producing a *Cucumis melo* plant comprising a red flesh trait linked to an earliness trait on *Cucumis melo* Linkage Group 4 of the Monsanto Consensus Genetic Map can contain at least about 100, 200, 300, 400, 500, 600, 700, 800, 900, 1000, 1500, 2000, 2500, 3000, 3500, 4000, or more seeds. A container can contain at least 100 seeds. A container can contain at least 200 seeds. A container can contain at least 300 seeds. A container can contain at least 400 seeds. A container can contain at least 500 seeds. A container can contain at least 600 seeds. A container can contain at least 700 seeds. A container can contain at least 800 seeds. A container can contain at least 900 seeds. A container can contain at least 1000 seeds. A container can contain at least 1500 seeds. A container can contain at least 2000 seeds. A container can contain at least 2500 seeds. A container can contain at least 3000 seeds. A container can contain at least 3500 seeds. A container can contain at least 4000 seeds. A container can contain greater than 4000 seeds. Alternatively, the container can contain at least about 1 ounce, 5 ounces, 10 ounces, 1 pound, 2 pounds, 3 pounds, 4 pounds, 5 pounds, or more *Cucumis melo* seeds capable of producing a *Cucumis melo* plant comprising a red flesh trait linked to an earliness trait on *Cucumis melo* Linkage Group 4 of the Monsanto Consensus Genetic Map. The container can contain at least about 1 ounce of seeds. The container can contain at least about 5 ounces of seeds. The container can contain at least about 10 ounces of seeds. The container can contain at least about 1 pound of seeds. The container can contain at least about 2 pounds of seeds. The container can contain at least about 3 pounds of seeds. The container can contain at least about 4 pounds of seeds. The container can contain at least about 5 pounds of seeds. A container of CHA-ZA15-0014AN seeds of the present disclosure may be any container available in the art. By way of a non-limiting example, a container may be a box, a bag, a packet, a pouch, a tape roll, a pail, a foil, or a tube.

The application provides for and includes a method for detecting a red flesh locus linked to an earliness locus on *Cucumis melo* Linkage Group 4 of the Monsanto Consensus Genetic Map in a *Cucumis melo* plant comprising, obtaining at least one progeny seed from a cross comprising at least one *Cucumis melo* plant comprising a red flesh trait linked to an earliness trait on *Cucumis melo* Linkage Group 4 of the Monsanto Consensus Genetic Map; assaying said at least one progeny seed or a plant grown therefrom for the presence of at least one red flesh-associated allele and at least one allele associated with an earliness locus on *Cucumis melo* Linkage Group 4 of the Monsanto Consensus Genetic Map; and detecting at least one *Cucumis melo* seed or a plant grown therefrom comprising a red flesh-associated allele linked to at least one allele associated with an earliness locus.

The application provides for and includes a method for selecting a red flesh locus linked to an earliness locus on *Cucumis melo* Linkage Group 4 of the Monsanto Consensus Genetic Map in a *Cucumis melo* plant comprising, obtaining at least one progeny seed from a cross comprising at least one *Cucumis melo* plant comprising a red flesh trait linked to an earliness trait on *Cucumis melo* Linkage Group 4 of the Monsanto Consensus Genetic Map; assaying said at least one progeny seed or a plant grown therefrom for the presence of at least one red flesh-associated allele and at least one allele associated with an earliness locus on *Cucumis melo* Linkage Group 4 of the Monsanto Consensus Genetic Map; and selecting at least one *Cucumis melo* seed or a plant grown therefrom comprising a red flesh-associated allele linked to at least one allele associated with an earliness locus.

In an aspect of a method provided herein, assaying the progeny seed from a cross comprising at least one *Cucumis melo* plant comprising a red flesh trait linked to an earliness trait involves detecting a chromosomal region comprising an earliness locus on Linkage Group 4 of the Monsanto Consensus Genetic Map located within flanking markers NU0243432 and NU0220305 and a red flesh locus on Linkage Group 4 of the Monsanto Consensus Genetic Map located within flanking markers NU0220305 and NCMEL008579265. In further aspects of a method provided herein, the *Cucumis melo* plant with both earliness and red flesh co-segregate with a homozygous G nucleotide, "GG", at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In further aspects of a method provided herein, the *Cucumis melo* plant with both earliness and red flesh co-segregate with a homozygous G nucleotide, "GG", at marker NU0243432, a homozygous C nucleotide, "CC", at marker NU0220305, and a homozygous T nucleotide, "TT", at marker NCMEL008579265. In further aspects of a method provided herein, the *Cucumis melo* plant with both earliness and red flesh co-segregate with a homozygous G nucleotide, "GG", at marker NU0243432, a homozygous C nucleotide, "CC", at marker NU0220305, and a homozygous T nucleotide, "TT", at marker NCMEL009758372. In further aspects of a method provided herein, the *Cucumis melo* plant with both earliness and red flesh co-segregate with a homozygous G nucleotide, "GG", at marker NU0243432, a heterozygous C nucleotide at marker NU0220305, a homozygous T nucleotide, "TT", at marker NCMEL009758372, and a homozygous T nucleotide, "TT", at marker NCMEL008579265. In further aspects of a method provided herein, the *Cucumis melo* plant with both earliness and red flesh co-segregate with a homozygous G nucleotide, "GG", at marker NU0243432, a heterozygous C nucleotide at marker NU0220305, and a homozygous T nucleotide, "TT", at marker NCMEL009758372. In further aspects of a method provided herein, the *Cucumis melo* plant with both earliness and red flesh co-segregate with a heterozygous G nucleotide at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In further aspects of a method provided herein, the *Cucumis melo* plant with both earliness and red flesh co-segregate with a heterozygous G nucleotide at marker NU0243432, a homozygous C nucleotide, "CC", at marker NU0220305, and a homozygous T nucleotide, "TT", at marker NCMEL008579265. In further aspects of a method provided herein, the *Cucumis melo* plant with both earliness and red flesh co-segregate with a heterozygous G nucleotide at marker NU0243432, a homozygous C nucleotide, "CC", at marker NU0220305, and a homozygous T nucleotide, "TT", at marker NCMEL009758372. In further aspects of a method provided herein, the *Cucumis melo* plant with both earliness and red flesh co-segregate with a heterozygous G nucleotide at marker NU0243432, a heterozygous C nucleotide at marker NU0220305, a homozygous T nucleotide, "TT", at marker NCMEL009758372, and a homozygous T nucleotide, "TT", at marker NCMEL008579265. In further aspects of a method provided herein, the *Cucumis melo* plant with both earliness and red flesh co-segregate with a heterozygous G nucleotide at marker NU0243432, a heterozygous C nucleotide at marker NU0220305, and a homozygous T nucleotide, "TT", at marker NCMEL009758372. In further aspects of a method provided herein, the *Cucumis melo* plant with both earliness and red flesh co-segregate with a homozygous G nucleotide, "GG", at marker NU0243432, a homozygous T nucleotide, "TT", at marker NCMEL009758372, and a homozygous T nucleotide, "TT", at marker NCMEL008579265. In further aspects of a method provided herein, the *Cucumis melo* plant with both earliness and red flesh co-segregate with a homozygous G nucleotide, "GG", at marker NU0243432 and a homozygous T nucleotide, "TT", at marker NCMEL008579265. In further aspects of a method provided herein, the *Cucumis melo* plant with both earliness and red flesh co-segregate with a homozygous G nucleotide, "GG", at marker NU0243432 and a homozygous T nucleotide, "TT", at marker NCMEL009758372. In further aspects of a method provided herein, the *Cucumis melo* plant with both earliness and red flesh co-segregate with a heterozygous G nucleotide at marker NU0243432, a homozygous T nucleotide, "TT", at marker NCMEL009758372, and a homozygous T nucleotide, "TT", at marker NCMEL008579265. In further aspects of a method provided herein, the *Cucumis melo* plant with both earliness and red flesh co-segregate with a heterozygous G nucleotide at marker NU0243432 and a homozygous T nucleotide, "TT", at marker NCMEL008579265. In further aspects of a method provided herein, the *Cucumis melo* plant with both earliness and red flesh co-segregate with a heterozygous G nucleotide at marker NU0243432 and a homozygous T nucleotide, "TT", at marker NCMEL009758372. In further aspects of a method provided herein, the *Cucumis melo* plant with both earliness and red flesh co-segregate with a homozygous C nucleotide, "CC", at marker NU0220305, a homozygous T nucleotide, "TT", at marker NCMEL009758372, and a homozygous T nucleotide, "TT", at marker NCMEL008579265. In further aspects of a method provided herein, the *Cucumis melo* plant with both earliness and red flesh co-segregate with a homozygous C nucleotide, "CC", at marker NU0220305, and a homozygous T nucleotide, "TT", at marker NCMEL008579265. In further aspects of a method provided herein, the *Cucumis melo* plant with both earliness and red flesh co-segregate with a homozygous C nucleotide, "CC", at marker NU0220305, and a homozygous T nucleotide, "TT", at marker NCMEL009758372. In further aspects of a method provided herein, the *Cucumis melo* plant with both earliness and red flesh co-segregate with a heterozygous C nucleotide at marker NU0220305, a homozygous T nucleotide, "TT", at marker NCMEL009758372, and a homozygous T nucleotide, "TT", at marker NCMEL008579265. In further aspects of a method provided herein, the *Cucumis melo* plant with both earliness and red flesh co-segregate with a heterozygous C nucleotide at marker NU0220305 and a homozygous T nucleotide, "TT", at marker NCMEL008579265. In further aspects of a method provided herein, the *Cucumis melo* plant with both earliness and red flesh co-segregate with a heterozygous C nucleotide at marker NU0220305 and a homozygous T nucleotide, "TT", at marker NCMEL009758372. In further aspects of a method provided herein, the *Cucumis melo* plant with both earliness and red flesh co-segregate with a homozygous G nucleotide, "GG", at marker NU0243432. In further aspects of a method provided herein, the *Cucumis melo* plant with both earliness and red flesh co-segregate with a heterozygous G nucleotide at marker NU0243432. In further aspects of a method provided herein, the *Cucumis melo* plant with both earliness and red flesh co-segregate with a homozygous C nucleotide, "CC", at marker NU0220305. In further aspects of a method provided herein, the *Cucumis melo* plant with both earliness and red flesh co-segregate with a heterozygous C nucleotide, at marker NU0220305. In further aspects of a method provided herein, the *Cucumis melo* plant with both earliness and red flesh co-segregate with a homozygous T nucleotide, "TT", at marker NCMEL009758372. In further aspects of a method provided herein, the *Cucumis melo* plant with both earliness and red flesh co-segregate with a homozygous T nucleotide, "TT", at marker NCMEL008579265. In further aspects of a method provided herein, the *Cucumis melo* plant with both earliness and red flesh reaches peak Brix accumulation at least 3 days earlier than a *Cucumis melo* plant without an earliness trait. In further aspects of a method provided herein, the *Cucumis melo* plant with both earliness and red flesh reaches peak Brix accumulation at least 4 days earlier than a *Cucumis melo* plant without an earliness trait. In further aspects of a method provided herein, the *Cucumis melo* plant with both earliness and red flesh reaches peak Brix accumulation at least 5 days earlier than a *Cucumis melo* plant without an earliness trait. In further aspects of a method provided herein, the *Cucumis melo* plant with both earliness and red flesh reaches peak Brix accumulation at least 6 days earlier than a *Cucumis melo* plant without an earliness trait. In some aspects of a method provided herein, genetic assays of the *Cucumis melo* plant comprise PCR, single strand conformational polymorphism analysis, denaturing gradient gel electrophoresis, cleavage fragment length polymorphism analysis, TAQMAN assay, or DNA sequencing. In further aspects of a method provided herein, an earliness locus can be detected using an assay that detects any marker that is linked to the markers NU0243432 or NU0220305. In further aspects of a method provided herein, a red flesh locus can be detected using an assay that detects any marker that is linked to the markers NU0220305, NCMEL009758372, or NCMEL008579265.

In certain aspects of a method provided herein, the *Cucumis melo* seed obtained that is capable of growing a plant comprising an earliness trait linked to a red flesh trait on Linkage Group 4 of the Monsanto Consensus Genetic Map is seed of *Cucumis melo* line CHA-ZA15-0014AN. In certain aspects of a method provided herein, the *Cucumis melo* seed obtained is progeny seed from a cross between one parent comprising an earliness trait and another parent comprising a red flesh trait. In certain aspects of a method provided herein, the *Cucumis melo* seed obtained is progeny seed from a cross between one parent comprising an earliness trait obtainable from the *Cucumis melo* line "BEST" and another parent comprising a red flesh trait obtainable from *Cucumis melo* line CHA-192-0058-MO.

In certain aspects of a method provided herein, a genetic marker linked to and useful in molecular detection of the earliness locus is selected from the group consisting of NU0219671, NU0243432, NU0243324, NU0219095, NU0218257, NU0219354, NU0219672, NU0219274, NU0243607, NU0219118, NU0220372, NU0220305, and NU0220446. In certain aspects of a method provided herein, a genetic marker linked to and useful in molecular detection of the red flesh locus is selected from the group consisting of NU0220305, NU0220372, NU0219774, NCMEL009758372, NU0219889, NU0244419, NU0244478, NU0220446, NU0219650, NU0244718, NU0218943, NCMEL008579265, NU0219136, NU0243542, NU0219676, and NU0243281. In further aspects of a method provided herein, an earliness locus can be detected using an assay that detects any marker that is linked to the markers NU0219671, NU0243432, NU0243324, NU0219095, NU0218257, NU0219354, NU0219672, NU0219274, NU0243607, NU0219118, NU0220372, NU0220305, and NU0220446. In further aspects of a method provided herein, a red flesh locus can be detected using an assay that detects any marker that is linked to the markers NU0220305, NU0220372, NU0219774, NCMEL009758372, NU0219889, NU0244419, NU0244478, NU0220446, NU0219650, NU0244718, NU0218943, NCMEL008579265, NU0219136, NU0243542, NU0219676, and NU0243281.

The application provides for and includes a method of producing *Cucumis melo* germplasm, plants, or plant parts comprising planting a *Cucumis melo* seed and growing said seed into a *Cucumis* plant wherein said *Cucumis melo* plant comprises a fruit having red flesh with a hue angle between 55° and 63° and a red flesh trait linked to an earliness trait on *Cucumis melo* Linkage Group 4 of the Monsanto Consensus Genetic Map.

In a further aspect of this method, a *Cucumis melo* plant comprises a fruit having red flesh with a hue angle between 55° and 63° and a red flesh trait linked to an earliness trait on *Cucumis melo* Linkage Group 4 of the Monsanto Consensus Genetic Map wherein a *Cucumis melo* plant with an earliness trait reaches peak Brix accumulation at least 3 days earlier than a *Cucumis melo* plant without an earliness trait. In a further aspect of this method, a *Cucumis melo* plant comprises a fruit having red flesh with a hue angle between 55° and 63° and a red flesh trait linked to an earliness trait on *Cucumis melo* Linkage Group 4 of the Monsanto Consensus Genetic Map wherein a *Cucumis melo* plant with an earliness trait reaches peak Brix accumulation at least 4 days earlier than a *Cucumis melo* plant without an earliness trait. In a further aspect of this method, a *Cucumis melo* plant comprises a fruit having red flesh with a hue angle between 55° and 63° and a red flesh trait linked to an earliness trait on *Cucumis melo* Linkage Group 4 of the Monsanto Consensus Genetic Map wherein a *Cucumis melo* plant with an earliness trait reaches peak Brix accumulation at least 5 days earlier than a *Cucumis melo* plant without an earliness trait. In a further aspect of this method, a *Cucumis melo* plant comprises a fruit having red flesh with a hue angle between 55° and 63° and a red flesh trait linked to an earliness trait on *Cucumis melo* Linkage Group 4 of the Monsanto Consensus Genetic Map wherein a *Cucumis melo* plant with an earliness trait reaches peak Brix accumulation at least 6 days earlier than a *Cucumis melo* plant without an earliness trait.

In an aspect of this method, a *Cucumis melo* plant comprising a fruit having red flesh with a hue angle between 55 and 63° and a red flesh trait linked to an earliness trait on *Cucumis melo* Linkage Group 4 of the Monsanto Consensus Genetic Map is grown. In a further aspect of this method, the *Cucumis melo* plant comprising a fruit having red flesh with a hue angle between 55 and 63° and a red flesh trait linked to an earliness trait on *Cucumis melo* Linkage Group 4 of the Monsanto Consensus Genetic Map comprises an earliness locus located within flanking markers NU0243432 and NU0220305 linked to a red flesh locus located within flanking markers NU0220305 and NCMEL008579265 on Linkage Group 4 of the Monsanto Consensus Genetic Map. In further aspects of this method, the *Cucumis melo* plant with both earliness and red flesh co-segregate with a homozygous G nucleotide, "GG", at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In further aspects of this method, the *Cucumis melo* plant with both earliness and red flesh co-segregate with a homozygous G nucleotide, "GG", at marker NU0243432, a homozygous C nucleotide, "CC", at marker NU0220305, and a homozygous T nucleotide, "TT", at marker NCMEL008579265. In further aspects of this method, the *Cucumis melo* plant with both earliness and red flesh co-segregate with a homozygous G nucleotide, "GG", at marker NU0243432, a homozygous C nucleotide, "CC", at marker NU0220305, and a homozygous T nucleotide, "TT", at marker NCMEL009758372. In further aspects of this method, the *Cucumis melo* plant with both earliness and red flesh co-segregate with a homozygous G nucleotide, "GG", at marker NU0243432, a heterozygous C nucleotide at marker NU0220305, a homozygous T nucleotide, "TT", at marker NCMEL009758372, and a homozygous T nucleotide, "TT", at marker NCMEL008579265. In further aspects of this method, the *Cucumis melo* plant with both earliness and red flesh co-segregate with a homozygous G nucleotide, "GG", at marker NU0243432, a heterozygous C nucleotide at marker NU0220305, and a homozygous T nucleotide, "TT", at marker NCMEL008579265. In further aspects of this method, the *Cucumis melo* plant with both earliness and red flesh co-segregate with a homozygous G nucleotide, "GG", at marker NU0243432, a heterozygous C nucleotide at marker NU0220305, and a homozygous T nucleotide, "TT", at marker NCMEL009758372. In further aspects of this method, the *Cucumis melo* plant with both earliness and red flesh co-segregate with a heterozygous G nucleotide at marker NU0243432, a homozygous C nucleotide, "CC", at marker NU0220305, a homozygous T nucleotide, "TT", at marker NCMEL009758372, and a homozygous T nucleotide, "TT", at marker NCMEL008579265. In further aspects of this method, the *Cucumis melo* plant with both earliness and red flesh co-segregate with a heterozygous G nucleotide at marker NU0243432, a homozygous C nucleotide, "CC", at marker NU0220305, and a homozygous T nucleotide, "TT", at marker NCMEL008579265. In further aspects of this method, the *Cucumis melo* plant with both earliness and red flesh co-segregate with a heterozygous G nucleotide at marker NU0243432, a homozygous C nucleotide, "CC", at marker NU0220305, and a homozygous T nucleotide, "TT", at marker NCMEL009758372. In further aspects of this method, the *Cucumis melo* plant with both earliness and red flesh co-segregate with a heterozygous G nucleotide at marker NU0243432, a heterozygous C nucleotide at marker NU0220305, a homozygous T nucleotide, "TT", at marker NCMEL008579265. In further aspects of this method, the *Cucumis melo* plant with both earliness and red flesh co-segregate with a heterozygous G nucleotide at marker NU0243432, a heterozygous C nucleotide at marker NU0220305, and a homozygous T nucleotide, "TT", at marker NCMEL008579265. In further aspects of this method, the *Cucumis melo* plant with both earliness and red flesh co-segregate with a heterozygous G nucleotide at marker NU0243432, a heterozygous C nucleotide at marker NU0220305, and a homozygous T nucleotide, "TT", at marker NCMEL009758372. In further aspects of this method, the *Cucumis melo* plant with both earliness and red flesh co-segregate with a homozygous G nucleotide, "GG", at marker NU0243432, a homozygous T nucleotide, "TT", at marker NCMEL009758372, and a homozygous T nucleotide, "TT", at marker NCMEL008579265. In further aspects of this method, the *Cucumis melo* plant with both earliness and red flesh co-segregate with a homozygous G nucleotide, "GG", at marker NU0243432 and a homozygous T nucleotide, "TT", at marker NCMEL008579265. In further aspects of this method, the *Cucumis melo* plant with both earliness and red flesh co-segregate with a homozygous G nucleotide, "GG", at marker NU0243432 and a homozygous T nucleotide, "TT", at marker NCMEL009758372. In further aspects of this method, the *Cucumis melo* plant with both earliness and red flesh co-segregate with a heterozygous G nucleotide at marker NU0243432, a homozygous T nucleotide, "TT", at marker NCMEL009758372, and a homozygous T nucleotide, "TT", at marker NCMEL008579265. In further aspects of this method, the *Cucumis melo* plant with both earliness and red flesh co-segregate with a heterozygous G nucleotide at marker NU0243432 and a homozygous T nucleotide, "TT", at marker NCMEL008579265. In further aspects of this method, the *Cucumis melo* plant with both earliness and red flesh co-segregate with a heterozygous G nucleotide at marker NU0243432 and a homozygous T nucleotide, "TT", at marker NCMEL009758372. In further aspects of this method, the *Cucumis melo* plant with both earliness and red flesh co-segregate with a homozygous C nucleotide, "CC", at marker NU0220305, a homozygous T nucleotide, "TT", at marker NCMEL009758372, and a homozygous T nucleotide, "TT", at marker NCMEL008579265. In further aspects of this method, the *Cucumis melo* plant with both earliness and red flesh co-segregate with a homozygous C nucleotide, "CC", at marker NU0220305, and a homozygous T nucleotide, "TT", at marker NCMEL008579265. In further aspects of this method, the *Cucumis melo* plant with both earliness and red flesh co-segregate with a homozygous C nucleotide, "CC", at marker NU0220305, and a homozygous T nucleotide, "TT", at marker NCMEL009758372. In further aspects of this method, the *Cucumis melo* plant with both earliness and red flesh co-segregate with a heterozygous C nucleotide at marker NU0220305, a homozygous T nucleotide, "TT", at marker NCMEL009758372, and a homozygous T nucleotide, "TT", at marker NCMEL008579265. In further aspects of this method, the *Cucumis melo* plant with both earliness and red flesh co-segregate with a heterozygous C nucleotide at marker NU0220305 and a homozygous T nucleotide, "TT", at marker NCMEL008579265. In further aspects of this method, the *Cucumis melo* plant with both earliness and red flesh co-segregate with a heterozygous C nucleotide at marker NU0220305 and a homozygous T nucleotide, "TT", at marker NCMEL009758372. In further aspects of this method, the *Cucumis melo* plant with both earliness and red flesh co-segregate with a homozygous G nucleotide, "GG", at marker NU0243432. In further aspects of this method, the *Cucumis melo* plant with both earliness and red flesh co-segregate with a heterozygous G nucleotide at marker NU0243432. In further aspects of this method, the *Cucumis melo* plant with both earliness and red flesh co-segregate with a homozygous C nucleotide, "CC", at marker NU0220305. In further aspects of this method, the *Cucumis melo* plant with both earliness and red flesh co-segregate with a heterozygous C nucleotide, at marker NU0220305. In further aspects of this method, the *Cucumis melo* plant with both earliness and red flesh co-segregate with a homozygous T nucleotide, "TT", at marker NCMEL009758372. In further aspects of this method, the *Cucumis melo* plant with both earliness and red flesh co-segregate with a homozygous T nucleotide, "TT", at marker NCMEL008579265. In further aspects of this method, the *Cucumis melo* plant with both earliness and red flesh reaches peak Brix accumulation at least 3 days earlier than a *Cucumis melo* plant without an earliness trait. In further aspects of this method, the *Cucumis melo* plant with both earliness and red flesh reaches peak Brix accumulation at least 4 days earlier than a *Cucumis melo* plant without an earliness trait. In further aspects of this method, the *Cucumis melo* plant with both earliness and red flesh reaches peak Brix accumulation at least 5 days earlier than a *Cucumis melo* plant without an earliness trait. In further aspects of this method, the *Cucumis melo* plant with both earliness and red flesh reaches peak Brix accumulation at least 6 days earlier than a *Cucumis melo* plant without an earliness trait. In some aspects of this method, genetic assays of the *Cucumis melo* plant comprise PCR, single strand conformational polymorphism analysis, denaturing gradient gel electrophoresis, cleavage fragment length polymorphism analysis, TAQMAN assay, or DNA sequencing.

In a further aspect of this method, the *Cucumis melo* plant detected with both earliness and red flesh is the progeny of the *Cucumis melo* plant that comprises a G nucleotide at marker NU0243432 linked to a C nucleotide at marker NU0220305 linked to a T nucleotide at marker NCMEL009758372 linked to a T nucleotide at marker NCMEL008579265. In a further aspect of this method, the *Cucumis melo* plant detected with both earliness and red flesh is the progeny of the *Cucumis melo* plant that comprises a G nucleotide at marker NU0243432 linked to a C nucleotide at marker NU0220305 linked to a T nucleotide at marker NCMEL008579265. In a further aspect of this method, the *Cucumis melo* plant detected with both earliness and red flesh is the progeny of a *Cucumis melo* plant that comprises a G nucleotide at marker NU0243432 linked to a T nucleotide at marker NCMEL008579265. In a further aspect of this method, the *Cucumis melo* plant detected with both earliness and red flesh is the progeny of a *Cucumis melo* plant that comprises a G nucleotide at marker NU0243432 linked to a T nucleotide at marker NCMEL009758372. In a further aspect of this method, the *Cucumis melo* plant detected with both earliness and red flesh is the progeny of a *Cucumis melo* plant that comprises a C nucleotide at marker NU0220305 linked to a T nucleotide at marker NCMEL008579265. In a further aspect of this method, the *Cucumis melo* plant detected with both earliness and red flesh is the progeny of a *Cucumis melo* plant that comprises a C nucleotide at marker NU0220305 linked to a T nucleotide at marker NCMEL009758372. In some aspects of this method, genetic assays of the *Cucumis melo* plant comprise PCR, single strand conformational polymorphism analysis, denaturing gradient gel electrophoresis, cleavage fragment length polymorphism analysis, TAQMAN assay, or DNA sequencing.

In an aspect of this method, the *Cucumis melo* seed that produces a plant that comprises a fruit having red flesh with a hue angle between 55 and 63° and a red flesh trait linked to an earliness trait on *Cucumis melo* Linkage Group 4 of the Monsanto Consensus Genetic Map is of the *Cucumis melo* line CHA-ZA15-0014AN. In certain aspects of this method, the *Cucumis melo* seed is planted that is a $F_1$ progeny from a cross where the *Cucumis melo* line CHA-ZA15-0014AN is at least one of the parents. In other aspects of this method, the *Cucumis melo* seed will contain genomic material that will confer a red flesh phenotype linked to an earliness phenotype as is found in CHA-ZA15-0014AN or as derived from CHA-ZA15-0014AN where CHA-ZA15-0014AN is in the pedigree of the seed material.

In certain aspects of this method, a genetic marker linked to and useful in molecular detection of the earliness locus is selected from the group consisting of NU0219671, NU0243432, NU0243324, NU0219095, NU0218257, NU0219354, NU0219672, NU0219274, NU0243607, NU0219118, NU0220372, NU0220305, and NU0220446. In certain aspects of this method, a genetic marker linked to and useful in molecular detection of the red flesh locus is selected from the group consisting of NU0220305, NU0220372, NU0219774, NCMEL009758372, NU0219889, NU0244419, NU0244478, NU0220446, NU0219650, NU0244718, NU0218943, NCMEL008579265, NU0219136, NU0243542, NU0219676, and NU0243281.

Unless defined otherwise, technical and scientific terms used herein have the same meaning as those commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents and publications, are incorporated by reference in their entirety.

As used herein, the singular form "a," "an,' and "the" include plural references unless the context clearly dictates otherwise. For example, the term "a plant" or "at least one plant" may include a plurality of plants.

The term "about" is used herein to mean approximately, roughly, around, or in the region of. When the term "about" is used in conjunction with a numerical range, it modifies that range by extending the boundaries above and below the numerical values set forth plus or minus 10%.

As used herein, and unless indicated otherwise, "plant" refers to a whole plant or a cell or tissue culture derived from a plant, comprising any of: whole plants, plant components or organs (e.g., leaves, stems, roots, fruits, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

As used herein, the term "plant, or part thereof" includes plant cells, plant protoplasts, plant cells of tissue culture from which melon plants can be regenerated, plant calli, plant clumps, and plant cells that are intact in plants or parts of plants such as pollen, flowers, seeds, leaves, stems, fruit, and the like.

As used herein, the term "population" means a genetically heterogenous collection of plants that share a common parental derivation.

As used herein, the term "inbred" or "inbred line" means a substantially homozygous individual or variety.

As used herein, the term "hybrid" means an offspring of a cross between two genetically unlike individuals.

As used herein, "similar growth conditions" refer to similar environmental conditions and/or agronomic practices for growing and making meaningful comparisons between two or more plant genotypes so that neither environmental conditions nor agronomic practices would contribute significantly to or explain any difference observed between the two or more plant genotypes. Environmental conditions include, for example, light, temperature, water (humidity), and nutrition (e.g., nitrogen and phosphorus).

As used herein, "selecting" or "selection" in the context of marker-assisted selection (MAS) or breeding refer to the act of picking or choosing desired individuals, normally from a population, based on certain pre-determined criteria.

As used herein, the term "trait" refers to a phenotype or one or more detectable characteristics of a cell or organism which can be influenced by genotype. The phenotype can be observable to the naked eye, or by any other means of evaluation known in the art, e.g., microscopy, biochemical analysis, genomic analysis, an assay for a further disease tolerance, etc. In some cases, a phenotype is directly controlled by a single gene or genetic locus, e.g., a "single gene trait." In other cases, a phenotype is the result of several genes.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length poly-morphisms (RFLPs), simple sequence repeats (SSRs), insertion(s)/deletion(s) ("INDEL"(s)), inter-simple sequence repeats (ISSR), and random amplified polymorphic DNA (RAPD) sequences. DNA sequencing, e.g. of chromosomal DNA, may also be employed to determine the allele present at a given marker of interest. A marker is preferably inherited in co-dominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism. Stringent conditions for hybridization of a nucleic acid probe or primer to a marker sequence or a sequence flanking a marker sequence refers, for instance, to nucleic acid hybridization conditions of 1×SSC and 65° C.

As used herein, "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

As used herein, "probe" refers to an oligonucleotide (synthetic or occurring naturally) that is complementary (though not necessarily fully complementary) to a polynucleotide of interest and forms a duplex structure by hybridization with at least one strand of the polynucleotide of interest. Typically, probes are oligonucleotides from 10 to 50 nucleotides in length, but longer or shorter sequences can be employed. A probe can further contain a detectable label.

As used herein, "marker assay" means a method for detecting a marker at a locus using a method, e.g. measurement of at least one phenotype (such as a visually detectable trait, including red flesh and earliness), restriction fragment length polymorphism (RFLP), single base extension, electrophoresis, sequence alignment, allelic specific oligonucleotide hybridization (ASO), random amplified polymorphic DNA (RAPD), microarray-based technologies, PCR-based technologies, and nucleic acid sequencing technologies, etc.

As used herein, "polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism (RFLP), and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed, or tissues from which new plants may be grown, or plant parts, such as leaves, stems, pollen, ovules, or cells that can be cultured into a whole plant.

As used herein, a centimorgan ("cM") is a unit of measure of recombination frequency and genetic distance between two loci. One cM is equal to a 1% chance that a marker at one genetic locus will be separated from a marker at a second locus due to crossing over in a single generation. Genetic distances can be calculated from experimentally derived recombination values using the Kosambi function (Kosambi, The estimation of map distances from recombination values. *Annals of Eugenics,* 12:172-75 (1944)).

As used herein, "linked" or "genetically linked" means that the marker or locus is within about 20 cM, 19 cM, 18 cM, 17 cM, 16 cM, 15 cM, 14 cM, 13 cM, 12 cM, 11 cM, 10 cM, 9 cM, 8 cM, 7 cM, 6 cM, 5 cM, 4 cM, 3 cM, 2 cM, 1 cM, 0.5 cM, or less than 0.5 cM of another marker or locus on the same chromosome. For example, 10 cM means that recombination occurs between the marker and the locus with a highly predictable recombination frequency of equal to or less than about 10%.

The genetic linkage of marker molecules can be established by a gene mapping model such as, without limitation, the flanking marker model reported by Lander and Botstein, Genetics, 121:185-199 (1989), and interval mapping, based on maximum likelihood methods described by Lander and Botstein, Genetics, 121:185-199 (1989), and implemented in the software package MAPMAKER/QTL (Lincoln and Lander, Mapping Genes Controlling Quantitative Traits Using MAPMAKER/QTL, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.), JoinMap (Kyazma B. V., Wageningen, Netherlands), and mapQTL (Kyazma B. V., Wageningen, Netherlands).

As used herein, the phrase "associated with" or "linked to" refers to a recognizable and/or assayable relationship between two entities. As such, a marker is "associated with" a trait when it is linked to or co-segregates with it and when the presence of the marker is an indicator of whether and/or to what extent the desired trait or trait form will occur in a plant/germplasm comprising the marker. Similarly, a marker is "associated with" or "linked to" an allele when it is linked to or co-segregates with it and when the presence of the marker is an indicator of whether the allele is present in a plant/germplasm comprising the marker. For example, "a marker is linked to red flesh" when that marker is 10 cM or less away from an allele that co-segregates with red flesh.

As used herein, "crossed" or "cross" means to produce progeny via fertilization (e.g. cells, seeds or plants) and includes crosses between plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. (Ragot et al., Marker-assisted Backcrossing: A Practical Example. *Techniques Et Utilisations Des Marqueurs Moleculaires Les Colloques,* 72:45-56 (1995); and Openshaw et al., Marker-assisted Selection in Backcross Breeding, in *Proceedings Of The Symposium "Analysis of Molecular Marker Data,"* pp. 41-43 (1994)). The initial cross gives rise to the $F_1$ generation. The term "$BC_1$" refers to the second use of the recurrent parent, "$BC_2$" refers to the third use of the recurrent parent, and so on. In an aspect, a backcross is performed repeatedly, with a progeny individual of each successive backcross generation being itself backcrossed to the same parental genotype.

As used herein, "genetic element" or "gene" refers to a heritable sequence of DNA, e.g., a genomic sequence, with functional significance. The term "gene" can also be used to refer to, e.g., a cDNA or an mRNA encoded by a genomic sequence, as well as to that genomic sequence.

As used herein, "genotype" is the genetic constitution of an individual (or group of individuals) at one or more genetic loci, as contrasted with the observable trait (phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all its genome.

As used herein, a "haplotype" is the genotype of an individual at a plurality of genetic loci. Typically, the genetic loci described by a haplotype are physically and genetically linked, e.g., in the same chromosome interval. Selection based upon a haplotype can be more effective than selection based upon a single marker locus.

A "Quantitative Trait Locus (QTL)" is a chromosomal location that encodes for alleles that affect the expressivity of a phenotype.

As used herein, the term "phenotype" means the detectable characteristics of a cell or organism that can be influenced by gene expression.

As used herein, the term "introgressed," when used in reference to a genetic locus, refers to a genetic locus that has been introduced into a new genetic background. Introgression of a genetic locus can thus be achieved through plant breeding methods and/or by molecular genetic methods. Such molecular genetic methods include, but are not limited to, various plant transformation techniques or methods that provide for homologous recombination, non-homologous recombination, site-specific recombination, or genomic modifications that provide for locus substitution or locus conversion.

As used herein, "mapping" is the process of defining the linkage relationships of loci through the use of genetic markers, populations segregating for the markers, and standard genetic principles of recombination frequency.

As used herein, "genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). In general, the closer two markers or genomic loci are on the genetic map, the closer they lie to one another on the physical map. A physical map of the genome does not take into account the genetic behavior (e.g., recombination frequencies) between different points on the physical map. A lack of precise proportionality between genetic distances and physical distances can exist due to the fact that the likelihood of genetic recombination is not uniform throughout the genome; some chromosome regions are cross-over "hot spots," while other regions demonstrate only rare recombination events, if any. Genetic mapping variability can also be observed between different populations of the same crop species. In spite of this variability in the genetic map that may occur between populations, genetic map and marker information derived from one population generally remain useful across multiple populations in identification of plants with desired traits, counter-selection of plants with undesirable traits and in MAS breeding. As one of skill in the art will recognize, recombination frequencies (and as a result, genetic map positions) in any further populations are not static. The genetic distances separating two markers (or a marker and a QTL) can vary depending on how the map positions are determined. For example, variables such as the parental mapping populations used, the software used in marker mapping or QTL mapping, and the parameters input by the user of the mapping software can contribute to the QTL marker genetic map relationships. However, it is not intended that the disclosure be limited to any further mapping populations, use of any further software, or any further set of software parameters to determine linkage of a further marker or chromosome interval with a desired phenotype. It is well within the ability of one of ordinary skill in the art to extrapolate the novel features described herein to any gene pool or population of interest, and using any further software and software parameters. Indeed, observations regarding genetic markers and chromosome intervals in populations in addition to those described herein are readily made using the teaching of the present disclosure.

As used herein, "genetic map" or "genetic map location" refers to the position of a marker, loci, or genetic feature as found on the Monsanto Consensus Genetic Map for *Cucumis melo*. All genetic map locations listed herein are provided in cM as determined from the Monsanto Consensus Genetic Map. As used herein, "physical map" or "physical map location" refers to the position of a marker, loci, or genetic feature as found on the current ICuGI Public Consensus Genetic Map. All physical map locations listed herein are provided in basepair number as determined from the ICuGI Public Consensus Genetic Map.

The publicly available *Cucumis melo* maps include the ICuGI Public Consensus Genetic Map published by the International Cucurbit Genomics Initiative (Diaz, et al., "A consensus linkage map for molecular markers and quantitative trait loci associated with economically important traits in melon (*Cucumis melo* L.)," BMC Plant Biol. 11:111, 2011; "Diaz") and the linkage map of Oliver et al., 2001 (Oliver, et al., "Construction of a reference linkage map for melon," Genome 44:836-845, 2001; "Oliver"). The ICuGI has a comprehensive curation of past and current maps. The differences between the ICuGI Consensus map, the Oliver map, and the Monsanto Consensus Genetic Map are summarized in Table 2. The physical positions in nucleotide basepairs for markers disclosed in the present specification are taken from the ICuGI consensus map (www.icugi.org). According to the ICuGI Public Consensus Genetic Map, Linkage Group 6 of the ICuGI Public Consensus Genetic Map contains 35,939,859 nucleotides basepairs (bp). According to Diaz, Linkage Group 6 of the ICuGI Public Consensus Genetic Map is approximately 98 cM indicating that 1 cM is approximately equivalent to 366,733 bp on this map assuming equivalent crossover frequency over the entire Linkage Group (35,939,859 bp/98 cM=366,733 bp per cM).

TABLE 2

Two currently available genetic maps compared to the Monsanto Consensus Genetic Map.

| Oliver 2001 Map | ICuGI Public Consensus Genetic Map | Monsanto Consensus Genetic Map | ICuGI Public Consensus chromosome |
| --- | --- | --- | --- |
| G1 | LG8 | LG8 | 8 |
| G2 | LG3 | LG3 | 3 |
| G3 | LG7 | LG7 | 7 |
| G4 | LG5 | LG5 | 5 |
| G5 | LG11 | LG11 | 11 |
| G6 | LG1 | LG1 | 1 |
| G7 | LG9 | LG9 | 9 |
| G8 | LG2 | LG2 | 2 |
| G9 | LG10 | LG10 | 10 |
| G10 | LG4 | LG6 | 4 |
| G11 | LG12 | LG12 | 12 |
| G12 | LG6 | LG4 | 6 |

As used herein, "Linkage Group" refers to one of twelve genetic intervals on a melon genetic map. As used herein, and unless indicated otherwise, "Linkage Group 4 of the Monsanto Consensus Genetic Map" refers to a genetic interval on the Monsanto Consensus Genetic Map that corresponds with Linkage Group 6 of the ICuGI Public Consensus Genetic Map and Linkage Group 12 of the Oliver 2001 Map, as indicated in Table 2. Linkage Group 4 of the Monsanto Consensus Genetic Map is inverted as compared to the order of markers as found in Linkage Group 6 of the ICuGI Public Consensus Genetic Map. Chromosome number corresponds to the number of the linkage group as established on the ICuGI Public Consensus Genetic Map, for example Linkage Group 6 of the ICuGI Public Consensus Genetic Map is equivalent to Chromosome 6, Linkage Group 1 of the ICuGI Public Consensus Genetic Map is equivalent to Chromosome 1, and so on.

As used herein, "Least Square mean of hue" or "hue LSM" is a measure of fruit flesh color. As used herein, a melon fruit with a flesh hue LSM of less than 0.475 is defined as orange and a melon fruit with a hue LSM of greater than or equal to 0.475 is defined as red.

As used herein, "single locus converted plant" or "conversion plants" refers to plants which are developed by a plant breeding technique called backcrossing, wherein essentially all of the morphological and physiological characteristics of a *Cucumis melo* variety are recovered in addition to the characteristics of the single locus transferred into the variety via the backcrossing technique and/or by genetic transformation. Plants of this type may also be achieved through site-directed recombination techniques.

A genetic marker profile of an inbred may be predictive of the agronomic traits of a hybrid produced using that inbred. For example, if an inbred of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data is disclosed in U.S. Pat. No. 5,492,547, the disclosure of which is specifically incorporated herein by reference in its entirety. Such predictions may be made using any suitable genetic marker, for example, SSRs, CAPS, INDELs, RFLPs, AFLPs, SNPs, isozymes, or by DNA sequencing.

Additional markers, such as SSRs, AFLP markers, RFLP markers, RAPD markers, phenotypic markers, SNPs, isozyme markers, or microarray transcription profiles that are genetically linked to or correlated with alleles of a QTL of the present application can be utilized (Walton, *Seed World* 22-29 (July, 1993); Burow and Blake, *Molecular Dissection of Complex Traits,* 13-29, Eds. Paterson, CRC Press, New York (1988)). Methods to isolate such markers are known in the art. For example, locus-specific SSRs can be obtained by screening a genomic library for SSRs, sequencing "positive" clones, designing primers which flank the repeats, and amplifying genomic DNA with these primers.

Selection of appropriate mapping or segregation populations is important to map construction. The choice of appropriate mapping population depends on the type of marker systems employed (Tanksley et al., Molecular mapping plant chromosomes. *Chromosome structure and function: Impact of new concepts* J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less genetic material derived from one of the two originally crossed plants. As used herein, a second plant is derived from a first plant if the second plant's pedigree includes the first plant.

Desirable *Cucumis melo* plant traits, e.g., as displayed by agronomically elite lines or cultivars, and that may be independently selected include, but are not limited to: plant vigor, fruit flesh color, fruit rind morphology, time to maturity, adaptation to field growth, adaptation to greenhouse growth, and resistance to one or more diseases or disease causing organisms.

An $F_2$ population is the first generation of self or sib pollination after the hybrid seed is produced. Usually a single $F_1$ plant is self- or sib-pollinated to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (e.g., $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g., disease resistance) or where trait expression is controlled by a QTL. Segregation data from progeny test populations (e.g., $F_3$ or $BCF_2$) can be used in map construction. MAS can then be applied to cross progeny based on marker-trait map associations ($F_2$, $F_3$), where linkage groups have not been completely disassociated by recombination events (i.e., maximum disequilibrium).

Backcross populations can be utilized as a mapping population. A backcross population is created by one or more crosses from an $F_1$ with one of the parents. A series of backcrosses to the recurrent parent can be made to recover most of its desirable traits. Thus a population is created consisting of individuals nearly like the recurrent parent but each individual carries varying amounts or a mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A.*) 89:1477-1481 (1992)). Information obtained from backcross populations using either codominant or dominant markers is less than that obtained from $F_2$ populations because one, rather than two, recombinant gametes are sampled per plant. Backcross populations, however, are more informative (at low marker saturation) when compared to Recombinant Inbred Lines as the genetic distance between linked loci increases in Recombinant Inbred Line populations (i.e., about 15% recombination). Increased recombination can be beneficial for resolution of tight linkages, but may be undesirable in the construction of maps with low marker saturation.

Bulk segregant analysis (BSA) is a method developed for the rapid identification of linkage between markers and traits of interest (Michelmore, et al., *Proc. Natl. Acad. Sci.* (*U.S.A.*) 88:9828-9832 (1991)). In BSA, two bulked DNA samples are created from a segregating population originating from a single cross. These two bulked groups contain individuals that are assigned to one group or the other based on the presence or absence of the trait being interrogated (for example, either resistance or sensitivity to disease) or genomic region. For unlinked or distantly (~50 cM) linked loci, the frequency of alleles reflect that predicted by independent assortment and the population structure; i.e. regions unlinked to the target region will not differ between the BSA samples.

Plants generated using a method of the present application can be part of or generated from a breeding program. The choice of breeding method depends on the mode of plant reproduction, the heritability of the trait(s) being improved, and the type of cultivar used commercially (e.g., $F_1$ hybrid cultivar, pure line cultivar, etc). Selected, non-limiting approaches, for breeding the plants of the present application are set forth below. A breeding program can be enhanced using MAS of the progeny of any cross. It is further understood that any commercial and non-commercial cultivars can be utilized in a breeding program. Factors such as, for example, emergence vigor, vegetative vigor, stress tolerance, disease resistance, branching, flowering, fruit size, fruit quality, seed set, and seed density will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sib pollinating and selection, producing many new genetic combinations.

The development of new melon lines requires the development and selection of melon varieties, the crossing of these varieties and selection of superior hybrid crosses. The hybrid seed can be produced by manual crosses between selected male-fertile parents or by using male sterility systems. Hybrids are selected for certain traits such as fruit size, flesh color, or herbicide resistance which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is performed. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to deriving a new generation from a single seed from the previous generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (e.g., Fehr, *Principles of Cultivar Development* Vol. 1, pp. 2-3 (1987)).

The following are exemplary embodiments of the present disclosure.

embodiment 1. A *Cucumis melo* plant, or part thereof, wherein said *Cucumis melo* plant comprises a trait locus for a red flesh allele linked to a trait locus for an earliness allele on *Cucumis melo* Linkage Group 6 of the International Cucurbit Genomics Initiative (ICuGI) Public Consensus Genetic Map.

embodiment 2. The *Cucumis melo* plant, or part thereof, of embodiment 1, wherein said part is a selected from the group consisting of seed, leaf, cotyledon, pollen, embryo, root, root tip, anther, pistil, flower, bud, fruit, seed, stalk, and meristem.

embodiment 3. The *Cucumis melo* plant, or part thereof, of embodiment 1, wherein said red flesh allele is a homozygous red flesh allele on *Cucumis melo* Linkage Group 6 of the ICuGI Public Consensus Genetic Map.

embodiment 4. The *Cucumis melo* plant, or part thereof, of any one of embodiment s 1 to 3, wherein said part is a mature fruit comprising red flesh with a hue angle less than 63°.

embodiment 5. The *Cucumis melo* plant, or part thereof, of any one of embodiment s 1 to 4, wherein said part is a mature fruit comprising red flesh with a hue angle between 55° and 63°.

embodiment 6. The *Cucumis melo* plant, or part thereof, of any one of embodiment s 1 to 5, wherein said *Cucumis melo* plant is a hybrid.

embodiment 7. The *Cucumis melo* plant, or part thereof, of any one of embodiment s 1 to 6, wherein said *Cucumis melo* plant is an inbred line.

embodiment 8. A *Cucumis melo* plant, or part thereof, of any one of embodiment s 1 to 7, wherein said *Cucumis* plant is *Cucumis melo* cultivar CHA-ZA15-0014AN, a representative sample seed of *Cucumis melo* cultivar CHA-ZA15-0014AN having been deposited with the ATCC under ATCC Accession No. PTA-124202.

embodiment 9. The *Cucumis melo* plant, or part thereof, of any one of embodiment s 1 to 8, wherein said part is a mature fruit with total carotenes of at least 40 parts per million.

embodiment 10. The *Cucumis melo* plant, or part thereof, of any one of embodiment s 1 to 9, wherein said plant or part thereof comprises a homozygous earliness allele on *Cucumis melo* Linkage Group 6 of the ICuGI Public Consensus Genetic Map.

embodiment 11. The *Cucumis melo* plant, or part thereof, of any one of embodiment s 1 to 10, wherein said red flesh allele is located in a genomic region flanked by nucleic acid markers NCMEL0085795265 (SEQ ID NO: 1) and NU0220305 (SEQ ID NO: 2) on *Cucumis melo* Linkage Group 6 of the ICuGI Public Consensus Genetic Map.

embodiment 12. The *Cucumis melo* plant, or part thereof, of any one of embodiment s 1 to 11, wherein said homozygous red flesh allele comprises a TT nucleotide sequence identifiable using a nucleic acid probe having a nucleic acid sequence of SEQ ID NO: 5 or 6.

embodiment 13. The *Cucumis melo* plant, or part thereof, of any one of embodiment s 1 to 12, wherein said homozygous red flesh allele comprises a TT nucleotide sequence identifiable using a nucleic acid probe having a nucleic acid sequence of SEQ ID NO:17 or 18.

embodiment 14. The *Cucumis melo* plant, or part thereof, of any one of embodiment s 1 to 13, wherein said part is a mature fruit with total carotenes greater than a mature fruit obtained from an isogenic plant lacking a homozygous red flesh allele on *Cucumis melo* Linkage Group 6 of the ICuGI Public Consensus Genetic Map grown under similar conditions.

embodiment 15. The *Cucumis melo* plant, or part thereof, of any one of embodiment s 1 to 14, wherein said part is a mature fruit comprising 15 parts per million or greater total carotenes more than a mature fruit obtained from an isogenic plant lacking said homozygous red flesh allele on *Cucumis melo* Linkage Group 6 of the ICuGI Public Consensus Genetic Map, when grown under similar conditions.

embodiment 16. The *Cucumis melo* plant, or part thereof, of any one of embodiment s 1 to 15, wherein said part is a mature fruit with greater than 20% more total carotenes than that of a mature fruit obtained from an isogenic plant lacking said homozygous red flesh allele on *Cucumis melo* Linkage Group 6 of the ICuGI Public Consensus Genetic Map grown under similar conditions.

embodiment 17. The *Cucumis melo* plant, or part thereof, of any one of embodiment s 1 to 16, wherein said plant or part thereof comprises at least one earliness allele of an earliness locus.

embodiment 18. The *Cucumis melo* plant, or part thereof, of embodiment 17, wherein said earliness allele is located in a genomic region flanked by nucleic acid markers NU0220305 (SEQ ID NO: 2) and NU0243432 (SEQ ID NO: 3) on *Cucumis melo* Linkage Group 6 of the ICuGI Public Consensus Genetic Map.

embodiment 19. The *Cucumis melo* plant, or part thereof, of embodiment 17, wherein said earliness allele comprises a C nucleotide sequence identifiable using a nucleic acid probe having a nucleic acid sequence of SEQ ID NO: 9 or 10.

embodiment 20. The *Cucumis melo* plant, or part thereof, of embodiment 17, wherein said earliness allele comprises a G nucleotide sequence identifiable using a nucleic acid probe having a nucleic acid sequence of SEQ ID NO: 13 or 14.

embodiment 21. The *Cucumis melo* plant, or part thereof, of embodiment 17, wherein said plant comprises a fruit that reaches peak Brix accumulation at least three days earlier than a fruit obtained from an isogenic plant lacking an earliness allele on *Cucumis melo* Linkage Group 6 of the ICuGI Public Consensus Genetic Map, grown under similar conditions.

embodiment 22. The *Cucumis melo* plant, or part thereof, of any one of embodiment s 1 to 21, wherein said part is a cell derived from a tissue selected from the group consisting of leaf, cotyledon, pollen, embryo, root, root tip, anther, pistil, flower, bud, fruit, seed, stalk, and meristem.

embodiment 23. The *Cucumis melo* plant, or part thereof, of embodiment 22, wherein said cell is a non-reproductive cell.

embodiment 24. The *Cucumis melo* plant, or part thereof, of embodiment 22, wherein said cell is in a tissue culture.

embodiment 25. The *Cucumis melo* seed of any one of embodiment s 1 to 24, wherein said *Cucumis* plant is *Cucumis melo* cultivar or is derived from *Cucumis melo* cultivar CHA-ZA15-0014AN, a representative sample seed of *Cucumis melo* cultivar CHA-ZA15-0014AN having been deposited with the ATCC under ATCC Accession No. PTA-124202.

embodiment 26. A *Cucumis melo* seed capable of producing a *Cucumis melo* plant, wherein a plant grown from said seed comprises a trait locus for red flesh linked to a trait locus for earliness on *Cucumis melo* Linkage Group 6 of the ICuGI Public Consensus Genetic Map.

embodiment 27. A container comprising *Cucumis melo* seeds according to embodiment 26.

embodiment 28. The *Cucumis* melo seed of embodiment 26 or 27, wherein a plant grown from said seed further comprises a mature fruit having red flesh with a hue angle less than or equal to 63°.

embodiment 29. The *Cucumis melo* seed of any one of embodiment s 26 to 28, wherein a plant grown from said seed produces a mature fruit comprising red flesh with a hue angle between 55° and 63°.

embodiment 30. The *Cucumis melo* seed of any one of embodiment s 26 to 29, wherein a plant grown from said seed produces a fruit comprising total carotenes of at least 40 parts per million at maturity.

embodiment 31. The *Cucumis melo* seed of any one of embodiment s 26 to 30, wherein a plant grown from said seed further comprises a fruit with an average Brix content of at least 9° Brix at maturity.

embodiment 32. The *Cucumis melo* seed of any one of embodiment s 26 to 31, wherein a plant grown from said seed further comprises a fruit with an average Brix content of at least 11° Brix at maturity.

embodiment 33. The *Cucumis melo* seed of any one of embodiment s 26 to 32, wherein a plant grown from said seed comprises a homozygous red flesh allele on *Cucumis melo* Linkage Group 6 of the ICuGI Public Consensus Genetic Map.

embodiment 34. The *Cucumis melo* seed of embodiment 33, wherein said homozygous red flesh allele is located in a genomic region flanked by nucleic acid markers NCMEL0085795265 (SEQ ID NO: 1) and NU0220305 (SEQ ID NO: 2) on *Cucumis melo* Linkage Group 6 of the ICuGI Public Consensus Genetic Map.

embodiment 35. The *Cucumis melo* seed of embodiment 33, wherein said homozygous red flesh allele comprises a TT nucleotide sequence identifiable using a nucleic acid probe having a nucleic acid sequence of SEQ ID NO: 5 or 6.

embodiment 36. The *Cucumis melo* seed of embodiment 33, wherein said homozygous red flesh allele comprises a TT nucleotide sequence identifiable using a nucleic acid probe having a nucleic acid sequence of SEQ ID NO:17 or 18.

embodiment 37. The *Cucumis melo* seed of any one of embodiment s 26 to 33, wherein a plant grown from said seed produces a mature fruit comprising total carotenes greater than a mature fruit obtained from an isogenic plant lacking said homozygous red flesh allele on *Cucumis melo* Linkage Group 6 of the ICuGI Public Consensus Genetic Map grown under similar conditions.

embodiment 38. The *Cucumis melo* seed of any one of embodiment s 26 to 37, wherein a plant grown from said seed produces a mature fruit comprising greater than 15 parts per million more total carotenes than that of a mature fruit obtained from an isogenic plant lacking said homozygous red flesh allele on *Cucumis melo* Linkage Group 6 of the ICuGI Public Consensus Genetic Map grown under similar conditions.

embodiment 39. The *Cucumis melo* seed of any one of embodiment s 26 to 38, wherein a plant grown from said seed produces a mature fruit comprising greater than 20% more total carotenes than that of a mature fruit obtained from an isogenic plant lacking said homozygous red flesh allele on *Cucumis melo* Linkage Group 6 of the ICuGI Public Consensus Genetic Map grown under similar conditions.

embodiment 40. The *Cucumis melo* seed of any one of embodiment s 26 to 39, wherein a plant grown from said seed comprises at least one allele of an earliness locus on *Cucumis melo* Linkage Group 6 of the ICuGI Public Consensus Genetic Map.

embodiment 41. The *Cucumis melo* seed of embodiment 40, wherein said earliness allele is located in a genomic region flanked by nucleic acid markers NU0220305 (SEQ ID NO: 2) and NU0243432 (SEQ ID NO: 3) on *Cucumis melo* Linkage Group 6 of the ICuGI Public Consensus Genetic Map.

embodiment 42. The *Cucumis* melo seed of embodiment 40, wherein said earliness allele comprises a C nucleotide sequence identifiable using a nucleic acid probe having a nucleic acid sequence of SEQ ID NO: 9 or 10.

embodiment 43. The *Cucumis melo* seed of embodiment 40, wherein said earliness allele comprises a G nucleotide sequence identifiable using a nucleic acid probe having a nucleic acid sequence of SEQ ID NO: 13 or 14.

embodiment 44. The *Cucumis melo* seed of embodiment 40, wherein a plant grown from said seed further comprises a fruit that reaches peak Brix accumulation at least three days earlier than a fruit obtained from an isogenic plant lacking said at least one allele of an earliness locus on *Cucumis melo* Linkage Group 6 of the ICuGI Public Consensus Genetic Map grown under similar conditions.

embodiment 45. A method for detecting a red flesh locus linked to an earliness locus on *Cucumis melo* Linkage Group 6 of the ICuGI Public Consensus Genetic Map in a *Cucumis melo* plant comprising,
  a. obtaining at least one progeny seed from a cross comprising at least one *Cucumis melo* plant comprising a trait locus for red flesh linked to a trait locus for earliness on *Cucumis melo* Linkage Group 6 of the ICuGI Public Consensus Genetic Map;
  b. assaying said at least one progeny seed or a plant grown therefrom of step a) for the presence of at least one red flesh allele and at least one allele of an earliness locus; and
  c. detecting at least one *Cucumis melo* seed or a plant grown therefrom of step b) comprising a red flesh allele linked to an earliness allele.

embodiment 46. The method of embodiment 45, wherein said assaying comprises identifying said red flesh allele with a T nucleotide sequence using a nucleic acid probe having a nucleic acid sequence of SEQ ID NO: 5 or 6.

embodiment 47. The method of embodiment 45 or 46, wherein said assaying comprises using a genetic marker sequence within 5 cM or less of SEQ ID NO: 5 or 6.

embodiment 48. The method of any one of embodiment s 45 to 47, wherein said red flesh allele comprises a T nucleotide sequence identifiable using a nucleic acid probe having a nucleic acid sequence of SEQ ID NO:17 or 18.

embodiment 49. The method of any one of embodiment s 45 to 48, wherein said assaying comprises using a genetic marker sequence within 5 cM or less of SEQ ID NO:17 or 18.

embodiment 50. The method of any one of embodiment s 45 to 49, wherein said assaying comprises identifying said earliness allele with a C nucleotide sequence using a nucleic acid probe having a nucleic acid sequence of SEQ ID NO:9 or 10.

embodiment 51. The method of any one of embodiment s 45 to 50, wherein said assaying comprises using a genetic marker sequence within 5 cM or less of SEQ ID NO:9 or 10.

embodiment 52. The method of any one of embodiment s 45 to 51, wherein said assaying comprises identifying said earliness allele with a G nucleotide sequence identifiable using a nucleic acid probe having a nucleic acid sequence of SEQ ID NO:13 or 14.

embodiment 53. The method of any one of embodiment s 45 to 52, wherein said assaying comprises using a genetic marker sequence within 5 cM or less of SEQ ID NO: 13 or 14.

embodiment 54. The method of any one of embodiment s 45 to 53, wherein said *Cucumis melo* plant comprising said trait locus for red flesh linked to said trait locus for earliness trait is *Cucumis melo* cultivar CHA-ZA15-0014AN, a representative sample seed of *Cucumis melo* cultivar CHA-ZA15-0014AN having been deposited with the ATCC under ATCC Accession No. PTA-124202.

embodiment 55. The method of any one of embodiment s 45 to 54, wherein assaying the *Cucumis melo* plant comprises PCR, single strand conformational polymorphism analysis, denaturing gradient gel electrophoresis, cleavage fragment length polymorphism analysis, TAQMAN assay, or DNA sequencing.

embodiment 56. A method of producing a *Cucumis melo* plant comprising,
  a. planting a *Cucumis melo* seed; and
  b. growing said seed into a *Cucumis melo* plant wherein said *Cucumis melo* plant comprises a fruit having red flesh with a hue angle between 55° and 63° and a trait locus for red flesh linked to a trait locus for earliness on *Cucumis melo* Linkage Group 6 of the ICuGI Public Consensus Genetic Map.

embodiment 57. The method of embodiment 56, wherein said trait locus for red flesh comprises a homozygous red flesh allele located in a genomic region flanked by nucleic acid markers NCMEL0085795265 (SEQ ID NO: 1) and NU0220305 (SEQ ID NO: 2) on *Cucumis melo* Linkage Group 6 of the ICuGI Public Consensus Genetic Map.

embodiment 58. The method of embodiment 56 or 57, wherein said homozygous red flesh allele comprises a TT nucleotide sequence identifiable using a nucleic acid probe having a nucleic acid sequence of SEQ ID NO: 5 or 6.

embodiment 59. The method of any one of embodiment s 56 to 58, wherein said homozygous red flesh allele comprises a TT nucleotide sequence identifiable using a nucleic acid probe having a nucleic acid sequence of SEQ ID NO:17 or 18.

embodiment 60. The method of any one of embodiment s 56 to 59, wherein said *Cucumis melo* plant comprises at least one allele of an earliness locus located in a genomic region flanked by nucleic acid markers NU0220305 (SEQ ID NO: 2) and NU0243432 (SEQ ID NO: 3) on *Cucumis melo* Linkage Group 6 of the ICuGI Public Consensus Genetic Map.

embodiment 61. The method of embodiment 60, wherein said earliness allele comprises a C nucleotide sequence identifiable using a nucleic acid probe having a nucleic acid sequence of SEQ ID NO: 9 or 10.

embodiment 62. The method of embodiment 60, wherein said earliness allele comprises a G nucleotide sequence identifiable using a nucleic acid probe having a nucleic acid sequence of SEQ ID NO: 13 or 14.

embodiment 63. The method of embodiment 56, wherein said seed is a progeny seed from a cross comprising at least one *Cucumis melo* plant having a trait locus for red flesh linked to a trait locus for earliness on *Cucumis melo* Linkage Group 6 of the ICuGI Public Consensus Genetic Map.

embodiment 64. The method of embodiment 56, wherein said seed is a progeny seed from a cross comprising at least one *Cucumis melo* plant of cultivar CHA-ZA15-0014AN, a representative sample seed of *Cucumis melo* cultivar CHA-ZA15-0014AN having been deposited with the ATCC under ATCC Accession No. PTA-124202.

embodiment 65. The method of any one of embodiments 56 to 64, wherein said progeny seed is a $F_1$ progeny seed.

embodiment 66. The method of any one of embodiments 55 to 65, wherein said seed is capable of producing *Cucumis melo* cultivar CHA-ZA15-0014AN, a representative sample seed of *Cucumis melo* cultivar CHA-ZA15-0014AN having been deposited with the ATCC under ATCC Accession No. PTA-124202.

embodiment 67. A method of producing a *Cucumis melo* plant, or part thereof, comprising,
 a. planting a *Cucumis melo* seed;
 b. growing a first *Cucumis melo* plant comprising a trait locus for a red flesh allele linked to a trait locus for an earliness allele on *Cucumis melo* Linkage Group 6 of the ICuGI Public Consensus Genetic Map;
 c. crossing said first *Cucumis melo* plant to a second *Cucumis melo* plant, wherein said second *Cucumis melo* plant lacks said trait locus for a red flesh allele linked to a trait locus for an earliness allele on *Cucumis melo* Linkage Group 6 of the ICuGI Public Consensus Genetic Map; and
 d. selecting a progeny *Cucumis melo* plant, or part thereof, comprising a trait locus for a red flesh allele linked to said trait locus for an earliness allele on *Cucumis melo* Linkage Group 6 of the ICuGI Public Consensus Genetic Map.

embodiment 68. The method of embodiment 67, wherein said red flesh allele is located in a genomic region flanked by nucleic acid markers NCMEL0085795265 (SEQ ID NO: 1) and NU0220305 (SEQ ID NO: 2) on *Cucumis melo* Linkage Group 6 of the ICuGI Public Consensus Genetic Map and said earliness allele is located in a genomic region flanked by nucleic acid markers NU0220305 (SEQ ID NO: 2) and NU0243432 (SEQ ID NO: 3) on *Cucumis melo* Linkage Group 6 of the ICuGI Public Consensus Genetic Map.

embodiment 69. The method of embodiment 67 or 68, wherein said red flesh allele comprises a T nucleotide sequence identifiable using a nucleic acid probe having a nucleic acid sequence of SEQ ID NO: 5 or 6.

embodiment 70. The method of any one of embodiments 67 to 69, wherein said red flesh allele comprises a T nucleotide sequence identifiable using a nucleic acid probe having a nucleic acid sequence of SEQ ID NO:17 or 18.

embodiment 71. The method of embodiment 70, wherein said earliness allele comprises a C nucleotide sequence identifiable using a nucleic acid probe having a nucleic acid sequence of SEQ ID NO: 9 or 10.

embodiment 72. The method of embodiment 70, wherein said earliness allele comprises a G nucleotide sequence identifiable using a nucleic acid probe having a nucleic acid sequence of SEQ ID NO: 13 or 14.

embodiment 73. The method of embodiment 70, further comprising harvesting seed from a fruit of said selected progeny *Cucumis melo* plant.

embodiment 74. The method of embodiment 72, wherein said seed is a progeny seed from a cross comprising at least one *Cucumis melo* plant of cultivar CHA-ZA15-0014AN, a representative sample seed of *Cucumis melo* cultivar CHA-ZA15-0014AN having been deposited with the ATCC under ATCC Accession No. PTA-124202.

embodiment 75. The method of any one of embodiments 67 to 74, wherein said second *Cucumis melo* plant comprises a trait locus for a red flesh allele on *Cucumis melo* Linkage Group 6 of the ICuGI Public Consensus Genetic Map.

embodiment 76. The method of any one of embodiments 67 to 75, wherein said progeny seed is a $F_1$ progeny seed.

embodiment 77. The method of any one of embodiments 67 to 76, wherein said first *Cucumis melo* plant is a *Cucumis melo* cultivar CHA-ZA15-0014AN or is derived from a *Cucumis melo* cultivar CHA-ZA15-0014AN, a representative sample seed of *Cucumis melo* cultivar CHA-ZA15-0014AN having been deposited with the ATCC under ATCC Accession No. PTA-124202.

embodiment 78. The method of any one of embodiments 67 to 77, wherein said second *Cucumis melo* plant is an elite variety of *Cucumis melo*.

embodiment 79. The method of any one of embodiments 67 to 78, further comprising backcrossing said progeny *Cucumis melo* plant to said first *Cucumis melo* plant.

embodiment 80. The *Cucumis melo* plant, or part thereof, of any one of embodiments 1 to 25, wherein said part is a fruit comprising an average Brix content of at least 9° Brix at maturity.

embodiment 81. The *Cucumis melo* plant, or part thereof, of any one of embodiments 1 to 25, wherein said part is a fruit comprising an average Brix content of at least 11° Brix at maturity.

embodiment 82. A method of producing a *Cucumis melo* plant, or part thereof, comprising,
 a. growing a first *Cucumis melo* plant comprising a trait locus for a red flesh allele on *Cucumis melo* Linkage Group 6 of the ICuGI Public Consensus Genetic Map,
 b. crossing said first *Cucumis melo* plant to a second *Cucumis melo* plant comprising a trait locus for an earliness allele on *Cucumis melo* Linkage Group 6 of the ICuGI Public Consensus Genetic Map,
 c. selecting a first progeny *Cucumis melo* plant comprising a red flesh allele and an earliness allele on *Cucumis melo* Linkage Group 6 of the ICuGI Public Consensus Genetic Map;
 d. harvesting progeny seed from a fruit of said selected first progeny *Cucumis melo* plant;
 e. performing a second cross, wherein parents of said second cross are selected from the group consisting of a *Cucumis melo* plants grown from said first progeny seed and said first *Cucumis melo* plant; and
 f. selecting a second progeny *Cucumis melo* plant from said second cross, said second progeny *Cucumis melo* plant comprising a trait locus for a red flesh allele linked to a trait locus for an earliness allele on *Cucumis melo* Linkage Group 6 of the ICuGI Public Consensus Genetic Map.

embodiment 83. The method of embodiment 82, further comprising harvesting seed from a fruit of said selected first or second progeny *Cucumis melo* plant from said second cross.

embodiment 84. The method of embodiment 82 or 83, wherein said red flesh allele is located in a genomic region flanked by nucleic acid markers NCMEL0085795265 (SEQ ID NO: 1) and NU0220305 (SEQ ID NO: 2) on *Cucumis melo* Linkage Group 6 of the ICuGI Public Consensus Genetic Map and said earliness allele is located in a genomic region flanked by nucleic acid markers NU0220305 (SEQ ID NO: 2) and NU0243432 (SEQ ID NO: 3) on *Cucumis melo* Linkage Group 6 of the ICuGI Public Consensus Genetic Map.

embodiment 85. The method of any one of embodiments 82 to 84, wherein said first *Cucumis melo* plant comprises a trait locus with a homozygous red flesh allele on *Cucumis melo* Linkage Group 6 of the ICuGI Public Consensus Genetic Map, said second *Cucumis melo* plant comprises a trait locus with a homozygous earliness allele on *Cucumis melo* Linkage Group 6 of the ICuGI Public Consensus Genetic Map, or said first *Cucumis melo* plant comprises a trait locus with a homozygous red flesh allele on *Cucumis melo* Linkage Group 6 of the ICuGI Public Consensus Genetic Map and said second *Cucumis melo* plant comprises a trait locus with a homozygous earliness allele on *Cucumis melo* Linkage Group 6 of the ICuGI Public Consensus Genetic Map.

embodiment 86. The method of any one of embodiments 82 to 86, wherein said progeny *Cucumis melo* plant or seed is an $F_1$ progeny plant or seed.

embodiment 87. The method of any one of embodiments 82 to 86, further comprising backcrossing said progeny *Cucumis melo* plant or a plant grown from said progeny *Cucumis melo* seed to said first *Cucumis melo* plant or said second *Cucumis melo* plant.

embodiment 88. The method of embodiment 82 or 87, wherein said red flesh allele comprises a T nucleotide sequence identifiable using a nucleic acid probe having a nucleic acid sequence of SEQ ID NO: 5 or 6.

embodiment 89. The method of any one of embodiment s 82 to 88, wherein said red flesh allele comprises a T nucleotide sequence identifiable using a nucleic acid probe having a nucleic acid sequence of SEQ ID NO:17 or 18.

embodiment 90. The method of embodiment 89, wherein said earliness allele comprises a C nucleotide sequence identifiable using a nucleic acid probe having a nucleic acid sequence of SEQ ID NO: 9 or 10.

embodiment 91. The method of embodiment 89, wherein said earliness allele comprises a G nucleotide sequence identifiable using a nucleic acid probe having a nucleic acid sequence of SEQ ID NO: 13 or 14.

embodiment 92. A method for detecting a red flesh allele linked to an earliness allele on *Cucumis melo* Linkage Group 6 of the ICuGI Public Consensus Genetic Map in a *Cucumis melo* plant comprising,
  a. obtaining at least one *Cucumis melo* plant;
  b. assaying said at least one plant of step a) for the presence of a red flesh allele and an earliness allele on *Cucumis melo* Linkage Group 6 of the ICuGI Public Consensus Genetic Map; and
  c. detecting at least one *Cucumis melo* plant of step b) comprising a red flesh allele linked to an earliness allele on *Cucumis melo* Linkage Group 6 of the ICuGI Public Consensus Genetic Map.

embodiment 93. The method of embodiment 92, wherein said assaying comprises identifying said red flesh allele with a T nucleotide sequence using a nucleic acid probe having a nucleic acid sequence of SEQ ID NO:5 or 6.

embodiment 94. The method of embodiment 92 or 93, wherein said assaying comprises using a genetic marker sequence within 5 cM or less of SEQ ID NO:5 or 6.

embodiment 95. The method of any one of embodiments 92 to 94, wherein said red flesh allele comprises a T nucleotide sequence identifiable using a nucleic acid probe having a nucleic acid sequence of SEQ ID NO:17 or 18.

embodiment 96. The method of any one of embodiments 92 to 95, wherein said assaying comprises using a genetic marker sequence within 5 cM or less of SEQ ID NO:17 or 18.

embodiment 97. The method of any one of embodiments 92 to 96, wherein said assaying comprises identifying said earliness allele with a C nucleotide sequence using a nucleic acid probe having a nucleic acid sequence of SEQ ID NO:9 or 10.

embodiment 98. The method of any one of embodiments 92 to 97, wherein said assaying comprises using a genetic marker sequence within 5 cM or less of SEQ ID NO:9 or 10.

embodiment 99. The method of any one of embodiments 92 to 98, wherein said assaying comprises identifying said earliness allele with a G nucleotide sequence identifiable using a nucleic acid probe having a nucleic acid sequence of SEQ ID NO:13 or 14.

embodiment 100. The method of any one of embodiments 92 to 99, wherein said assaying comprises using a genetic marker sequence within 5 cM or less of SEQ ID NO:13 or 14.

embodiment 101. A method for detecting a red flesh allele linked to an earliness allele on *Cucumis melo* Linkage Group 6 of the ICuGI Public Consensus Genetic Map in a *Cucumis melo* plant comprising,
  a. obtaining at least one *Cucumis melo* plant;
  b. assaying said at least one plant of step a) for the presence of a red flesh allele and an earliness allele on *Cucumis melo* Linkage Group 6 of the ICuGI Public Consensus Genetic Map, wherein said assaying comprises identifying said red flesh allele with a T nucleotide sequence using a nucleic acid probe having a nucleic acid sequence of SEQ ID NO:5 or 6; and
  c. detecting at least one *Cucumis melo* plant of step b) comprising a red flesh allele linked to an earliness allele on *Cucumis melo* Linkage Group 6 of the ICuGI Public Consensus Genetic Map.

embodiment 102. The method of embodiment 101, wherein said assaying comprises using a genetic marker sequence within 5 cM or less of SEQ ID NO:5 or 6.

embodiment 103. The method of embodiments 101 or 102, wherein said red flesh allele comprises a T nucleotide sequence identifiable using a nucleic acid probe having a nucleic acid sequence of SEQ ID NO:17 or 18.

embodiment 104. The method of any one of embodiments 101 to 103, wherein said assaying comprises using a genetic marker sequence within 5 cM or less of SEQ ID NO:17 or 18.

embodiment 105. The method of any one of embodiments 101 to 104, wherein said assaying comprises identifying said earliness allele with a C nucleotide sequence using a nucleic acid probe having a nucleic acid sequence of SEQ ID NO:9 or 10.

embodiment 106. The method of any one of embodiments 101 to 105, wherein said assaying comprises using a genetic marker sequence within 5 cM or less of SEQ ID NO:9 or 10.

embodiment 107. The method of any one of embodiments 101 to 106, wherein said assaying comprises identifying said earliness allele with a G nucleotide sequence identifiable using a nucleic acid probe having a nucleic acid sequence of SEQ ID NO:13 or 14.

embodiment 108. The method of any one of embodiments 101 to 107, wherein said assaying comprises using a genetic marker sequence within 5 cM or less of SEQ ID NO:13 or 14.

embodiment 109. A method for detecting a red flesh allele linked to an earliness allele on *Cucumis melo* Linkage Group 6 of the ICuGI Public Consensus Genetic Map in a *Cucumis melo* plant comprising, a. obtaining at least one *Cucumis melo* plant;

b. assaying said at least one plant of step a) for the presence of a red flesh allele and an earliness allele on *Cucumis melo* Linkage Group 6 of the ICuGI Public Consensus Genetic Map, wherein said red flesh allele comprises a T nucleotide sequence identifiable using a nucleic acid probe having a nucleic acid sequence of SEQ ID NO:17 or 18; and c. detecting at least one *Cucumis melo* plant of step b) comprising a red flesh allele linked to an earliness allele on *Cucumis melo* Linkage Group 6 of the ICuGI Public Consensus Genetic Map.

embodiment 110. The method of embodiment 109, wherein said assaying comprises using a genetic marker sequence within 5 cM or less of SEQ ID NO:17 or 18.

embodiment 111. The method of embodiments 109 or 110, wherein said assaying comprises identifying said red flesh allele with a T nucleotide sequence using a nucleic acid probe having a nucleic acid sequence of SEQ ID NO:5 or 6.

embodiment 112. The method of any one of embodiments 109 to 111, wherein said assaying comprises using a genetic marker sequence within 5 cM or less of SEQ ID NO:5 or 6.

embodiment 113. The method of any one of embodiments 109 to 112, wherein said assaying comprises identifying said earliness allele with a C nucleotide sequence using a nucleic acid probe having a nucleic acid sequence of SEQ ID NO:9 or 10.

embodiment 114. The method of any one of embodiments 109 to 113, wherein said assaying comprises using a genetic marker sequence within 5 cM or less of SEQ ID NO:9 or 10.

embodiment 115. The method of any one of embodiments 109 to 114, wherein said assaying comprises identifying said earliness allele with a G nucleotide sequence identifiable using a nucleic acid probe having a nucleic acid sequence of SEQ ID NO:13 or 14.

embodiment 116. The method of any one of embodiments 109 to 115, wherein said assaying comprises using a genetic marker sequence within 5 cM or less of SEQ ID NO:13 or 14.

embodiment 117 The method of any one of embodiments 92 to 116, wherein said assaying comprises assaying a haploid *Cucumis melo* cell.

Having now generally described the disclosure, the same will be more readily understood through reference to the following examples that are provided by way of illustration, and are not intended to be limiting of the present disclosure, unless specified.

Each patent cited herein is herein incorporated by reference in its entirety.

EXAMPLES

Example 1. Plant Growth Conditions

*Cucumis melo* plants used in this study are grown in the field. Field studies are conducted in the summer months in Woodland, CA In the field, plants are arranged in a random complete block design with at least two replications of plots containing 30 plants each unless specified otherwise.

Example 2. Phenotypic Measurements a) Brix Measurements

Brix is measured in Degree Brix (° B) using a refractometer or density meter according to manufacturer's instructions (e.g. Refracto 30PX, Mettler-Toledo, Columbus, OH) to determine the percent of total soluble solids in a fruit.

Female flowers are flagged at anthesis as time $T_0$. One to six fruit are measured for each replication at each timepoint dependent on fruit availability. Brix is measured at 21, 25, 28, 32, 36, and 39 days post anthesis (DPA) to capture the accumulation of Brix over the typical period that *Cucumis melo* (Charentais) reaches maturity. Data is analyzed using JMP software (SAS, Cary, NC) using rep as a random effect. The Least Square Mean (LSM) of Brix measurements is calculated for each entry and correlated with genotyping of selected marker loci.

b) Carotenoid Measurements

Carotenoid profile analysis of melon puree is conducted by high performance liquid chromatography (HPLC) using reverse phase separation and Diode Array Detection (DAD) at 450 nm. Extraction is performed in organic solvent. Sample preparation consists of blended material without straining or dilution until extraction. Blended materials are maintained frozen (−20° C.) until ready for extraction. Extracts are analyzed within 24 hours of extraction using low light and cold temperature conditions. Quantitation is performed via computerized integrators and commercial reference materials are used. Ten melons per entry are evaluated individually and LS Means calculated in JMP software (SAS, Cary, NC).

c) Fruit Flesh Color Measurements

Observed color of the fruit is quantified colorimetrically using a Konica Minolta colorimeter according to manufacturer's instructions (e.g. Konica-Minolta® CR-410 Chroma Meter). Hue angle (calculated as the arctangent [atan 2] of color coordinates a and b using a Konica-Minolta® colorimeter in L*a*b* color mode) is descriptive of color. Before color measurements, female flowers are flagged at anthesis as time $T_0$. Average hue measurements are calculated for all mature fruit at 34 to 38 DPA. LSM and Mean Square Differences between groups of hue are calculated in JMP software (SAS, Cary, NC) using rep as a random effects. Average lightness and chroma values are also captured using this method.

Example 3. Quantitative Trait Loci (QTL) Analysis

Phenotypic results including color (hue and lightness) and maturity date are used for QTL analysis of the red flesh mapping populations using the composite interval mapping algorithm implemented in WinCartQTL (Wang et al., 2011) QTL statistics are calculated using QTL cartographer.

Example 4. Development of Earliness and Red Flesh Donor Lines a) Development of the Melon Line "BEST"

"BEST", a line with improved and early Brix accumulation, is used as the donor for the early Brix accumulation trait. A sample seed of *Cucumis melo* line "BEST" has been deposited under ATCC Accession Number PTA-12263. See, U.S. Pat. No. 9,580,724. A BRIX4 QTL is identified in the "BEST" line that is linked to early maturation and confers high Brix accumulation (FIG. 1).

b) Development of the Early Brix Accumulation Donor

Figure 2:
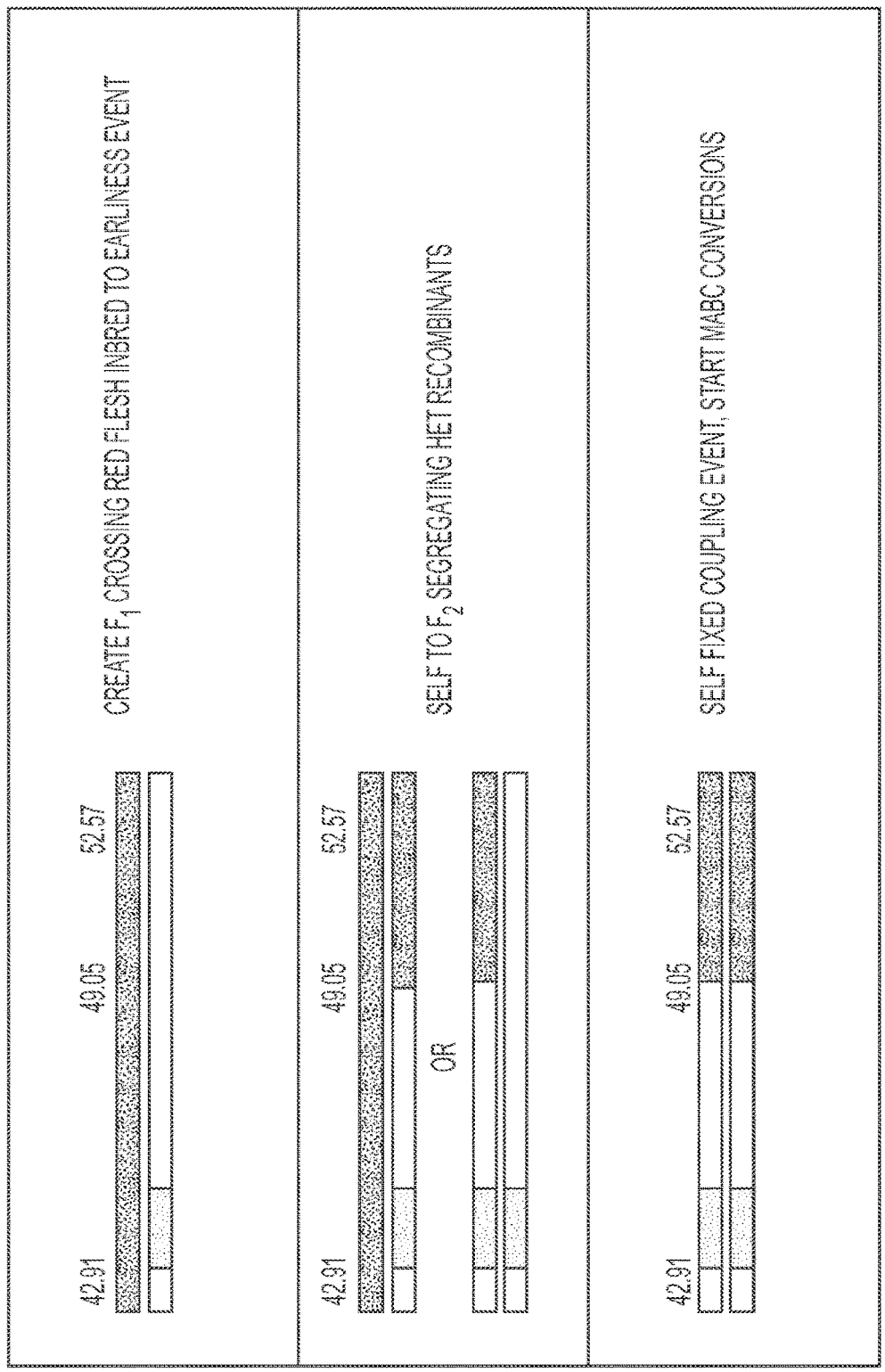
FIG. 2 is a diagram of the crossing steps used in the creation of an earliness and red flesh coupling event. The $F_1$ generation is bred by crossing a red flesh donor (CHA-192-0058-MO) and earliness donor ("BEST" crossed to CHA-192-ONTARIO-AN). Segregating $F_2$ plants are phenotyped and selected. Plants with both red flesh and an earliness phenotype are selfed to fix the coupling event. Genetic map locations are given in cM according to the Monsanto Consensus Genetic Map.

CHA-192-ONTARIO-AN, a late maturing line with high Brix, is crossed to the donor line "BEST" to map the earliness trait within the BRIX4 QTL (FIG. 2). A $BC_3F_2$ (second filial generation of a third backcross) introgression line of CHA-192-ONTARIO-AN with the BRIX4 QTL is selfed to create recombinants across the BRIX4 QTL. Recombinant plants are grown according to Example 1 and Brix accumulation is measured as described in Example 2.

Figure 3:
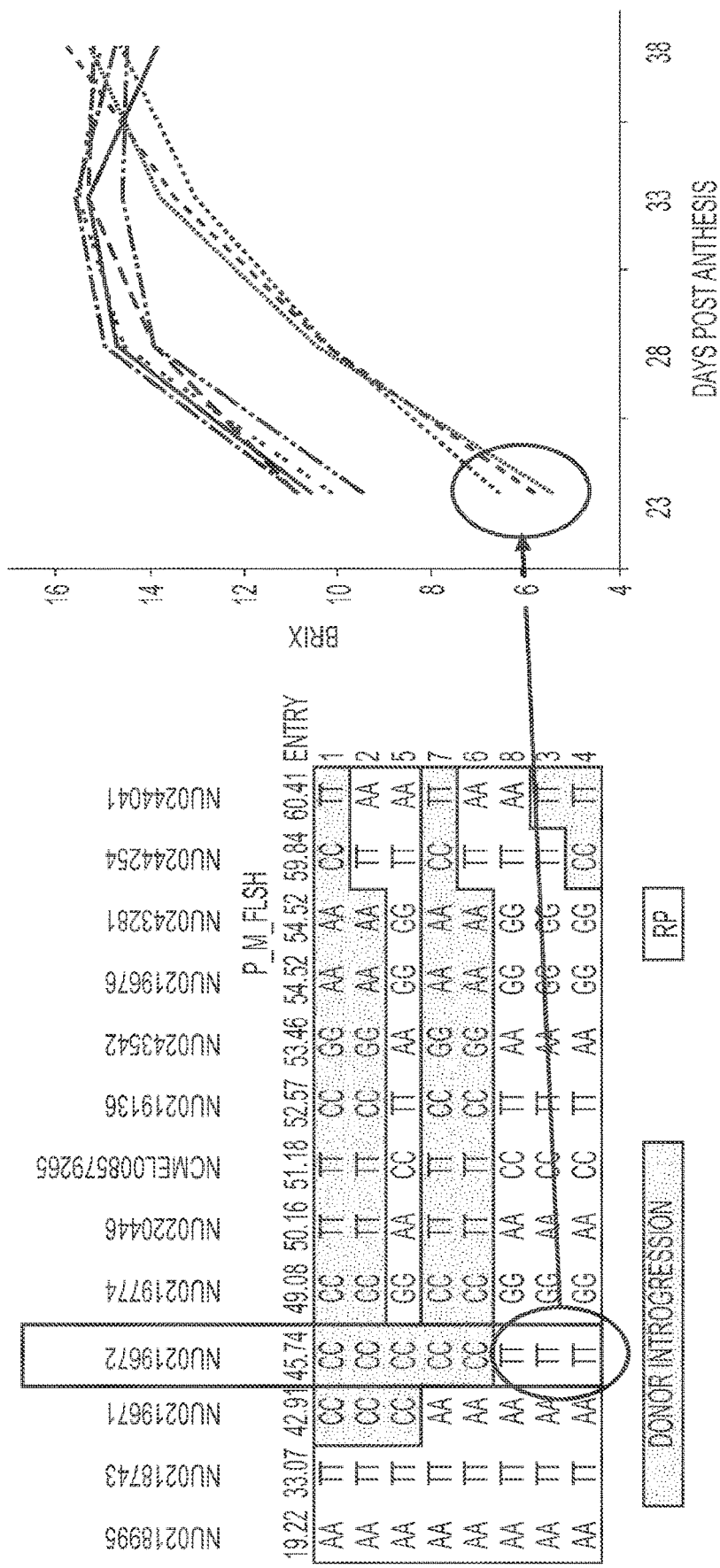
FIG. 3 (left) is a diagram of recombinant haplotypes for eight $BC_3F_3$ plants with the earliness donor ("BEST") allele being a homozygous C nucleotide, "CC", and recurrent parent (CHA-192-ONTARIO-AN) alleles being a homozygous T nucleotide, "TT".

Genetic analysis of the recombinants is conducted as described in Example 3 and places the earliness event on Linkage Group 4 of the Monsanto Consensus Genetic Map between flanking markers NU0243432 (having the nucleotide sequence SEQ ID NO: 3) and NU0220305 (having the nucleotide sequence SEQ ID NO: 2)(See Table 3). One introgression line with significant early Brix accumulation is named the "earliness event" and is used as the earliness donor in a cross to develop plants with red flesh coupled to early Brix accumulation (FIG. 2 and FIG. 4). As shown in FIG. 3, plants with the homozygous parent allele, "TT", at marker NU0219672, with the earliness interval, reach maximum Brix after 38 days. Plants with a homozygous "BEST" allele, "CC", at marker NU0219672 reach maximum Brix after 28 days (FIG. 3). Marker NU0219672 falls into the genetic interval between flanking markers NU0243432 and NU0220305 (See Table 3 and FIG. 3).

TABLE 3

Genetic markers flanking the earliness locus. Map position is according to ICuGI Public Consensus Genetic Map (LG 6).

| MRN | NU0243432 | NU0220305 |
| --- | --- | --- |
| Physical Position | 28346029 | 24876456 |
| Favorable allele | G | C |
| Probe Allele 1 | (SEQ ID NO: 13) CAGTCTTGGATGGAT TT | (SEQ ID NO: 9) CCAAACTTCATCCT CATCC |
| Probe Allele 2 | (SEQ ID NO: 14) AGTCTTGGACGGATT T | (SEQ ID NO: 10) CAAACTTCATCGTCA TCC |
| F Primer Sequence | (SEQ ID NO: 15) GGCACTAGAAATGAG TCCATACGA | (SEQ ID NO: 11) GGTGGTGGCTCGGTT AATGT |
| R Primer Sequence | (SEQ ID NO: 16) GCAACTCAGCCTTCC TCTTCTG | (SEQ ID NO: 12) GGTGGAATTGCGACT CGAAAC | c) Development of the Red Flesh Donor

Preliminary mapping identifies a genetic interval segregating with red flesh between genetic map positions 49.1 cM and 52.6 cM on *Cucumis melo* Linkage Group 4 of the Monsanto Consensus Genetic Map (FIG. 1). Table 4 summarizes three red flesh donor lines, two Charentais and one Italian-type, used to generate mapping populations. Plants are grown as described in Example 1. Hue angle measurements and QTL analysis are performed as described in Examples 2 and 3. The results are presented in FIG. 5A and identify one major QTL for red flesh on *Cucumis melo* Linkage Group 4 of the Monsanto Consensus Genetic Map.

TABLE 4

Mapping populations used to identify a red flesh locus on Cucumis melo Linkage Group 4 of the Monsanto Consensus Genetic Map.

| Red Flesh Donor | Orange Flesh recurrent parent | Mapping date and location | Genetic Data Source |
| --- | --- | --- | --- |
| CHA-192-0058-MO | CHA-38-MAKER-AN | Woodland greenhouse 2012 | BSA of Infinium Fingerprint + Sequence Capture |
| CHA-192-0034-AN | CHA-MEHARI | Woodland greenhouse 2012 | TM markers on Chr 4 + Sequence Capture |
| ITAAZ11-7001MO | ITAAZ13-0038MO | Woodland field 2013 | TM markers on Chr 4 |
| ITAAZ11-7001MO | ITA-188-LIC-MO | Woodland field 2013 | TM markers on Chr 4 |

Figure 5B:
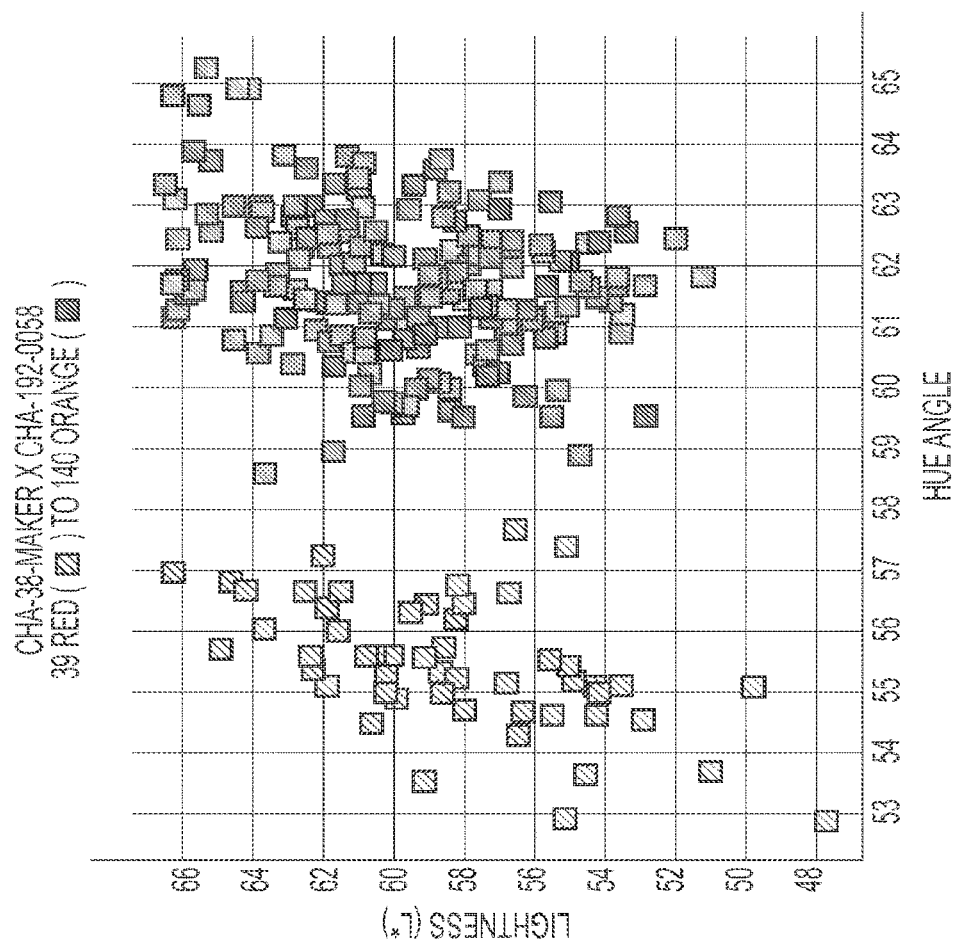
FIG. 5B shows segregation of lines in the mapping populations for orange and red flesh.
Figure 5A:
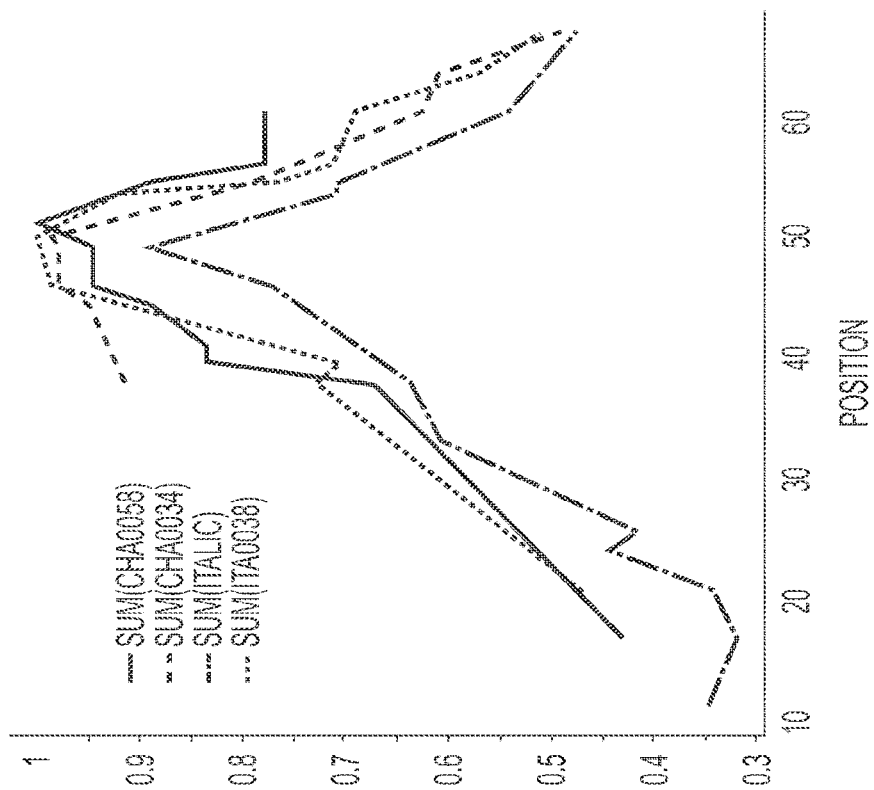
FIG. 5A shows the location of a major QTL for red flesh on *Cucumis melo* Linkage Group 4 of the Monsanto Consensus Genetic Map as found in four mapping populations. The Y-axis shows the frequency of associated red flesh alleles to Hue, where 1 is a perfect association. The X-axis shows the genetic position in cM on Linkage Group 4 of the Monsanto Consensus Genetic Map. Genetic map locations are given in cM according to the Monsanto Consensus Genetic Map.

Flesh color is scored for 179 $F_2$ progeny plants from the CHA-192-0058-MO×CHA-38-MAKER-AN cross grown as described in Example 1 using hue angle measurements as described in Example 2. These measurements demonstrate that the red flesh phenotype segregates recessively in a simple Mendellian 3:1 distribution (FIG. 5B). A selection of red and orange $F_2$ plants from the CHA-192-0058-MO×CHA-38-MAKER-AN cross are used to identify red flesh alleles by Infinium (Illumina, San Diego, CA) fingerprinting followed by Bulk Segregant Analysis (BSA) and sequence capture.

Carotenoid content is correlated with flesh color in *Cucumis melo*. Red flesh color contains more carotenoids than orange flesh color. Plants are grown as described in Example 1 and carotenoid content is measured as described in Example 2. Quantification of β-carotene for the parents of the mapping populations and the two color classes of the $F_2$ populations show that fruit having red flesh contains higher levels of β-carotene compared to fruit with an orange flesh color (Table 5).

TABLE 5

Total β-carotene measurements (ppm—parts per million) for red and orange flesh recurrent parents and $F_2$ progeny.

| Lines | Color Class | β-carotene (ppm) |
| --- | --- | --- |
| CHA-38-MAKER | Orange | 29 |
| CHA-192-0058-MO | Red | 41.6 |
| CHA-38-MAKER × CHA-192-0058-MO $F_2$s | Orange | 30.6 |
| CHA-38-MAKER × CHA-192-0058-MO $F_2$s | Red | 51.2 |
| ZA_Mehari-2 | Orange | 16.4 |
| CHA-192-0034-MO | Red | 35.2 |
| Mehari × CHA-192-0034-MO $F_2$s | Orange | 18.8 |
| Mehari × CHA-192-0034-MO $F_2$s | Red | 34.6 |

The red flesh phenotype is fixed by selfing of the CHA-192-0058-MO×CHA-38-MAKER-AN cross described above. Flesh color is measured for ten $F_6$ recombinants in the CHA-38-MAKER-AN×CHA-192-0058-MO mapping population with five replications to confirm transmission of the phenotype. Plants are grown as described in Example 1 and color measurements are performed as described in Example 2. As shown in FIG. 6, lines with a homozygous C nucleotide, "CC", at marker NCMEL008579265 have CHA-38-MAKER-AN alleles and a hue angle of greater than 63, which correlates to orange flesh color. Likewise, lines with a homozygous T nucleotide, "TT", at marker NCMEL008579265 have CHA-192-0058-MO alleles and a hue angle of between 55-63 degrees correlating with red flesh color.

Genotypic analysis in the $F_5$ recombinant plants further delimits the red flesh locus to an interval identifiable by the flanking markers NCMEL008579265 (having the nucleotide sequence of SEQ ID NO: 1) and marker NU0220305 (having the nucleotide sequence of SEQ ID NO: 2) (Table 6). A homozygous T allele, "TT", at marker NCMEL008579265 co-segregates with the red flesh donor and progeny lines with the red flesh trait. The CHA-192-0058-MO line is used as the red flesh donor in a cross to develop plants with red flesh coupled to early Brix accumulation (FIG. 2).

TABLE 6

Genetic markers flanking the red flesh locus.
Map position is according to ICuGI public
consensus genetic map.

| MRN | NU0220305 | NCMEL008579265 |
|---|---|---|
| Physical Position | 24876456 | 22825883 |
| Favorable allele | C | T |
| Probe Allele 1 | (SEQ ID NO: 9) CCAAACTTCATCCTCATCC | (SEQ ID NO: 5) AAAACCATTGAATCAAC |
| Probe Allele 2 | (SEQ ID NO: 10) CAAACTTCATCGTCATCC | (SEQ ID NO: 6) AAAAACCATTAAATCAAC |
| F Primer Sequence | (SEQ ID NO: 11) GGTGGTGGCTCGGTTAATGT | (SEQ ID NO: 7) CAATCATATGGTCAATAAAATGTATGTTCCGT |
| R Primer Sequence | (SEQ ID NO: 12) GGTGGAATTGCGACTCGAAAC | (SEQ ID NO: 8) GTTTAGAATGGAATGGCCTGTGTAC |

Example 4. Preparation of Early Red *Cucumis melo* Plants

The "earliness event" donor ("BEST" conversion of the CHA-192-ONTARIO-AN background) is crossed to the red flesh donor CHA-192-0058-MO to generate $F_1$ plants (FIG. 2b). The $F_1$ generation plants are selfed to prepare $F_2$ plants and are grown in the field as described in Example 1 together with recurrent parents and control plants: CHA-192-ONTARIO-AN, CHA-192-0058-MO, and the "earliness event". The LSM of Brix measurements is calculated for each entry as described in Example 2. Brix measurements are summarized with genotyping results of selected marker loci across the interval in FIG. 7 and FIG. 8.

Figure 7A:
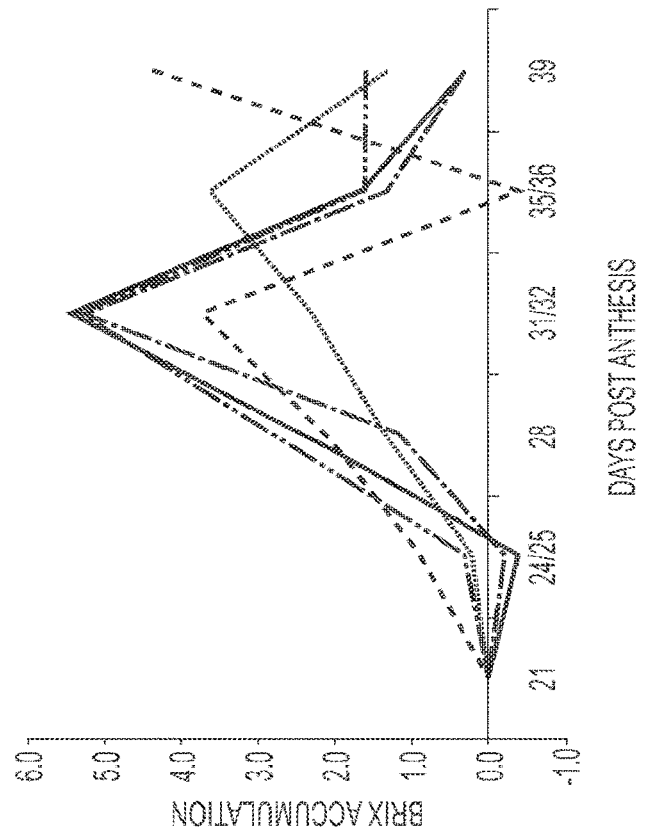
FIG. 7A shows lines with early Brix accumulation.
Figure 7B:
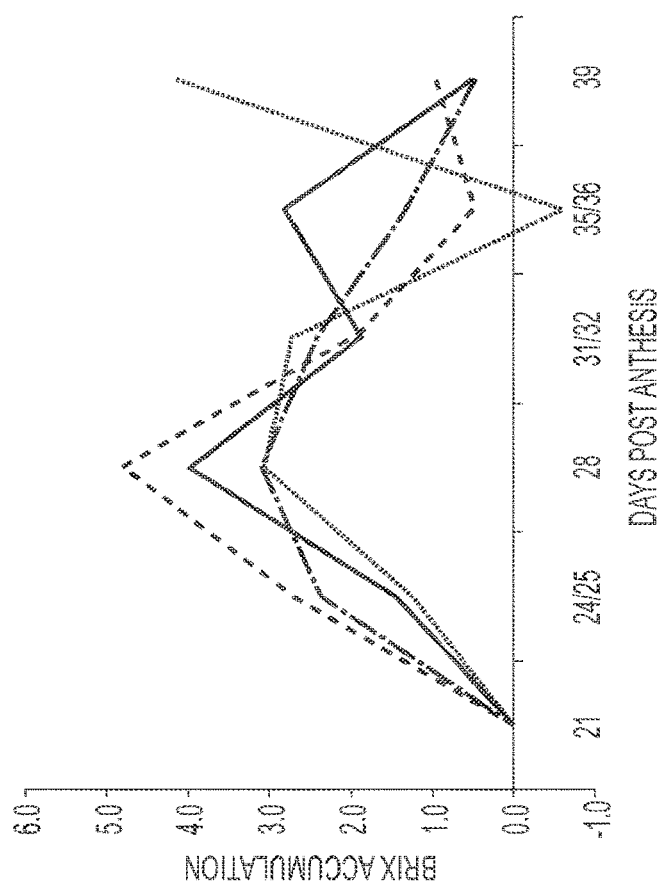
FIG. 7B shows lines with late Brix accumulation.

Increases in degrees Brix over time are shown for eight recombinants and controls (FIG. 7). Total Brix accumulation at a given DPA is shown in FIG. 8. As shown in FIG. 7 and FIG. 8, two categories of Brix accumulation are identified: early Brix accumulation is defined by a peak in accumulation at 28 DPA (FIG. 7A) and late Brix accumulation is defined by a peak in accumulation after 31 DPA (FIG. 7B). A plant with an early Brix accumulation phenotype shows an increase of at least 1° Brix by 24 DPA where the Brix level is defined as zero at 21 DPA. A plant with a late Brix accumulation phenotype shows an increase of at least 1° Brix after 26 DPA, typically by 28 DPA. As shown in FIG. 7 and FIG. 8, the "earliness event" introgression line shows early Brix accumulation. The red flesh donor, CHA-192-0058-MO, and the recurrent parent of the earliness event introgression, CHA-192-ONATARIO-AN, both show late Brix accumulation (FIG. 7 and FIG. 8). The absence of earliness event alleles, a G nucleotide at marker NU0243432 or a C nucleotide at marker NU0220305, is notable in the recombinant lines with late Brix accumulation (FIG. 7 and FIG. 8).

Development of Line CHA-ZA15-0014AN

Figure 10:
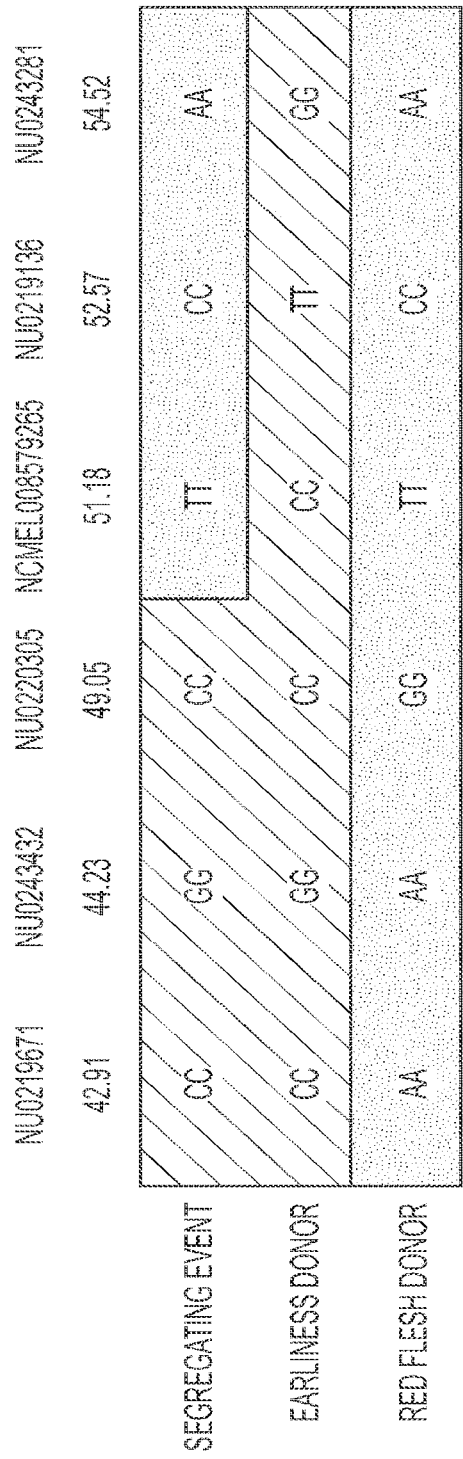
FIG. 10 is a diagram showing the genetic haplotype of markers in $F_2$ recombinants of the coupling cross. The segregating event (with the coupling haplotype), the earliness donor ("BEST"), and the red flesh donor (CHA-192-0058-MO) are shown. Genetic map locations are given in cM according to the Monsanto Consensus Genetic Map.

One line in this study segregated for both red and orange flesh color (highlighted in FIG. 9). This line is fixed for red flesh alleles at NCMEL008579265, but is heterozygous upstream of that marker. Since the lines trialed in the field are $F_2$, the segregation of flesh color is due to different recombination sites between marker NU0220305 and marker NCMEL008579265 in different plants within the same family. In order to recover the coupled event, plants fixed for earliness and heterozygous (CT) at marker NCMEL008579265 are selected and selfed. Progeny of the heterozygous segregating lines described above are scored for flesh color and genotyped for the coupling event haplotype (FIG. 10). The coupling event is identified as CHA-ZA15-0014AN. The line is selfed further and selected to fix desired secondary traits.

Figure 11:
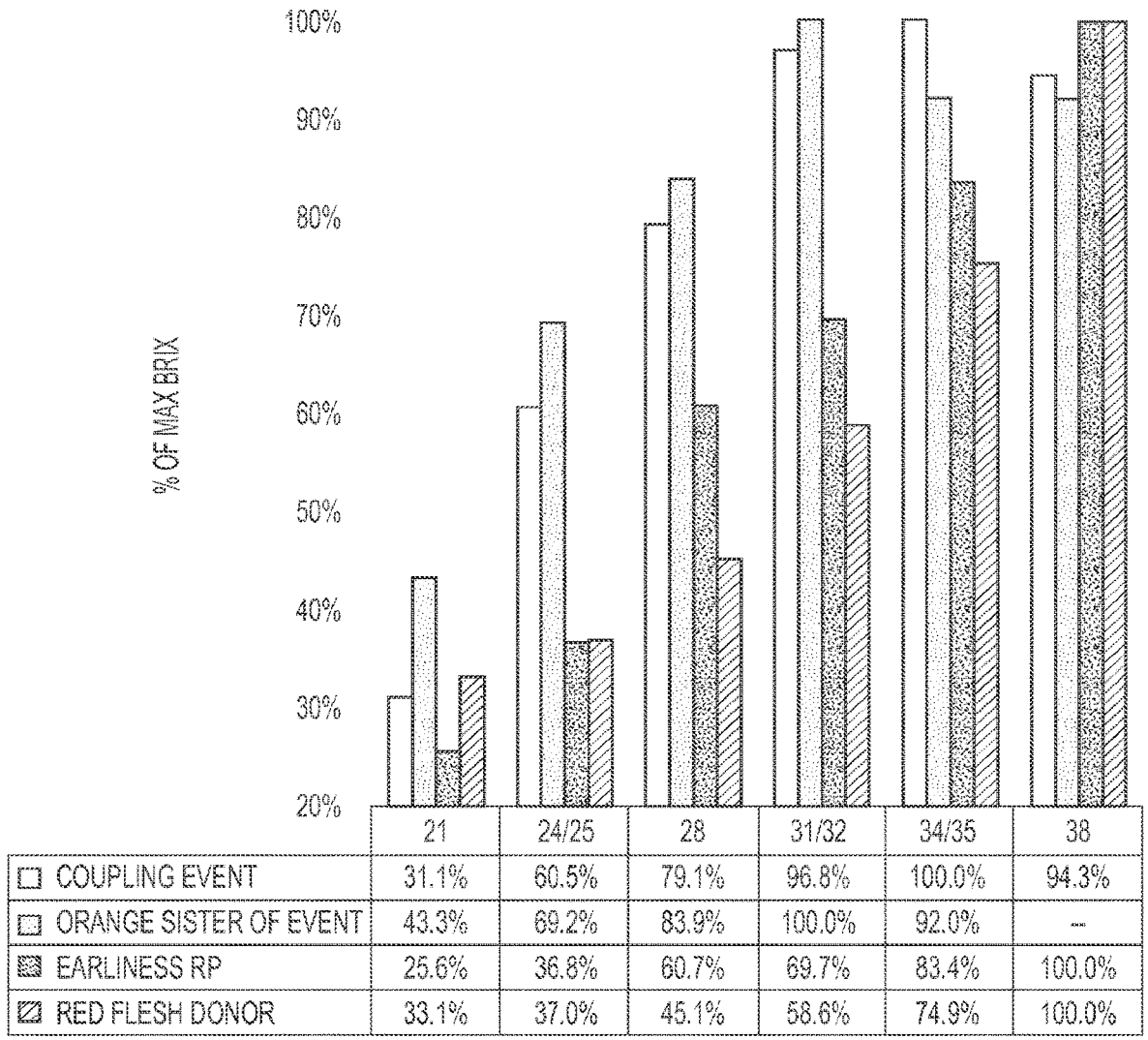
FIG. 11 is a graph of values for Brix accumulation in $F_5$ plants of the CHA-ZA15-0014AN line, indicated as percentage of maximum Brix (Brix at time point/Maximum Brix observed for entry) shown for each time point (DPA). The orange sister of the event, earliness recurrent parent (CHA-192-ONTARIO-AN), and red flesh donor (CHA-192-0058-MO) are shown for comparison.

Example 5. Confirmation of Transmission of the Earliness/Red Flesh Phenotype on *Cucumis melo* Linkage Group 4 of the Monsanto Consensus Genetic Map Early Brix accumulation in the line CHA-ZA15-0014AN is evaluated in the field alongside the red flesh donor CHA-192-0058-MO, earliness recurrent parent CHA-192-ONATARIO-AN, and an orange flesh sister of the coupling event. Plants are grown as described in Example 1 and Brix accumulation is measured as described in Example 2. Brix accumulation is reported as a percent of maximum Brix accumulation. (FIG. 11) As shown in FIG. 11, lines with the earliness locus (coupling event and sister line) accumulate Brix earlier than those without. Early lines reach maximum Brix at approximately 32 days, while the red flesh donor and unconverted earliness recurrent parent do not reach maximum Brix until 38 days. Brix accumulation in lines with the earliness locus occurs 4 to 10 days earlier as compared to lines without the earliness locus Values of hue angle are shown in Table 7 for the four comparative lines in the field trial. Plants are grown as described in Example 1 and hue angle measurements are taken as described in Example 2. The red flesh lines have a hue angle less than between 55-63° while orange flesh lines have a hue angle greater than or equal to 64° (Table 7). The coupling event has a hue angle less than the red flesh recurrent parent exemplary of a deeper red flesh.

TABLE 7

Hue angle measurement for the red flesh and earliness
coupling event compared to controls.

| Line Name | Hue Angle |
|---|---|
| Coupling Event | 60.8° |
| Orange sister of event | 74.7° |
| Earliness recurrent parent | 71.2° |
| Red Flesh recurrent parent | 63.2° |

As described in Example 4, high carotenoid content correlates to red flesh color. In order to quantify the difference in total carotenoids in the coupling event, the four comparative lines described above are tested to determine the effect of the locus (Table 8). Plants are grown as described in Example 1 and carotenoid measurements are taken as described in Example 2. As shown in Table 8, red flesh lines have 2 to 3 times more total carotenes than the orange flesh lines.

TABLE 8

Total carotenes (parts per million) for the red flesh and earliness coupling event compared to controls.

| Line name | Flesh color | Total carotenes (ppm) |
|---|---|---|
| Coupling Event | Red | 54.130 |
| Orange sister of event | Orange | 24.176 |
| Earliness recurrent parent | Orange | 26.249 |
| Red Flesh Donor | Red | 51.662 |

Example 6. Selection of Coupling Events in a Breeding Program

Standard breeding, genotyping, and selection techniques can be used to introgress the red flesh and earliness coupling event in known melon varieties and market classes lacking a red flesh locus on Linkage Group 4 of the Monsanto Consensus Genetic Map, an earliness locus on Linkage Group 4 of the Monsanto Consensus Genetic Map, or coupled red flesh and earliness loci on Linkage Group 4 of the Monsanto Consensus Genetic Map. An earliness donor can be used as a source of the earliness trait, such as the non-limiting example CHA-192-ONTARIO-AN A red flesh donor can be used as a source of the red flesh trait, such as the non-limiting examples CHA-192-0058-MO, CHA-192-0034-AN, ITAAZ11-7001M0, and CHA-ZA15-0014AN. A red flesh and earliness coupled donor can be used as a source of the coupling event, such as CHA-ZA15-0014AN (deposited under ATCC accession number PTA-124202), or a progeny thereof.

Recombination events that combine the earliness locus and red flesh locus on Linkage Group 4 of the Monsanto Consensus Genetic Map can be selected by screening progeny plants for the specific alleles of flanking markers. The first boundary of a coupling event can be detected using the flanking markers NU0243432, NU0220305, or both. In a $F_1$ generation, detection of a heterozygous G nucleotide at marker NU0243432, a heterozygous C nucleotide at marker NU0220305, or both is selected. In subsequent generations, detection of a heterozygous or homozygous G nucleotide at marker NU0243432, a heterozygous or homozygous C nucleotide at marker NU0220305, or any combination thereof is selected.

The second boundary of a coupling event can be detected using the flanking markers NCMEL009758372, NCMEL008579265, or both. In a $F_1$ generation, detection of a heterozygous T nucleotide at marker NCMEL009758372, a heterozygous T nucleotide at marker NCMEL008579265, or both is selected. In subsequent generations, detection of a homozygous T nucleotide at marker NCMEL009758372, a homozygous T nucleotide at marker NCMEL008579265, or both is selected.

A *Cucumis melo* plant with earliness and red flesh will comprise an allele described above for marker NU0243432, NU0220305 or both and an allele described above for marker NCMEL009758372, NCMEL008579265, or both.

DEPOSIT INFORMATION

A deposit of the proprietary inbred plant line disclosed above and recited in the appended claims have been made with American Type Culture Collection (ATCC), 10801 University Boulevard, Manassas, VA 20110. The date of deposit for CHA-ZA15-0014AN was May 12, 2017. The deposits of 2500 seeds was taken from the same deposits maintained since prior to the filing date of this application. Upon issuance of a patent, all restrictions upon the deposits will be irrevocably removed, and the deposits are intended by Applicant to meet all of the requirements of 37 C.F.R. § 1.801-1.809. The ATCC has issued the following accession number: ATCC Accession No. PTA-124202 for CHA-ZA15-0014AN. This deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

What is claimed is:

1. A *Cucumis melo* plant, or part thereof, wherein said *Cucumis melo* plant comprises a trait locus conferring a red flesh phenotype, wherein said red flesh trait locus is located in a genomic region flanked by nucleic acid markers NCMEL0085795265 (SEQ ID NO: 1) and NU0220305 (SEQ ID NO: 2).

2. The *Cucumis melo* plant, or part thereof, of claim 1, wherein said part is selected from the group consisting of seed, leaf, cotyledon, pollen, embryo, root, root tip, anther, pistil, flower, bud, fruit, seed, stalk, and meristem.

3. The *Cucumis melo* plant, or part thereof, of claim 1, wherein said red flesh trait locus is homozygous.

4. The *Cucumis melo* plant, or part thereof, of claim 3, wherein said part is a mature fruit comprising red flesh with a hue angle between 55° and 63°.

5. The *Cucumis melo* plant, or part thereof, of claim 3, wherein said part is a mature fruit comprising total carotenes of at least 40 parts per million.

6. The *Cucumis melo* plant, or part thereof, of claim 3, wherein said part is a mature fruit comprising 15 parts per million or greater total carotenes more than a mature fruit obtained from an isogenic plant lacking said homozygous red flesh trait locus when grown under similar conditions.

7. The *Cucumis melo* plant, or part thereof, of claim 3, wherein said *Cucumis* plant is *Cucumis melo* cultivar CHA-ZA15-0014AN or is derived from *Cucumis melo* cultivar CHA-ZA15-0014AN, wherein said *Cucumis melo* plant derived from *Cucumis melo* cultivar CHA-ZA15-0014AN comprises said red flesh trait locus, a representative sample seed of *Cucumis melo* cultivar CHA-ZA15-0014AN having been deposited with the ATCC under ATCC Accession No. PTA-124202.

8. A method of producing a *Cucumis melo* plant, or part thereof, comprising,
   a. growing a first *Cucumis melo* plant comprising a trait locus conferring a red flesh phenotype, wherein said red flesh trait locus is located in a genomic region flanked by nucleic acid markers NCMEL0085795265 (SEQ ID NO: 1) and NU0220305 (SEQ ID NO: 2);
   b. crossing said first *Cucumis melo* plant to a second *Cucumis melo* plant; and
   c. selecting a progeny *Cucumis melo* plant, or part thereof, comprising said red flesh trait locus.

9. The method of claim 8, further comprising harvesting seed from a fruit of said selected progeny *Cucumis melo* plant.

10. The method of claim 8, wherein said second *Cucumis melo* plant further comprises said red flesh trait locus.

11. The method of claim 8, wherein said second *Cucumis melo* plant is an elite variety of *Cucumis melo*.

12. The method of claim 8, wherein said first *Cucumis melo* plant is a *Cucumis melo* cultivar CHA-ZA15-0014AN or is derived from *Cucumis melo* cultivar CHA-ZA15-0014AN, wherein said *Cucumis melo* plant derived from *Cucumis melo* cultivar CHA-ZA15-0014AN comprises said red flesh trait locus, a representative sample seed of *Cucumis melo* cultivar CHA-ZA15-0014AN having been deposited with the ATCC under ATCC Accession No. PTA-124202.

\* \* \* \* \*